(12) United States Patent
Uchimura et al.

(10) Patent No.: US 12,140,542 B2
(45) Date of Patent: Nov. 12, 2024

(54) OPTICAL ANALYSIS CHIP

(71) Applicant: NATIONAL UNIVERSITY CORPORATION EHIME UNIVERSITY, Matsuyama (JP)

(72) Inventors: Hiromi Uchimura, Shikokuchuo (JP); Tomoki Yabutani, Shikokuchuo (JP)

(73) Assignee: NATIONAL UNIVERSITY CORPORATION EHIME UNIVERSITY, Matsuyama (JP)

( * ) Notice: Subject to any disclaimer, the term of this patent is extended or adjusted under 35 U.S.C. 154(b) by 322 days.

(21) Appl. No.: 17/599,173

(22) PCT Filed: Mar. 27, 2020

(86) PCT No.: PCT/JP2020/013938
§ 371 (c)(1),
(2) Date: Sep. 28, 2021

(87) PCT Pub. No.: WO2020/196817
PCT Pub. Date: Oct. 1, 2020

(65) Prior Publication Data
US 2022/0155226 A1   May 19, 2022

(30) Foreign Application Priority Data
Mar. 28, 2019   (JP) .................. 2019-062478

(51) Int. Cl.
*G01N 21/64* (2006.01)
*B01L 3/00* (2006.01)
(Continued)

(52) U.S. Cl.
CPC ...... *G01N 21/645* (2013.01); *B01L 3/502707* (2013.01); *B01L 3/502715* (2013.01);
(Continued)

(58) Field of Classification Search
CPC .. G01N 21/645; G01N 21/03; G01N 21/3103; G01N 33/558; G01N 21/251;
(Continued)

(56) References Cited

U.S. PATENT DOCUMENTS

| | | | |
|---|---|---|---|
| 8,628,729 B2* | 1/2014 | Carrilho | F16K 99/0015 436/805 |
| 2002/0001546 A1* | 1/2002 | Hunter | B01L 3/5025 427/255.18 |

(Continued)

FOREIGN PATENT DOCUMENTS

| | | |
|---|---|---|
| JP | 2004510996 A | 4/2004 |
| JP | 2009-115822 A | 5/2009 |

(Continued)

*Primary Examiner* — Edmond C Lau
*Assistant Examiner* — Noah J. Haney
(74) *Attorney, Agent, or Firm* — Muncy, Geissler, Olds & Lowe, P.C.

(57) ABSTRACT

An analysis tool for use in optical analysis, comprising a detection unit 10 having through-holes 10*h* penetrating through the surface and the rear side of a base material 11, the detection unit 10 comprising, inside of the base material 11, a plurality of voids 11*h* that allows a liquid to pass through by capillary action and that communicate with the through-holes 10*h*, and the through-holes 10*h* being formed with a size that enables a liquid to be held by surface tension. Therefore, by irradiating the detection unit 10 with light, it is possible to obtain transmitted light L2 that has been transmitted through a liquid film Lf. By analyzing the transmitted light L2, a target component in a sample L can be appropriately quantified.

24 Claims, 22 Drawing Sheets

(51) Int. Cl.
  *G01N 21/03* (2006.01)
  *G01N 21/31* (2006.01)
  *G01N 33/558* (2006.01)
  *G01N 21/25* (2006.01)
  *G01N 37/00* (2006.01)

(52) U.S. Cl.
  CPC ......... *G01N 21/03* (2013.01); *G01N 21/3103* (2013.01); *G01N 33/558* (2013.01); *B01L 3/50273* (2013.01); *B01L 2300/165* (2013.01); *B01L 2400/0406* (2013.01); *G01N 2021/035* (2013.01); *G01N 21/251* (2013.01); *G01N 21/31* (2013.01); *G01N 2021/6482* (2013.01); *G01N 37/00* (2013.01)

(58) Field of Classification Search
  CPC .. G01N 21/31; G01N 37/00; G01N 2021/035; G01N 2021/6482; B01L 3/502707; B01L 3/502715; B01L 3/50273; B01L 2300/165; B01L 2400/0406
  USPC .......................................................... 356/244
  See application file for complete search history.

(56) References Cited

U.S. PATENT DOCUMENTS

| | | | | |
|---|---|---|---|---|
| 2003/0092034 A1* | 5/2003 | Cooper | ............. | G01N 21/7703 435/6.19 |
| 2004/0208792 A1* | 10/2004 | Linton | ................. | C12Q 1/6858 435/286.1 |
| 2006/0013031 A1* | 1/2006 | Ravkin | .................. | B82Y 30/00 365/63 |
| 2006/0159916 A1* | 7/2006 | Dubrow | ............... | B01J 20/3219 428/401 |
| 2008/0293129 A1* | 11/2008 | Kawahara | ............ | B01L 3/5085 435/287.2 |
| 2009/0011947 A1* | 1/2009 | Ozawa | ............... | G01N 21/6452 506/9 |
| 2010/0261159 A1* | 10/2010 | Hess | .................... | B01J 19/0046 435/7.1 |
| 2013/0084630 A1* | 4/2013 | Rolland | ................. | G01N 21/78 435/287.8 |
| 2015/0045252 A1* | 2/2015 | Maher | ................. | B01L 3/50857 506/9 |
| 2015/0080247 A1* | 3/2015 | Pallas | ................. | B01L 3/50851 435/6.12 |
| 2015/0211996 A1* | 7/2015 | Kamba | ................... | G01N 21/59 356/434 |
| 2016/0116427 A1* | 4/2016 | Laurenson | ............... | B05D 5/00 427/2.13 |
| 2016/0202289 A1* | 7/2016 | Nain | ................. | G01N 33/4833 850/10 |
| 2017/0242234 A1* | 8/2017 | Ashcroft | ............. | G01N 15/1463 |
| 2017/0307606 A1* | 10/2017 | Hallock | ................. | C12M 23/12 |
| 2018/0353956 A1* | 12/2018 | Bandara | ............. | B01L 3/502707 |
| 2021/0308666 A1* | 10/2021 | Chou | ..................... | G01N 21/01 |

FOREIGN PATENT DOCUMENTS

| | | | | |
|---|---|---|---|---|
| JP | 2012-230125 A | 11/2012 | | |
| JP | 2013-53869 A | 3/2013 | | |
| JP | 2013-148592 A | 8/2013 | | |
| JP | 2014-529083 A | 10/2014 | | |
| WO | 01/06244 A2 | 1/2001 | | |
| WO | WO-2006105110 A2 * | 10/2006 | ........ | B01L 3/502746 |

* cited by examiner

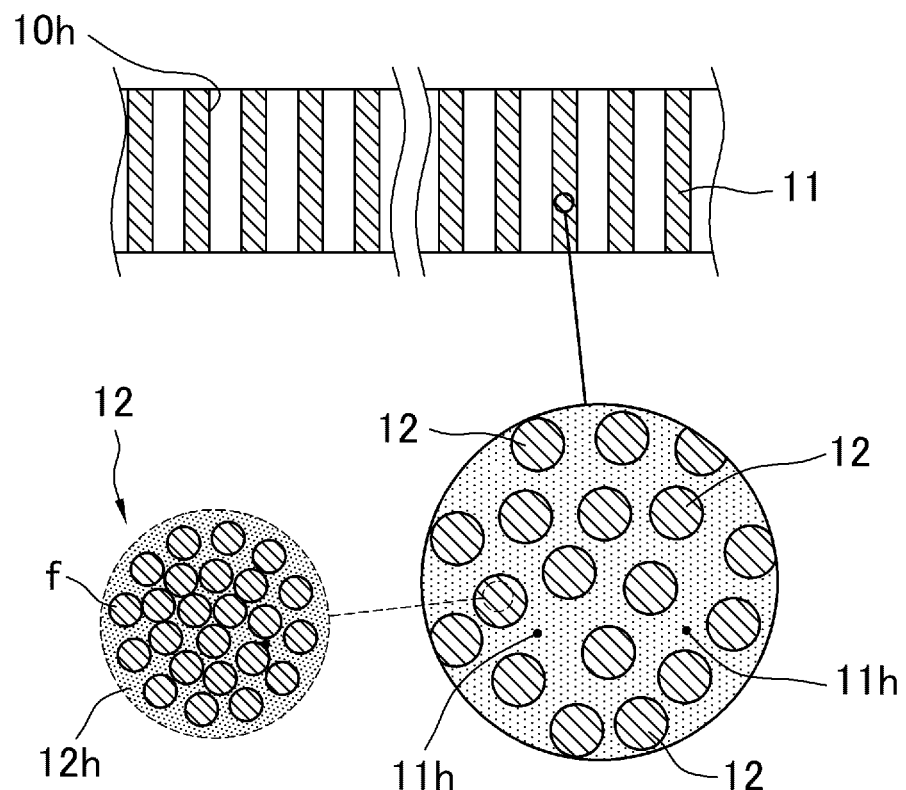
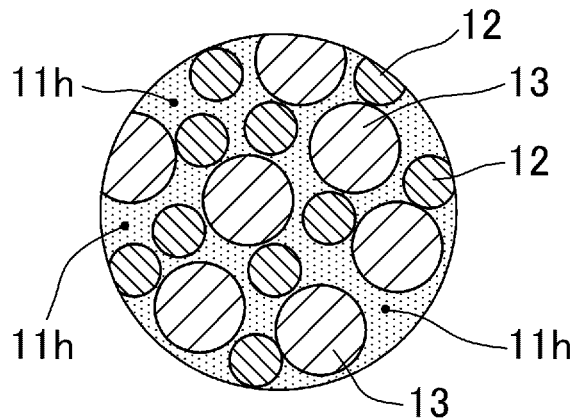
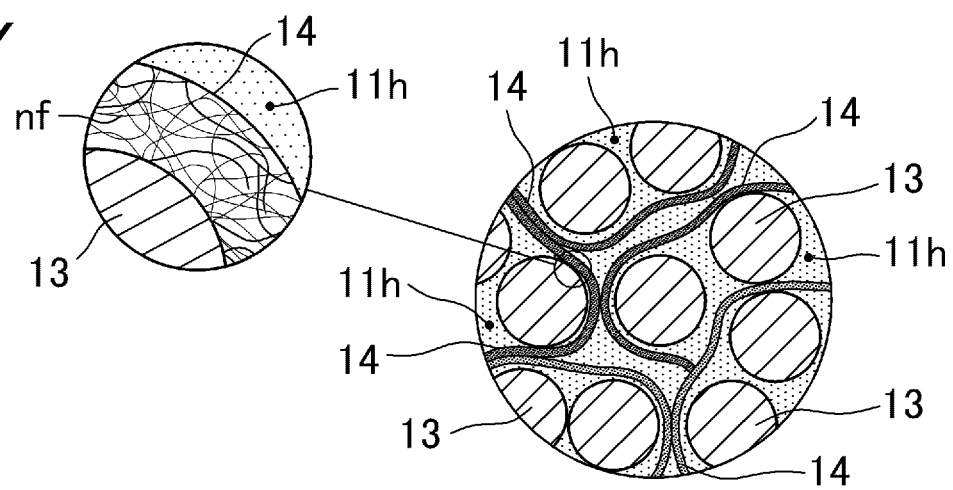
FIG.2A
FIG.2X
FIG.2Y

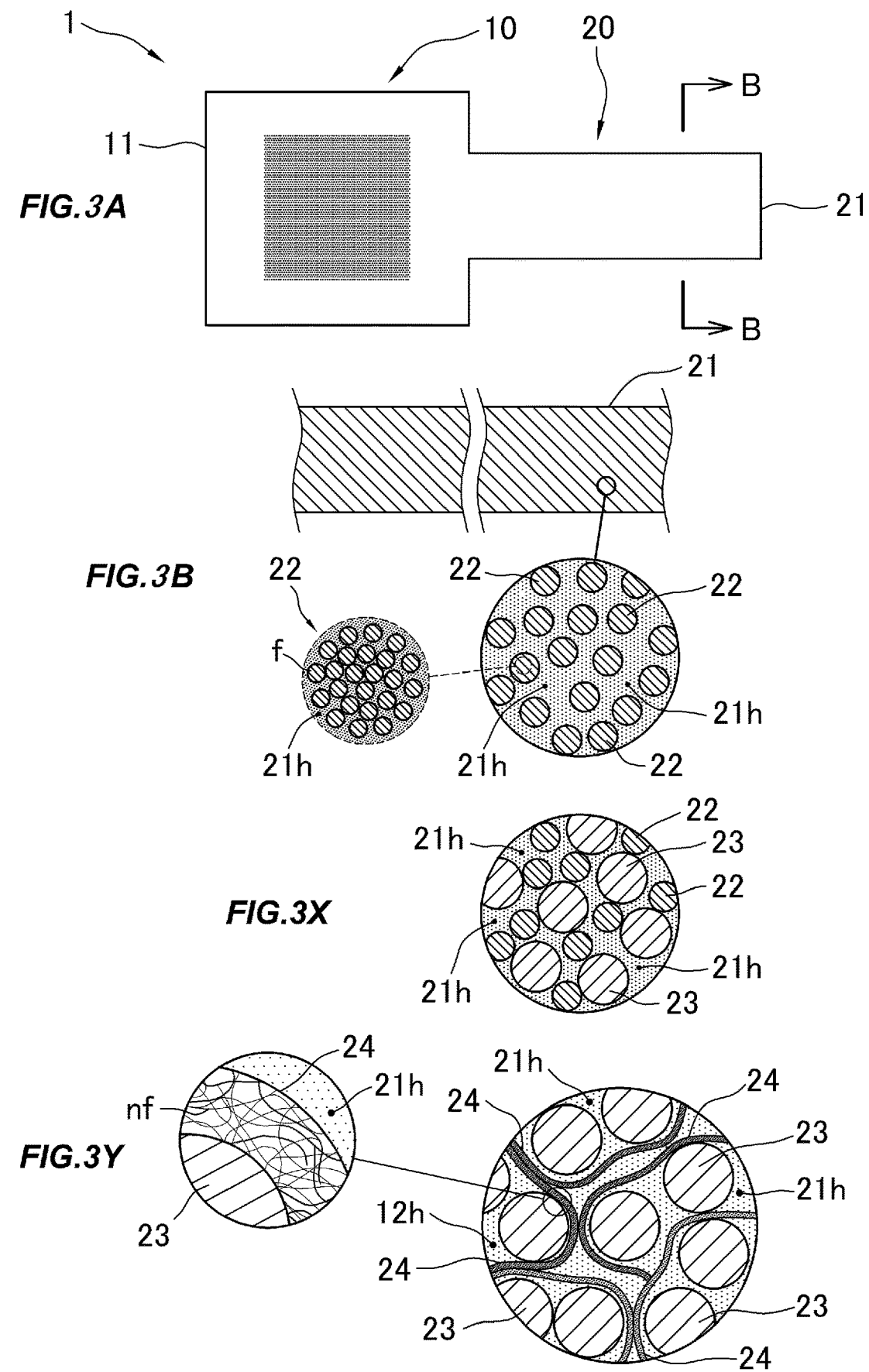

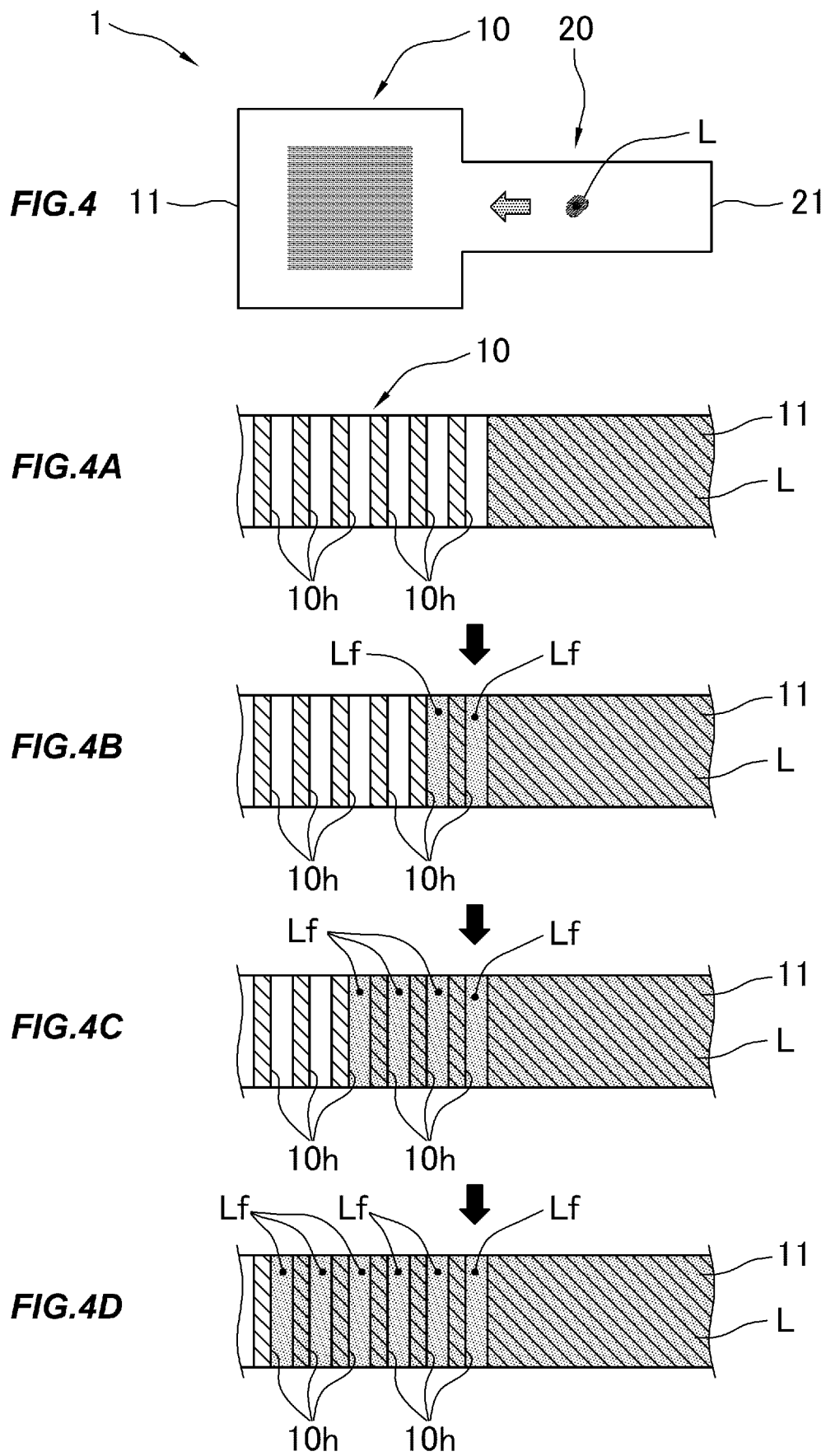

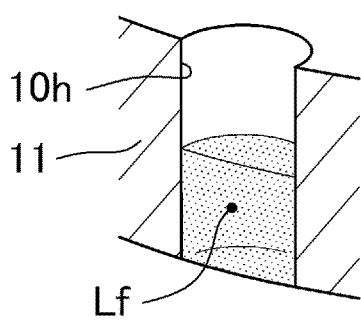
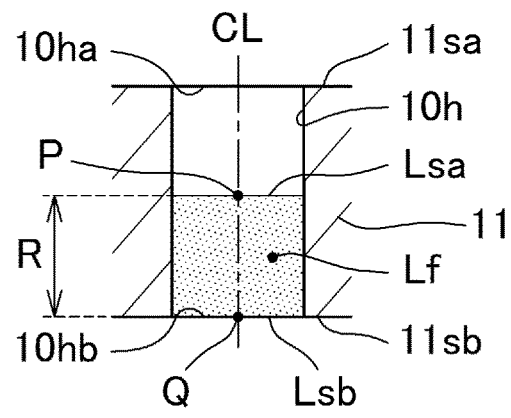
*FIG.6A*
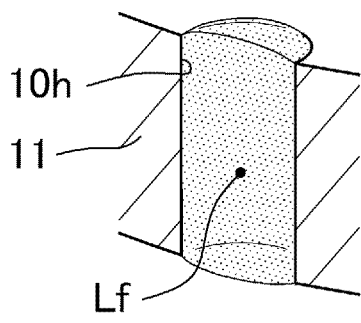
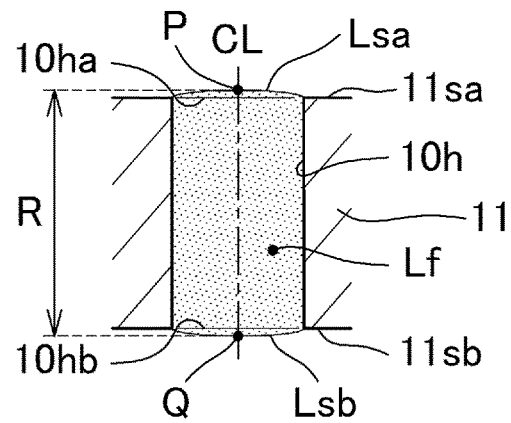
*FIG.6B*
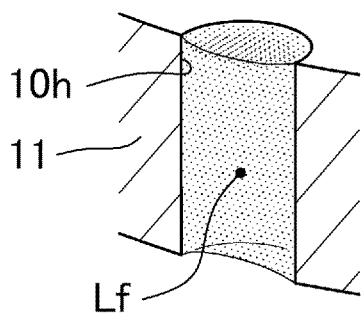
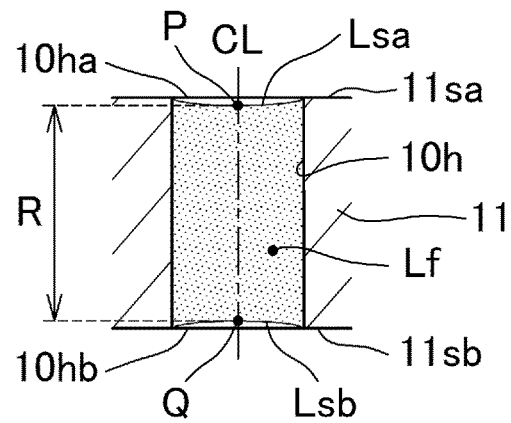
*FIG.6C*
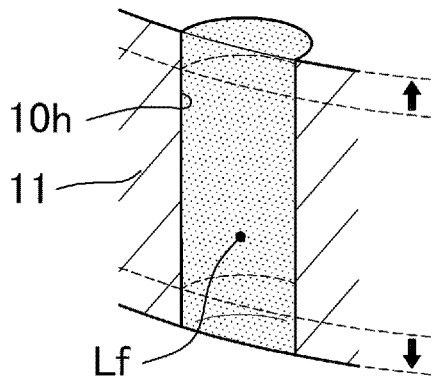
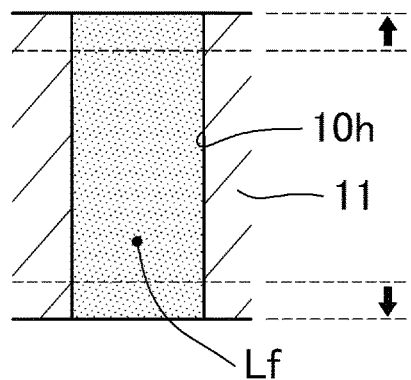
*FIG.6D*

THROUGH HOLE REGION
THROUGH HOLE

THROUGH HOLE

DL
WL

CALIBRATION CURVE OF ULTRAVIOLET-VISIBLE
ABSORPTION SPECTRUM OF
Fe(II)-1,10-PHENANTHROLINE COMPLEX

CALIBRATION CURVE OF ULTRAVIOLET-VISIBLE
ABSORPTION SPECTRUM OF SODIUM COPPER
PHTHALOCYANINE TETRASULFONATE

*FIG.14A*
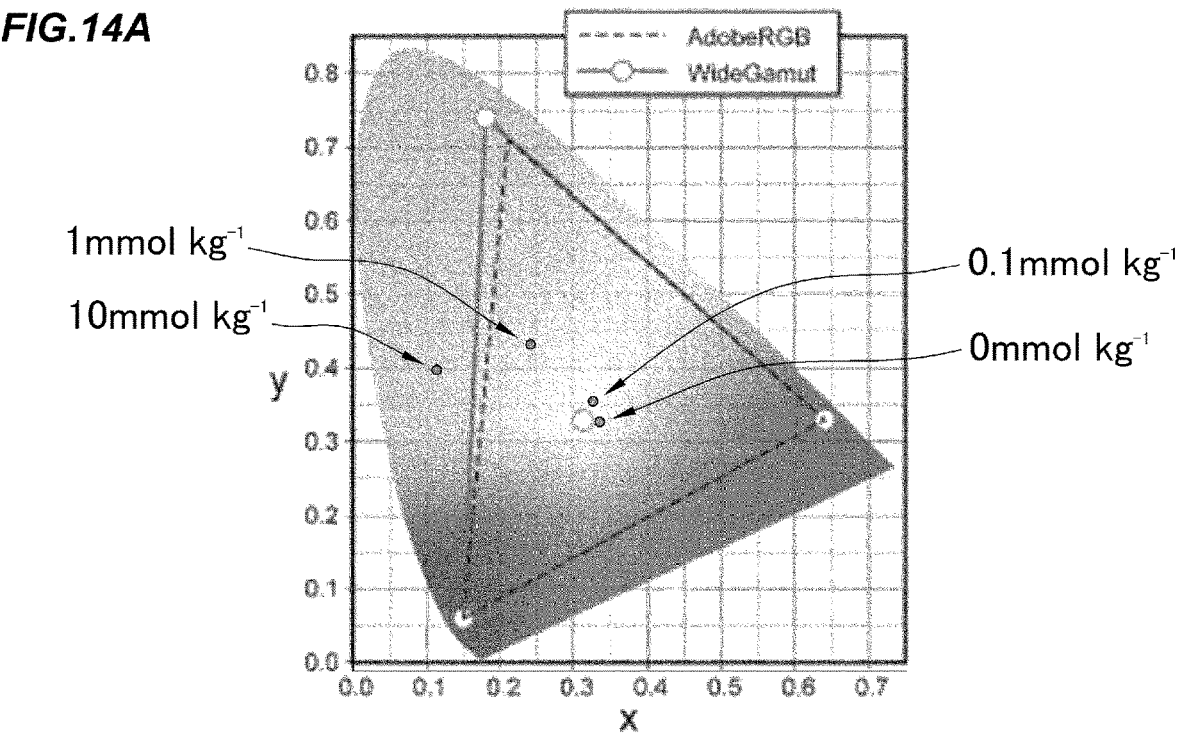
*FIG.14B*
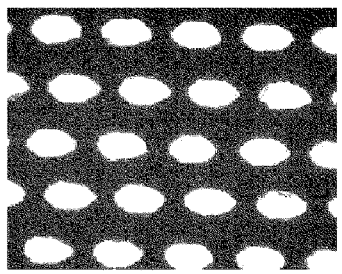
R VALUE 255, G VALUE 255,
B VALUE 255
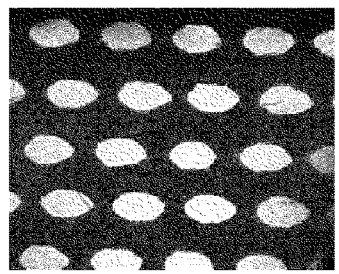
R VALUE 225, G VALUE 250,
B VALUE 219
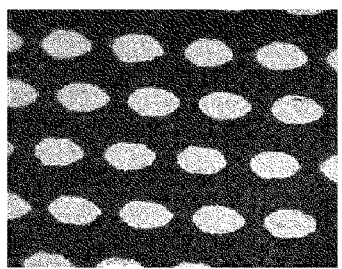
R VALUE 136, G VALUE 249,
B VALUE 185
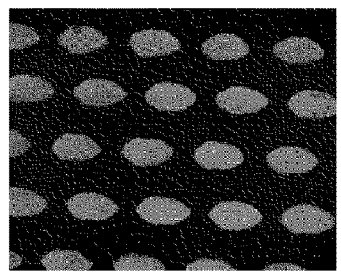
R VALUE 40, G VALUE 144,
B VALUE 174

OPTICAL ANALYSIS CHIP

TECHNICAL FIELD

The present invention relates to an optical analysis chip. More specifically, the present invention relates to an optical analysis chip that can be used for a wide range of analysis in the fields of medicine, biochemistry, pharmaceutics, chemistry, environment, and the like.

BACKGROUND ART

Recent technologies have started to succeed in diagnosing a large number of diseases using body fluids such as blood or urine. However, the amount of body fluids (hereinafter referred to as a sample) that can be used for the diagnosis is limited. Therefore, it is important to obtain as much information as possible (for example, progress of disease, early detection of disease, and the like) from a small sample.

Patent Literature 1 discloses a simple analysis chip having a multilayer structure treated by photolithography. This chip includes a detection unit that is provided at a top end portion of the flow path of the chip and that includes various coloring materials. Patent Literature 1 describes that when an analysis component is present in a sample, the amount of the target component in the sample is detected by visually evaluating the degree of coloring of the detection unit or based on the amount of change of reflected light.

Patent Literature 2 to Patent Literature 4 also disclose a similar simple analysis chip or test paper, and describe that a change in color tone (colorimetric method) according to the amount of a target component, i.e., the amount of change in reflected light (scattered light) on the surface of a base material, is quantified by way of visual observation or image processing.

CITATION LIST

Patent Literature

Patent Literature 1: Japanese Laid-Open Patent Application Publication No. 2012-230125
Patent Literature 2: Japanese Translation of PCT International Application Publication No. 2014-529083
Patent Literature 3: Japanese Laid-Open Patent Application Publication No. 2013-53869
Patent Literature 4: Japanese Laid-Open Patent Application Publication No. 2009-115822
Patent Literature 5: Japanese Laid-Open Patent Application Publication No. 2013-148592

SUMMARY OF INVENTION

Technical Problem

However, the techniques of Patent Literature 1 to Patent Literature 5 are originally intended to be used to qualitatively measure target components in a sample. They are not techniques for quantitatively analyzing target components in a sample.

In addition, the techniques of Patent Literature 1 to Patent Literature 5 have problems including unevenness (roughness) of chip surface during measurement or susceptibility to external light when the analysis is performed based on the amount of change in reflected light (scattered light), as well as difficulties in objective determination due to individual differences, ambient brightness, and the like, when visual colorimetric analysis is performed.

More specifically, it is well known that although the previously-known simple analysis techniques are capable of qualitative analysis of a target component in a sample, they are incapable of obtaining a quantitative numerical value or ensuring high accuracy because of the variation in measurement value or insufficient sensitivity.

On the other hand, an optical analysis method, such as absorption spectrometry or fluorescence spectrometry, using a detection unit (cell) formed of a transparent material that transmits light, such as quartz, glass, or plastic, has been widely used as an analysis method ensuring excellent quantitativity and high accuracy.

In these optical analysis techniques, a sample is placed in a cell, light is incident on the cell, and the light (for example, transmitted light or fluorescence) resulted from the interaction between the incident light and a target component in the sample is measured, thereby quantifying the target component in the sample.

However, it requires a sample in an amount sufficient to fit into the cell (for example, 0.1 ml to 5 ml) although such an optical analysis method is excellent in quantitativity. Therefore, the method has a drawback in that it is not suitable for analysis of the aforementioned body fluids or the like because only a small amount of sample can be obtained from them.

As described above, at present, there is no technique for quantitatively analyzing a target component in a small amount of sample using an optical analysis method.

In light of the above circumstances, an object of the present invention is to provide an optical analysis chip capable of performing quantitative analysis of a small amount of sample using an optical analysis method.

Solution to Problem

An optical analysis chip of the present invention is an analysis tool for optical analysis, and comprises a detection unit having through-holes penetrating through the surface and the rear side of the base material. The detection unit comprises, in an internal portion of the base material, a plurality of voids that allow a liquid to pass though by capillary action and that communicate with the through-holes. The through-holes are formed with a size with which a liquid can be held by surface tension.

Advantageous Effects of Invention

According to an optical analysis chip of the present invention, by supplying a liquid sample to a detection unit, the supplied liquid sample can form a liquid film in the through-holes. Then, by exposing the detection unit to light, it is possible to obtain transmitted light that has been transmitted through the liquid film. Further, by analyzing the transmitted light, it is possible to appropriately quantify the target component in the sample.

BRIEF DESCRIPTION OF DRAWINGS

FIG. 1(A) is a schematic plan view,
FIG. 1(B) is a schematic cross-sectional view, taken along line B-B of a detection unit 10 of FIG. 1(A),
and FIG. 1(C) is a schematic explanatory view of a through-hole 10$h$.

FIG. 2 is a schematic explanatory view of a base material 11 of the detection unit 10 of the optical analysis chip 1 of the present embodiment obtained by further enlarging an enlarged cross-sectional view, taken along line IIA-IIA of the detection unit 10 of FIG. 1. FIG. 2(A) is a schematic explanatory view of the base material 11 formed of a water-permeable material 12, and FIG. 2(X) and FIG. 2(Y) are schematic explanatory views each illustrating the base material 11 formed of another material. FIG. 2(X) is a schematic explanatory view of the base material 11 formed of the water-permeable material 12 and a water-impermeable material 13, and FIG. 2(Y) is a schematic explanatory view of the base material 11 formed of a nanofiber layer 14 and the water-impermeable material 13.

FIG. 3 is a schematic explanatory view of the optical analysis chip 1 of the present embodiment. FIG. 3(A) is a schematic plan view, FIG. 3(B) is a cross-sectional view, taken along line B-B of a flow path base material 21 of a flow path unit 20 of FIG. 3(A), and also a schematic explanatory view of the flow path base material 21 formed of the water-permeable material 12, and FIG. 3(X) and FIG. 3(Y) are schematic explanatory views each illustrating the flow path base material 21 formed of another material. FIG. 3(X) is a schematic explanatory view of the flow path base material 21 formed of a water-permeable material 22 and a water-impermeable material 23, and FIG. 3(Y) is a schematic explanatory view of the flow path base material 21 formed of the nanofiber layer 24 and the water-impermeable material 23.

FIG. 4 is a schematic explanatory view illustrating a sample movement state when a sample L is supplied to the optical analysis chip 1 of the present embodiment, and a liquid film Lf formed on the through-holes 10$h$.

FIG. 6(A) to FIG. 6(C) are schematic explanatory views illustrating changes in liquid surface shape of the liquid film Lf formed in the through-hole 10$h$ when the sample L is supplied to the optical analysis chip 1 of the present embodiment, and FIG. 6(D) is a schematic explanatory view of a state in which the base material 11 is swollen by the sample L.

FIG. 10(B) is a schematic explanatory view illustrating the shape of the through-hole 10$h$.

FIGS. 14(A) and 14(B) are diagrams showing the results of Analysis 2 of Experiment 2. FIG. 14(A) is a graph obtained by expressing an RGB color system as an XY biaxial plane, and FIG. 14(B) is a diagram showing a coloring state of a liquid film.

DESCRIPTION OF EMBODIMENTS

Hereinbelow, embodiments of the present invention are described by referring to drawings.

A optical analysis chip of the present embodiment is an analysis tool for optical analysis, and is characterized in that it enables quantitative analysis with a simple operation even with a small amount of sample.

In the specification, a sample refers to a liquid sample, and components and the like present in the sample are not particularly limited. Examples of sample include blood, environmental water such as river water, factory waste water discharged from a factory, and the like.

First, before describing the features of the optical analysis chip of the present embodiment in detail, an outline of the optical analysis chip and a spectrometer that analyzes the optical analysis chip of the present embodiment are described.

The optical analysis in the present specification refers to a technique for analyzing a target component in a sample based on light obtained after the sample is irradiated with light. Various methods can be used as an analyzing means for analyzing the obtained light. For example, absorption spectrometry, fluorescence spectrometry, color tone analysis, or the like can be used as the analyzing means. The details of these means are described later.

Figure 1A:
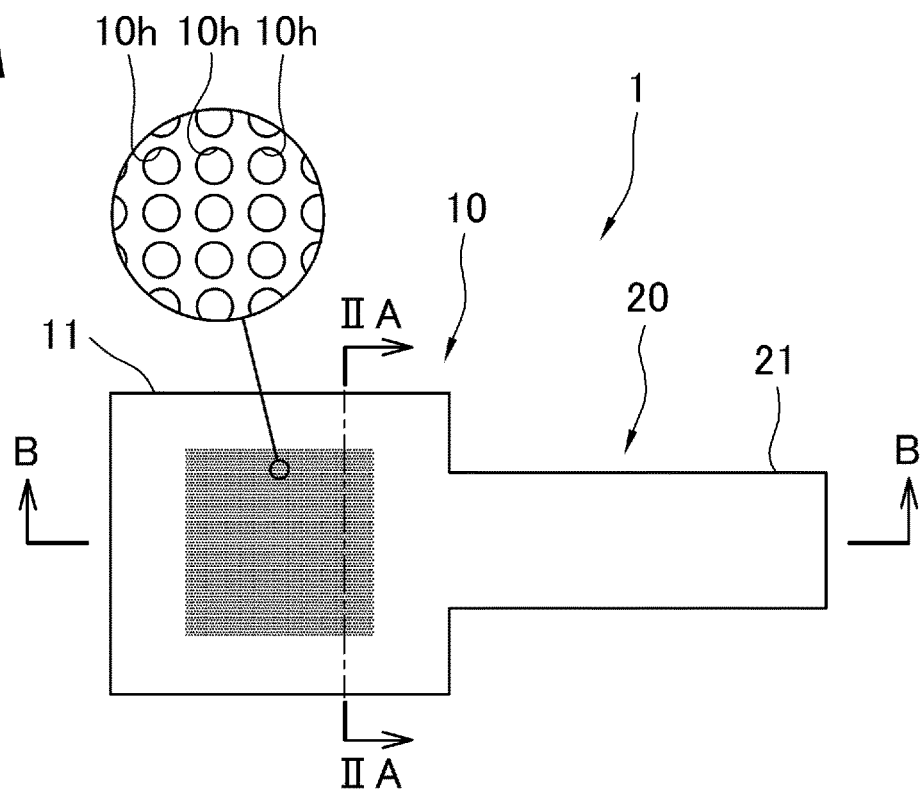
FIGS. 1(A) to 1(C) are schematic explanatory views of an optical analysis chip 1 according to the present embodiment.
Figure 1B:
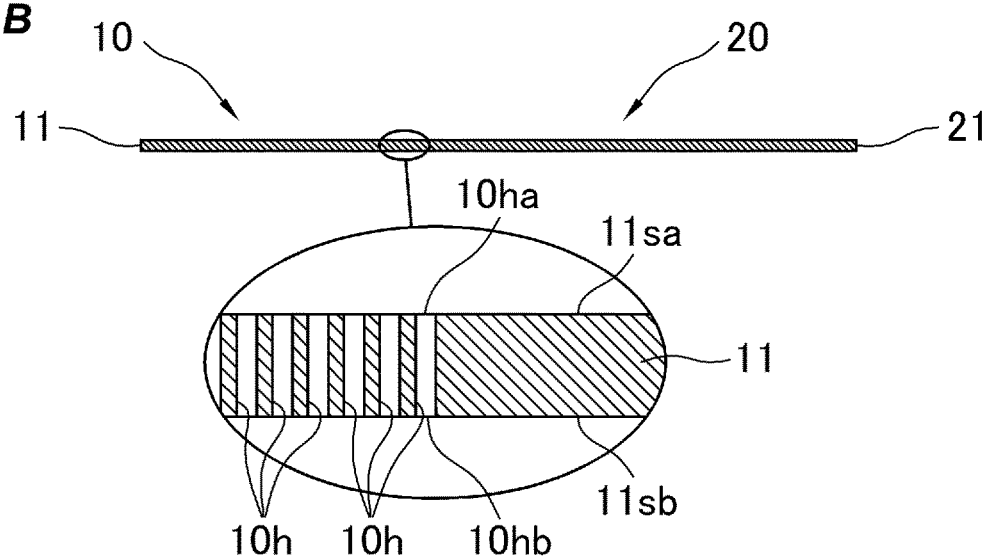
Figure 1C:
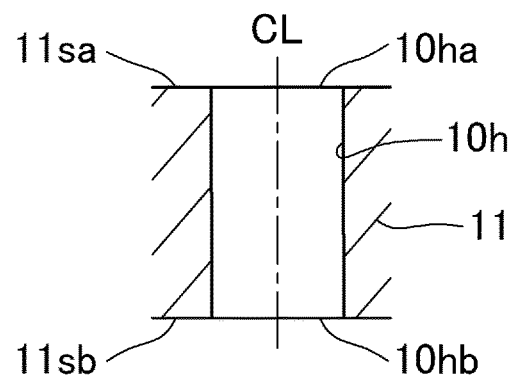
Figure 9:
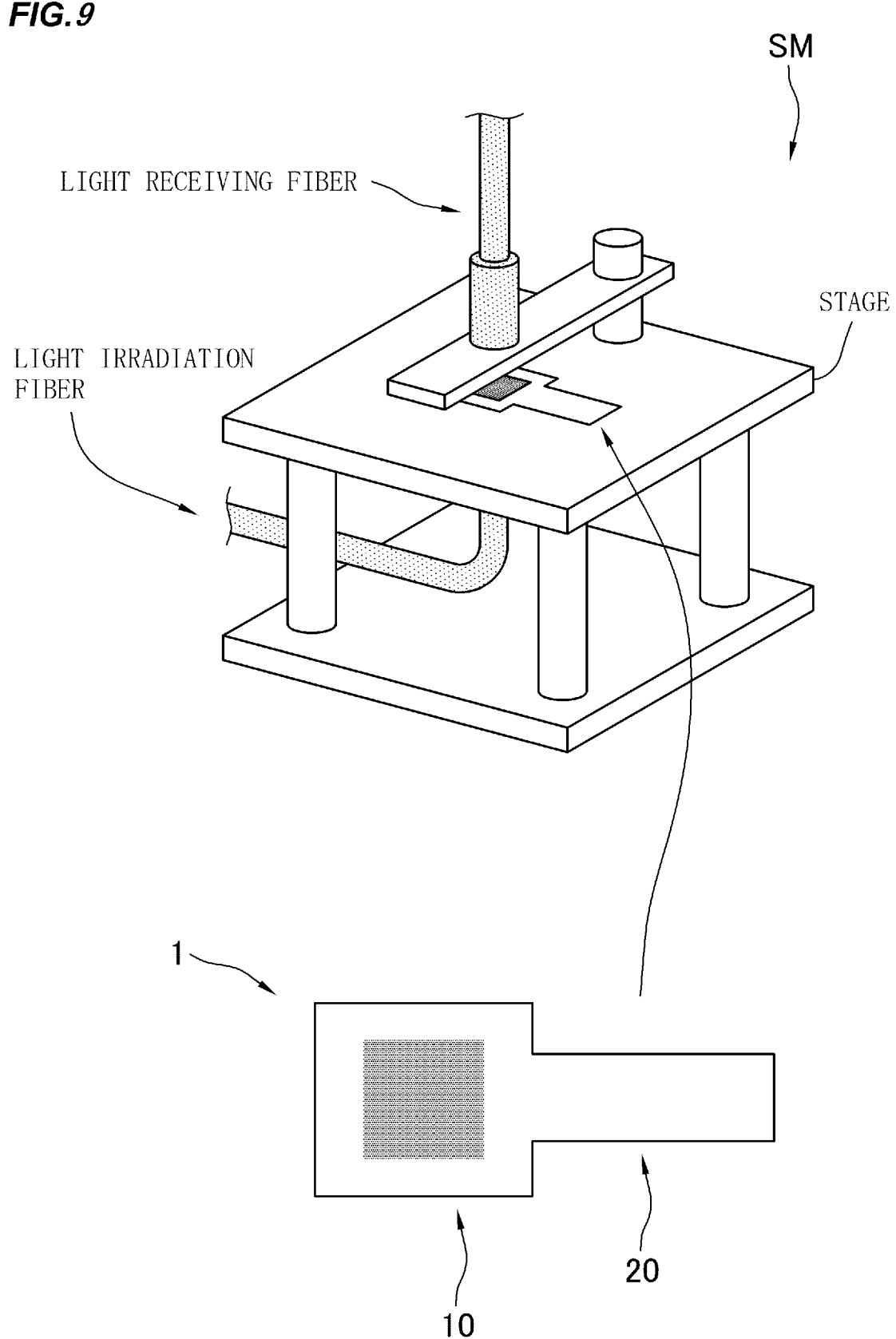
FIG. 9 is a schematic explanatory view illustrating a spectrometer SM used for optical analysis of the optical analysis chip 1 of the present embodiment.

As shown in FIG. 1, reference numeral 1 denotes a plate-shaped optical analysis chip of the present embodiment (hereinafter, this optical analysis chip is simply referred to as an optical analysis chip 1). Reference numeral SM in FIG. 9 represents a spectrometer used to analyze the optical analysis chip 1.

Overview of Detection Unit 10 of Optical Analysis Chip 1

As shown in FIGS. 1 and 2, the optical analysis chip 1 includes a detection unit 10. The detection unit 10 includes a plate-shaped base material 11. The base material 11 is a member through which a liquid can pass, and has through-holes 10$h$ that penetrate through the surface and the rear side thereof. As shown in FIG. 2, a plurality of voids 11$h$ through which a liquid can pass by capillary action are formed in an internal portion of the base material 11. The voids 11$h$ are so formed as to communicate with the through-holes 10$h$. Each through-hole 10 is formed with a size capable of holding a liquid by surface tension.

Figure 5:
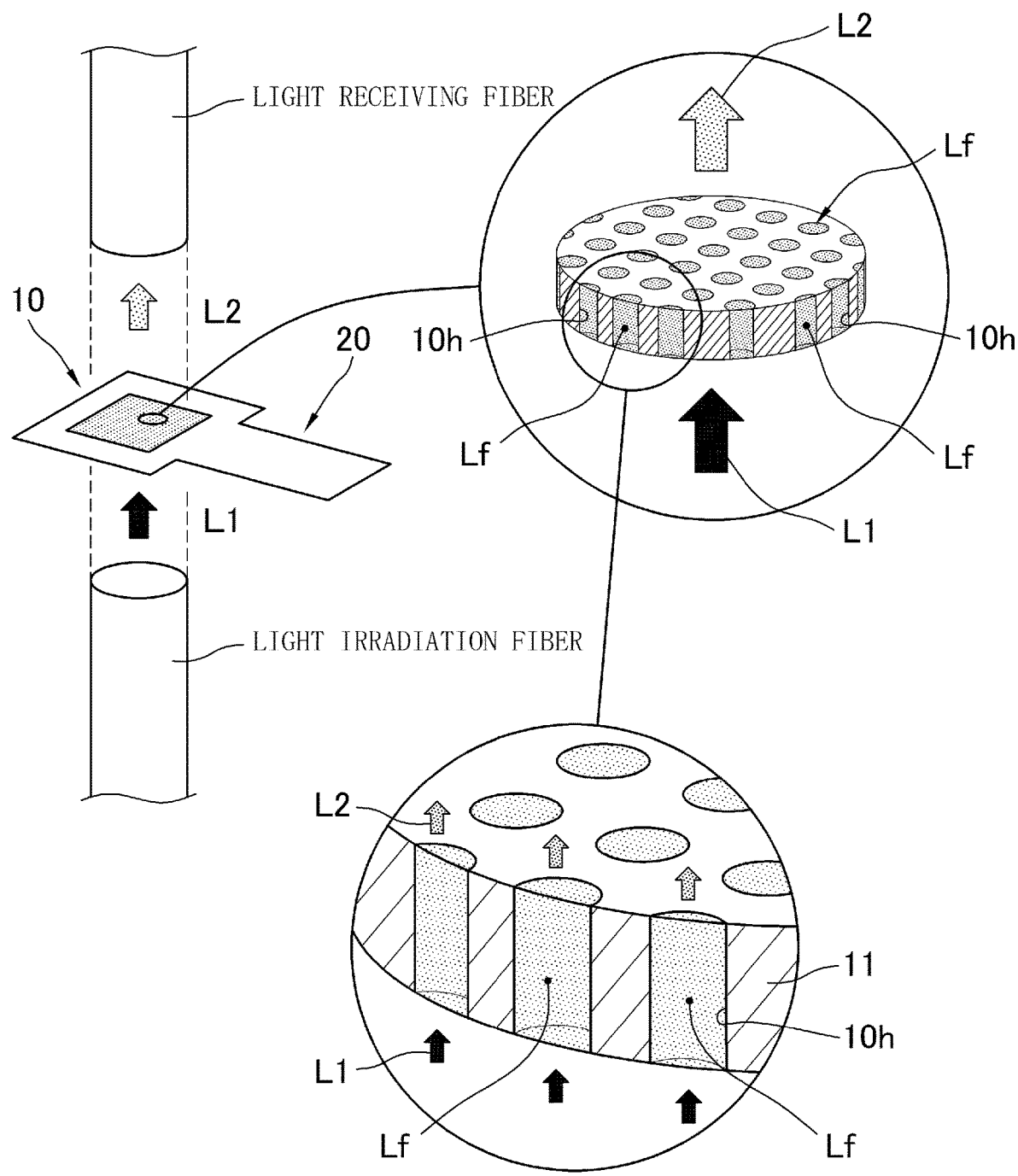
FIG. 5 is a schematic explanatory view illustrating optical analysis using the optical analysis chip 1 of the present embodiment.

As shown in FIGS. 4 and 5, when a sample L is supplied to the detection unit 10, the detection unit 10 moves the sample L in the plurality of voids 11h formed therein so that the sample L is supplied into the through-holes 10h. Then, the sample L supplied into the through-holes 10h is held within the through-holes 10h by surface tension. More specifically, the sample L supplied into the through-holes 10h forms a film (liquid film Lf) inside the through-holes 10h. This liquid film Lf is used for the optical analysis described later.

Although it is allowable to provide only one through-hole 10h, it is more desirable to form a plurality of through-holes 10h in view of improving accuracy. The expression "a plurality of" means a number of two or more.

As shown in FIG. 4, when a plurality of through-holes 10h are formed in the base material 11 of the detection unit 10, the plurality of voids 11h that enable a liquid to pass through by capillary action are formed in the base material 11. Therefore, when a sample is supplied to one of the through-holes 10h, the sample L can be automatically moved (spread) to an adjacent through-hole 10h. The sample L supplied to the through-hole 10h is held within the through-hole 10h by surface tension and forms a liquid film Lf. Then, this phenomenon continuously occurs in the detection unit 10, and the liquid film Lf of the sample L can be formed over the entire through-holes 10h (see FIGS. 4 and 5).

As shown in FIGS. 1 and 2, each through-hole 10h of the detection unit 10 is formed so that it is substantially orthogonal to the surface-wise direction of the base material 11.

More specifically, each through-hole 10h is formed by penetrating through the surface and the rear side of the base material 11 in a manner such that a central axis CL of the through-hole 10h connecting the center of a surface opening 10ha formed on the surface of the base material 11 and the center of a rear side opening 10hb of the through-hole 10h formed on the rear side of the base material 11 is substantially orthogonal to the plane (a surface 11sa and/or a rear side 11sb) of the base material 11. By forming the through-hole 10h so that the central axis CL thereof is substantially orthogonal to the plane, i.e., the surface 11sa and the rear side 11sb, of the base material 11, the accuracy in the analysis of the sample L becomes possible to be improved. This effect will be described later in detail.

Spectrometer SM

As shown in FIG. 9, a spectrometer SM includes a stage with a measurement window for setting the optical analysis chip 1; a light source means for emitting irradiation light L1 to the liquid film Lf formed inside the plurality of through-holes 10h of the detection unit 10 of the optical analysis chip 1 installed in the measurement window of the stage; a light receiving means for receiving transmitted light L2 that is obtained after the light emitted from the light source means is transmitted through the liquid film Lf; and an analyzing means for analyzing the light received by the light receiving means.

Note that the measurement window of the stage of the spectrometer SM is formed in communication with the surface and the rear side of the stage of the spectrometer SM, and serves as a communication hole for measurement in which the optical analysis chip 1 is set and held.

For the light receiving means and the analyzing means used in the spectrometer SM, absorption spectrometry, fluorescence spectrometry, color tone analysis, or the like can be used.

The analysis according to each of these methods for analyzing a target component in the sample L is described in turn below.

Analysis Using Absorption Spectrometry or Fluorescence Spectrometry

First, analysis using absorption spectrometry or fluorescence spectrometry is described.

As shown in FIG. 9, in the spectrometer SM, the light source means and the light receiving means are arranged so that they sandwich the measurement window of the stage.

The light source means includes a light source and a light irradiation fiber that causes irradiation of light emitted from the light source. The light irradiation fiber has a base end connected to the light source and is capable of emitting light (irradiation light L1) from the light source, from an irradiation surface on its top end.

The light receiving means includes a light irradiation fiber and a light receiving fiber that receives light (transmitted light L2) obtained after the irradiation light L1 emitted from the light irradiation fiber passes through (transmits through) the liquid film Lf formed in the detection unit 10 of the optical analysis chip 1 disposed in the measurement window. The light receiving fiber has a base end connected to the analyzing means so as to be capable of propagating the transmitted light L2 received by the light receiving surface on its top end to the analyzing means. This analyzing means has a function of converting the light propagated from the light receiving fiber of the light receiving means into a data signal and calculating the concentration of the target component in the sample L based on the converted data signal.

A method for installing the light irradiation fiber and the light receiving fiber is not particularly limited.

For example, as shown in FIG. 9, the light irradiation fiber and the light receiving fiber can be arranged such that the light receiving surface of the light receiving fiber is positioned above the optical axis of the light irradiation fiber via the measurement window. More specifically, the light irradiation fiber is disposed below the measurement window. The irradiation surface of the light irradiation fiber is disposed to face the opening surface of the measurement window. More specifically, the light irradiation fiber is disposed so that the optical axis of the irradiation light L1 emitted from the irradiation surface is orthogonal to the opening surface of the measurement window. Further, the light receiving fiber is arranged to be opposed to the light irradiation fiber, i.e., above the measurement window, so as to allow its light receiving surface to receive the transmitted light L2 obtained after the irradiation light L1 emitted from the irradiation surface of the light irradiation fiber transmits through the liquid film Lf of the detection unit 10.

Then, by disposing the detection unit 10 of the optical analysis chip 1 in the measurement window of the spectrometer SM, it is possible to arrange the irradiation surface of the light irradiation fiber, the detection unit 10 of the optical analysis chip 1, and the light receiving surface of the light receiving fiber in this order from the bottom.

When the spectrometer SM thus arranged is irradiated with this irradiation light L1, the plurality of through-holes 10h (the liquid film Lf formed in the through-holes 10h) of the detection unit 10 and the light receiving surface of the light receiving fiber can be positioned in the irradiation region irradiated with the irradiation light L1. This also enables the light receiving fiber to appropriately receive the transmitted light L2 transmitted through the liquid film Lf on its light receiving surface.

It is desirable to adopt a configuration having a monochromator when the concentration of the target component in the sample L is calculated based on the absorption spectrometry. This monochromator has a function of selecting a ray having a specific wavelength from among the rays of light emitted from the light source, and is provided between the light source and the irradiation surface on the top end of the light irradiation fiber. Examples of the monochromator include a prism, a diffraction grating, an optical filter, and the like. Using a prism has an advantage of enabling selection of electromagnetic waves (rays) in a wide wavelength band.

It is also desirable to appropriately adjust the positional relationship between the optical axis of the irradiation light L1 and the light receiving surface of the light receiving fiber when the concentration of the target component in the sample L is calculated based on the fluorescence spectrometry.

More specifically, the optical system is arranged such that the irradiation light L1 (which is referred to as excitation light in fluorescence spectrometry, and referred to as excitation light L1 in the analysis method described herein) emitted from the light irradiation fiber has a configuration not being directly incident on the light receiving fiber. With such an arrangement, fluorescence analysis can be appropriately performed. More specifically, the excitation light L1 emitted from the light irradiation fiber causes the target component in the liquid film Lf formed in the through-holes 10h of the detection unit 10 of the optical analysis chip 1 to produce fluorescence. This fluorescence thus produced is shifted to the long-wavelength side relative to the emitted excitation light L1. Then, by appropriately detecting the fluorescence obtained based on the target component, the concentration of the target component can be appropriately quantified. For this purpose, the following configuration is employed.

For example, an optical filter for removing lower wavelength optical components from among the rays of the transmitted light L2 transmitted through the liquid film Lf formed in the detection unit 10 is configured to be disposed between the detection unit 10 of the optical analysis chip 1 and the light receiving fiber. Also, considering the fact that the fluorescence obtained based on the target component is emitted in random directions, it is configured to be disposed on the light receiving surface of the light receiving fiber in a direction in which the optical axis of the excitation light L1 emitted from the light irradiation fiber is absent (for example, in the direction perpendicular relative to the traveling direction of the excitation light L1 emitted from the light irradiation fiber).

Method using Color Tone Analysis

Next, analysis using color tone analysis is described.

An optical microscope is configured to be provided instead of the light receiving fiber on the opposite side of the light irradiation fiber when color tone analysis is used.

This configuration is not particularly limited insofar as the state of the liquid film Lf formed in the through-holes 10h of the detection unit 10 of the optical analysis chip 1 can be observed with the optical microscope.

For example, the base end of the optical microscope is connected to the analyzing means to enable the optical microscope to convert the observed image of the liquid film Lf in the through-holes 10h of the detection unit 10 to data and transmit the data to the analyzing means.

This analyzing means has a function of calculating the concentration of the target component in the sample L based on the image data transmitted from the optical microscope. For example, the analyzing means has a function of analyzing the coloring in the image transmitted from the optical microscope using a color space (a color system such as RGB or L*A*B* (Lab color space)) and calculating the concentration of the target component in the sample L from the obtained value.

The optical analysis chip 1 in which the liquid film Lf of the sample L is formed in the through-holes 10h of the detection unit 10 is set in the spectrometer SM configured as described above, and the detection unit 10 is exposed to the irradiation light L1. The irradiation light L1 thus emitted is transmitted through the liquid film Lf formed in the through-holes 10h of the detection unit 10 to generate the transmitted light L2. Then, by analyzing the transmitted light L2 using the optical analysis method, it is possible to appropriately quantify the concentration of the target component in the sample L. That is, the detection unit 10 of the optical analysis chip 1 exhibits the same function as that of a cell used in the previously-known optical analysis. Specifically, the base material 11 of the detection unit 10 of the optical analysis chip 1 corresponds to the cell used in the previously-known optical analysis. Further, the liquid film Lf formed in each through-hole 10h of the base material 11 corresponds to the sample contained in the previously-known cell.

Therefore, the optical analysis chip 1 is capable of quantifying the target component in the sample L based on the same principle as that of the previously-known optical analysis method although the base material 11 of the detection unit 10 is not formed of a light-transmissive transparent material, such as quartz, glass, or plastic.

Further, the length R of the thickness of the liquid film Lf formed in the through-holes 10h of the detection unit 10 of the optical analysis chip 1 corresponds to the optical path length in the optical analysis.

Moreover, the through-holes 10h formed in the detection unit 10 of the optical analysis chip 1 have a size that allows the sample L to be held within the through-holes 10h by surface tension when the sample L is supplied. More specifically, the optical analysis chip 1 is capable of appropriately quantifying the concentration of the target component in the sample L even when the amount of the sample L is very small (for example, about 1 μL to 150 μL).

In addition, the plurality of voids 11h are formed in the base material 11 of the detection unit 10. The voids 11h have a size that enables a liquid to pass through by capillary action. The plurality of voids 11h are also formed to communicate with the plurality of through-holes 10h formed in the base material 11.

With this structure, when the sample L is supplied to a portion of the base material 11 of the detection unit 10, the sample L thus supplied permeates from the surface of the base material 11 into the inside of the base material 11. The sample L thus permeated into the inside of the base material 11 is uniformly supplied into the plurality of through-holes 10h while automatically moving inside the voids 11h due to capillary action. More specifically, even without an attempt to uniformly supply the sample L into the plurality of through-holes 10h, i.e., even if the sample L is supplied only to a portion of the base material 11, the sample L can be substantially uniformly spread into the plurality of through-holes 10h, thereby forming uniform liquid films Lf. Accordingly, obtaining uniform data from the plurality of liquid films Lf becomes possible. More specifically, analyzing data of the plurality of liquid films Lf by a single measurement becomes possible.

Therefore, using the optical analysis chip 1 becomes possible to accurate quantitative determination of the target component in the sample L even when the amount of the sample is small.

Note that a state in which "the sample L is substantially uniformly spread into the plurality of through-holes 10h" refers to a state in which substantially the same amount of the sample L is supplied into each through-hole 10h and the liquid film Lf having substantially the same thickness is formed in each through-hole 10h in the present specification. The amount of the sample L spread into the through-hole 10h is not particularly limited.

Examples of such a state include, a state in which the sample L is spread to fill the entire through-holes 10h, a state in which the sample L is spread to approximately a half of the through-holes 10h (see FIG. 6(A)), and a state in which the sample L is spread to approximately one third of the through-holes 10h (not shown), as shown in FIG. 5, or FIGS. 6(B) and 6(C).

In addition, as shown in FIG. 6, the length R of the liquid film Lf of the sample L spread into the through-holes 10h (specifically, it refers to the length in the thickness-wise direction of the film thickness of the liquid film Lf, and hereinafter simply referred to as liquid film length R) can be measured along the central axis CL of the through-holes 10h.

For example, as shown in FIGS. 6(B) and 6(C), the liquid film length R of the liquid film Lf can be determined from the distance between point P at which an upper surface Lsa of the liquid film Lf and the central axis CL of the through-hole 10h intersect with each other and point Q at which a bottom surface Lsb of the liquid film Lf and the central axis CL of the through-hole 10h intersect with each other.

For example, the liquid film length R of the liquid film Lf and the length of the through-hole 10h in the axis-wise direction (the length of the through-hole 10h in the penetration axis-wise direction) are substantially the same when the sample L is spread to fill the entire through-holes 10h so that the upper surface Lsa of the liquid film Lf and the surface 11sa of the base material 11 are substantially flush with each other and the bottom surface Lsb of the liquid film Lf and the rear side 11sb of the base material 11 are substantially flush with each other. In other words, the liquid film length R of the liquid film Lf and the distance of the base material 11 of the thickness-wise direction in the through-hole region are substantially the same.

On the other hand, the shape of the liquid film Lf changes depending on the properties of the sample L.

For example, as shown in FIG. 6(B), the liquid film Lf may be formed in a meniscus shape in which the upper surface Lsa and the bottom surface Lsb are convex due to surface tension of the sample L. More specifically, the liquid film length R of the liquid film Lf is longer than the length in the axis-wise direction of the through-hole 10h when the sample L is supplied to the detection unit 10 so as to fill the through-hole 10h. Note that an example of the sample L that forms such a convex meniscus shape includes aqueous solutions containing water as a solvent.

Conversely, conversely, as shown in FIG. 6(C), the liquid film Lf may be formed in a meniscus shape in which the upper surface Lsa or the bottom surface Lsb of the liquid film Lf are concave. When such a sample L is spread into the entire through-holes 10h as with the case described above, the liquid film length R of the liquid film Lf is shorter than the length in the axis-wise direction of the through-hole 10h.

Note that this specification refers that the liquid surface Ls (the upper surface Lsa and the bottom surface Lsb) of the liquid film Lf and the base material surface 11s (the surface 11sa and the rear side 11sb) are substantially flat in a cross-sectional view of the through-hole region in a state in which the through-holes 10h are filled with the sample L. More specifically, not only a state in which the liquid surface Ls of the liquid film Lf and the base material surface 11s are flush with each other as described above, but also a state in which the liquid film Lf is formed in a convex or a concave shape is included in the flat state in the present specification.

In addition, when the sample L that the liquid film Lf forms a convex upper surface Lsa or a convex bottom surface Lsb is supplied to the detection unit 10 so as to fill the plurality of through-holes 10h, the convex portion of the liquid film Lf formed to protrude from the surface opening 10ha and/or the rear side opening 10hb of the through-hole 10h may come in contact with and be connected to another adjacent convex portion. If this phenomenon occurs in the entire liquid film Lf formed in the plurality of through-holes 10h, a layer in which the sample L is retained in the surface and/or the rear side of the through-hole region of the base material 11 (stagnation layer) can be formed (see Example FIG. 18).

With the presence of the stagnation layer, the optical path length in the optical analysis can become longer than the case where the upper surface Lsa of the liquid film Lf is flush with the surface 11sa of the base material 11. In other words, the amount of the sample L to be supplied can be increased. Further, the formation of the stagnation layer ensures stable formation of the liquid film Lf in the plurality of through-holes 10h. Therefore, the optical analysis is able to improve the sensitivity in the measurement of the target component in the sample L. Moreover, the formation of the liquid film Lf in the plurality of through-holes 10h is more appropriately performed. Therefore, the accuracy of the quantitative value of the target component in the sample L can be further improved.

Therefore, since the target component of the sample L can be measured with high sensitivity by thus forming the stagnation layer on the surface of the base material 11, the concentration of the target component in the sample L becomes possible to be accurately and stably quantified.

Heretofore, absorption spectrometry or fluorescence spectrometry has been widely used as a optical analysis method because of its high quantitativity and simple detection system. In these optical analysis methods, it is necessary to cause light to be incident on a measurement sample and detect the resulting light (transmitted light, fluorescence, or the like) that has been interacted with a target component in the sample as detection light. Accordingly, a detection unit (cell) formed of a light-transmissive material, such as quartz or glass, is generally used as the vessel for containing the sample. More specifically, the previously-known optical analysis method does not assume use of a cell formed of a light-nontransmissive material, and it is generally regarded that optical analysis cannot be performed with the cell formed of a light-nontransmissive material.

Further, the cell used in the previously-known optical analysis method must be made of a material that prevents the sample contained therein from leaking to the outside from the wall or the like. More specifically, it is necessary to use a material having water resistance and solvent resistance, such as glass, as described above. For this reason, the previously-known optical analysis method does not assume use of a fiber or the like, such as filter paper, molded into a cell shape.

However, the present inventors have found for the first time that it is possible to quantitatively measure the concentration of a target component in a sample using previously-known optical analysis method by forming through-holes in a member corresponding to a cell, and spreading the sample into the through-holes to form a liquid film therein. With this finding, the present inventors arrived at the present invention.

More specifically, even if the base material 11 of the detection unit 10 is formed of a material (for example, fiber, filter paper, water-resistant paper, or the like) that does not transmit or hardly transmits electromagnetic waves, such as ultraviolet, visible or infrared rays, forming the through-holes 10h in the base material 11 allows the optical analysis chip 1 to quantify the concentration of the target component in the sample L based on the optical analysis. In other words, although the base material 11 having the through-holes 10h of the detection unit 10 of the optical analysis chip 1 exerts the same function in the optical analysis as that of the cell used in the previously-known optical analysis, they were configured based on completely different technical ideas.

Moreover, although appropriate quantification cannot be performed unless a certain amount (for example, several ml) of sample is supplied to the cell in the optical analysis method according to the previously-known technique, the optical analysis chip 1 becomes capable of appropriate quantification with an amount of about several μL to several hundreds μL, which is about 1/10 to 1/100 of the amount in the method using the previously-known cell.

Therefore, the optical analysis method using the optical analysis chip 1 becomes capable of appropriate quantification of the target component in the sample L even when the sample amount is small and therefore unsuited for the analysis of the previously-known optical analysis method.

In particular, insofar as the base material 11 of the detection unit 10 of the optical analysis chip 1 has the plurality of through-holes 10h, the concentration of the target component becomes possible to be calculated from the plurality of liquid films Lf at the same time, thereby performing more accurate quantification.

Furthermore, the liquid films Lf formed in the through-holes 10h are held within the through-holes 10h. More specifically, since the material of the liquid film Lf is simply a liquid, it is possible to suppress the influence of absorption of irradiation light or the like caused by the material of the cell, such as plastic or glass, when the sample is held in the cell as in the previously-known technique. For example, the previously-known plastic cells cannot be used in the ultraviolet region having a wavelength of 300 nm or lower, and also cannot be used with organic solvents or strong acids. Further, a strong alkaline solution cannot be used with the previously-known cell made of glass or quartz.

Therefore, it is not necessary to select the analysis method considering the influence of the material of the cell as in the previously-known technique. This provides an advantage that more flexible analysis can be performed.

Further, a detection material that reacts with the target component in the sample L may be supportably placed in the through-holes 10h of the base material 11 of the detection unit 10.

Such a detection material may be appropriately selected and used among various reaction reagents that cause an antigen-antibody reaction, a fluorescent reaction, or the like depending on the target component in the sample L. In this case, the target component in the liquid film Lf reacts with the detection material when the liquid film Lf is formed in the through-holes 10h. Measuring this reaction state based on the optical analysis becomes possible to more selectively quantify the target component.

Details of Structure of Optical Analysis Chip 1

Next, the details of the structure of the optical analysis chip 1 is explained below.

As shown in FIGS. 1 and 3, the optical analysis chip 1 includes the detection unit 10 with a plate-shaped base material 11.

Base Material 11 of Detection Unit 10

The base material 11 of the detection unit 10 is a plate-shaped member, and the material of the base material 11 is not particularly limited insofar as the voids 11h through which a liquid can pass by capillary action are formed therein.

The base material 11 may be configured to include only the water-permeable material 12 (see FIG. 2(A)), may be configured to include the water-permeable material 12 and the water-impermeable material 13 (see FIG. 2(X)), may be configured to include a nanofiber layer 14 made of nanofibers of and the water-impermeable material 13 (see FIG. 2(Y)), or may be configured to include the water-permeable material 12, the water-impermeable material 13, and the nanofiber layer 14. The details of each material are described later.

The thickness of the base material 11 is not particularly limited insofar as it does not interfere the analysis of the liquid film Lf formed in the through-holes 10h. For example, the base material 11 is formed so that the thickness (the distance between the surface 11sa and the rear side 11sb of the base material 11 in FIG. 1(B)) thereof is about 0.01 mm to 10 mm.

Thickness of Base Material 11 in Absorption Spectrometry

In the absorption spectrometry, by increasing the optical path length in a cell, the absorption amount of the transmission light also increases, thereby increasing the sensitivity. Therefore, the concentration of the target component in the sample can be appropriately quantified.

Similarly, in the optical analysis chip 1, by increasing the liquid film length R of the liquid film Lf that corresponds to the optical path length, the target component in the sample L can be more appropriately quantified.

However, if the optical path length, i.e., the thickness-wise length of the through-hole region in the base material 11 in which the through-holes 10h are formed is excessively long, the transmitted light may be affected based on the material of the inner face of the through-holes 10h.

More specifically, in addition to light absorption based on the liquid film Lf spread inside the through-holes 10h, the absorption, scattering, or the like of the irradiation light L1 based on the material of the inner face of the through-holes 10h may also occur and it may cause a decrease in the amount of transmitted light other than the target component in the liquid film Lf, i.e., an adverse effect (decrease in sensitivity, decrease in measurement accuracy) on the measurement. For example, when the thickness of the base material 11 of the detection unit 10 in the through-hole region is larger than 10 mm, the measurement value may contain non-specific light absorption derived from the material of the base material 11 although it depends on the material of the base material 11.

On the other hand, for example, if the thickness of the through-hole region of the base material 11 is smaller than 0.01 mm, the liquid film length R of the liquid film Lf becomes short, and, as a result, the optical path length becomes excessively short, and the concentration of the target component in the sample L may not be appropriately measured. In addition, if the thickness of the through-hole region of the base material 11 of the detection unit 10 is smaller than the above value, the shape of the through-hole 10h is more likely to change.

Therefore, in view of the analysis method based on absorption spectrometry, the thickness of the base material 11 in the through-hole region of the detection unit 10 in the optical analysis chip 1 is, for example, not less than 0.01 mm and not more than 10 mm. Further, the lower limit of the thickness is preferably 0.05 mm or more and more preferably 0.1 mm or more. In addition, the upper limit of the thickness is preferably 5 mm or less, more preferably 3 mm or less, further preferably 1.5 mm or less.

Thickness of Base Material 11 in Fluorescence Spectrometry

Further, as in the absorption spectrometry, if the through-hole region of the base material 11 is formed with a large thickness in the method based on the fluorescence spectrometry, the liquid film length R of the liquid film Lf can be increased (i.e., the optical path length can be increased), but some influences may be caused based on the material of the inner face of the through-holes 10h.

More specifically, if the liquid film length R of the liquid film Lf is excessively long (i.e., the through-hole region of the base material 11 is excessively thick), the transmitted light may be affected based on the material of the inner face of the through-hole 10h. More specifically, in addition to the light absorption based on the liquid film Lf spread inside the through-holes 10h, some adverse effects (decrease in sensitivity, decrease in measurement accuracy) on the measurement similar to those in the absorption spectrometry described above may also occur.

On the other hand, if the through-hole region of the base material 11 is made excessively thin, the liquid film length R of the liquid film Lf decreases, and, as a result, the optical path length decreases. Consequently, appropriate fluorescence intensity cannot be obtained.

Therefore, in view of the analysis method based on the fluorescence spectrometry, it is preferable to prepare the optical analysis chip 1 such that the thickness of the through-hole region of the base material 11 of the detection unit 10 falls within the same range as in the case based on the absorption spectrometry.

Thickness of Base Material 11 in Color Tone Analysis

Similarly to the above-described absorption spectrometry and the fluorescence spectrometry, if the through-hole region of the base material 11 is formed with a large thickness in the method based on color tone analysis, the liquid film length R of the liquid film Lf can be increased (i.e., the optical path length can be increased). Then, such an increase in the liquid film length R can increase the color tone change amount based on the absorption or fluorescence derived from the target component in the liquid film Lf.

In contrast, if the thickness of the base material 11 in the through-hole region is excessively large, the transmitted light may be affected by light based on the material of the inner face of the through-hole 10h. More specifically, in addition to the light absorption based on the liquid film Lf spread inside the through-holes 10h, the light absorption based on the material of the inner face of the through-holes 10h may also occur. This results in some adverse effects (decrease in measurement accuracy) on the measurement, such as difficulties in visual confirmation of color tone change due to, for example, color change irrelevant to the concentration of the target component in liquid film Lf, or a decrease in color tone.

Therefore, in view of the analysis method based on the color tone analysis, it is desirable to prepare the optical analysis chip 1 such that the thickness of the through-hole region of the base material 11 of the detection unit 10 falls within the same range as in the case based on the absorption spectrometry.

Note that the above example describes a case where the thickness of the through-hole region of the base material 11 does not change due to swelling or the like of the material of the base material 11 when the sample L is supplied to the detection unit 10. More specifically, the sample L is supplied to the detection unit 10 so as to fill the entire through-holes 10h to thereby form a substantially uniform liquid films Lf in the plurality of through-holes 10h in the base material 11. At this time, the liquid film length R of each liquid film Lf is substantially the same as the penetration axis-wise length of the through-hole 10h in a dry state (i.e., the distance of the through-hole region of the base material 11 in the thickness-wise direction).

On the other hand, if the material of the base material 11 of the detection unit 10 absorbs the sample L and undergoes swelling or the like, the thickness-wise distance of the base material 11 becomes longer than that in the dry state after the sample L is supplied (see FIG. 6(D) in which swelling occurs in the direction of the arrow). At this time, as shown in FIG. 6(D), the penetration axis-wise length of the through-hole 10h increases as the base material 11 swells.

This results in an increase in the liquid film length R of the liquid film Lf; as a result, the optical path length also becomes longer than the penetration axis-wise length of the through-hole 10h in a state in which the base material 11 is dry. More specifically, even when the base material 11 is thin, it becomes possible to maintain an optical path length appropriate for analysis by using a material that is likely to undergo swelling or the like by the sample L as the material of the base material 11. Therefore, even when the base material 11 is thin, adjusting the material of the base material 11 enables to appropriately quantify the concentration of the target component in the sample L.

Further, the liquid film length R can be further increased, and thus the optical path length can also be further increased if the sample L is supplied in such a way that the liquid film surface Ls of the liquid film Lf has a convex meniscus shape due to the properties of the sample L.

Size and Shape of Base Material 11

The shape and the size of the base material 11 of the detection unit 10 is not particularly limited insofar as they do not interfere the analysis.

Examples of the shape of the base material 11 can use various shapes, such as a circular shape, a rectangular shape, a radial shape, a spiral shape, and the like. The size of the base material 11 may be any size that allows the detection unit 10 to be set in the spectrometer SM. For example, when the base material 11 has a square shape, the base material 11 can be formed so that one side thereof is approximately 0.1 cm to 5 cm. When the base material 11 has a circle shape, the base material 11 can be formed so that the diameter thereof is approximately 0.1 cm to 5 cm. However, the size may be appropriately adjusted based on the size of the stage of the spectrometer SM or the like.

Voids 11h in Base Material 11

As shown in FIG. 2, a plurality of voids 11h through which the liquid described above can pass by capillary action are formed inside the base material 11 of the detection unit 10.

The width of the voids 11h formed inside the base material 11 are not particularly limited insofar as a liquid can pass through therein by capillary action. For example, the width of each void 11h is approximately 0.1 μm to 2000 μm, more preferably 0.2 μm to 1000 μm or less, still more preferably 0.4 μm to 1000 μm or less, further preferably 1 μm to 1000 μm or less, and further more preferably 1 μm to 200 μm or less.

The plurality of voids 11h are formed in a mesh-like form in the base material 11. More specifically, in the base material 11, the plurality of voids 11*h* are formed in a mesh-like form so as to allow adjacent voids 11*h* to communicate with each other. In other words, a fine void network through which a liquid can pass by capillary action is formed in the base material 11.

Note that the proportion of the plurality of voids 11*h* in the base material 11 is not particularly limited.

Examples of the material of the base material 11 can use commercially available test filter paper made of cellulose fiber, which is the water-permeable material 12, filter cloth (felt), nonwoven fabric, and the like. When the base material 11 is formed from such a general material, a void ratio (the proportion of the volume of the voids 11*h* with respect to a certain volume of the filter paper or the like) is approximately 50% to 95%.

For example, when a filter paper is used as the base material 11, although it depends on the material, the void ratio is 60% to 95% for cellulose-based materials, 90% for silica-based materials, 50% to 85% for polytetrafluoroethylene (PTFE)-based materials, 80% to 90% for glass-based materials, and 80% to 90% for rayon-polyester-based nonwoven fabrics.

Through-Holes 10

As shown in FIGS. 1, 2, 4, and 5, a plurality of through-holes 10*h* that penetrate through the surface and the rear side of the base material 11 are formed in the base material 11 of the detection unit 10. As described above, this through-holes 10*h* are so formed as to be substantially orthogonal to the base material 11. More specifically, the through-holes 10*h* are formed so that the central axis CL is substantially orthogonal to the base material surface 11*s* of the base material 11.

Note that the expression "substantially orthogonal" means that the angle between the two members is 90 degrees±5 degrees in view of aspect ratio of the through-hole 10*h* (a ratio of the opening width of the through-hole 10*h* to the length of the through-hole 10*h*) in the present specification. In other words, in view of appropriate quantification of the target component in the sample L, the aspect ratio is adjusted to be not more than 11, which is the reciprocal of tan 5° (0.087), based on the incident angle of the irradiation light L1 incident on the liquid films Lf formed in the through-holes 10*h* and the attenuation rate of the transmitted light L2.

In optical analysis using the optical analysis chip 1, as described above, the irradiation light L1 is emitted so that the optical axis is substantially orthogonal to the base material surface 11*s* of the base material 11 of the detection unit 10 of the optical analysis chip 1 set in the spectrometer SM. This irradiation light L1 thus emitted is transmitted through the liquid films Lf formed in the through-holes 10*h* of the detection unit 10 to generate the transmitted light L2.

At this time, the liquid films Lf is formed so as to be substantially parallel to the optical axis of the irradiation light L1 since the through-holes 10*h* are formed so as to be substantially orthogonal to the base material surface 11*s* of the base material 11. Therefore, the transmitted light 2 having the optical axis substantially coaxial relative to the optical axis of the irradiation light L1 emitted to the liquid films Lf can be formed. Therefore, the concentration of the target component in the liquid film Lf can be appropriately quantified based on the transmitted light 2.

On the other hand, if the angle formed by the central axis CL of the through-hole 10*h* and the base material surface 11*s* of the base material 11 deviates from the above range, the obtained transmitted light L2 is often inappropriate.

Therefore, in view of appropriately quantifying the target component in the sample L by optical analysis using the optical analysis chip 1, it is desirable that the through-holes 10*h* are so formed as to be substantially orthogonal to the base material surface 11*s* of the base material 11.

Note that it is sufficient that the aforementioned angle between the two members falls within a range of 90 degrees±15 degrees when the target component in the sample L is qualified. In other words, in order to qualify the target component in the sample L, it is preferable to adjust the aspect ratio to be equal to or lower than 4, which is the reciprocal of tan 15° (0.268), based on the incident angle of the irradiation light L1 incident on the liquid films Lf formed in the through-holes 10*h* and the attenuation rate of the transmitted light L2.

Shape and Size of Through-Holes 10*h*

The size and the shape of this through-holes 10*h* are not particularly limited insofar as the through-holes 10*h* have a function of maintaining a state in which the liquid films Lf are formed by surface tension when the sample L is supplied into the through-holes 10*h*.

Shape of Through-Holes 10*h*

The through-holes 10*h* can be formed in various shapes such as a circular shape, an elliptical shape, a rectangular shape, a triangular shape, and the like.

For example, in a case where a non-circular shape, such as a triangular shape or an elliptical shape in which some portions of openings 10*h* a and 10*h* b have larger curvatures than those of the other portions, is selected as the shape of the through-holes 10*h*, the sample L moving through the voids 11*h* in the base material 11 tends to enter the through-holes 10*h* from a portion having a large curvature when the sample L reaches the inner wall surface of the through-hole 10*h*. More specifically, the sample L is likely to be efficiently spread into the through-holes 10*h* as compared with a case where the through-holes 10*h* have a circular shape when a non-circular shape is selected.

Size of Through-Holes 10*h*

The size of each through-hole 10*h* is not particularly limited insofar as the sample L supplied into the through-holes 10*h* can be kept in the state of liquid film Lf by surface tension.

For example, for a substantially circular through-hole 10*h*, the openings 10*ha* and 10*hb* preferably have a size of 50 μm or more. When the size of each through-hole 10*h* is smaller than 50 μm, the shape of the through-hole 10 tends to be less stable. On the other hand, the upper limit of the size of each through-hole 10*h* is not particularly limited insofar as the liquid film Lf described above can be formed although it depends on the viscosity of the sample L. For example, each through-hole 10*h* is formed to be smaller than 1000 μm. Accordingly, when the through-holes 10*h* have a substantially circular shape, the inner diameters of the openings 10*ha* and 10*hb* are 50 μm to 1000 μm, more preferably 50 μm to 600 μm, and further preferably 100 μm to 600 μm.

For example, in the elliptical through-holes 10*h*, the major axis (length in the major axis-wise direction) of the opening 10*ha* and 10*hb* is 50 μm to 1000 μm, and the minor axis (length in the minor axis-wise direction) orthogonal to the major axis is formed to be shorter than the major axis. More preferably, the major axis is 50 μm to 500 μm, and the minor axis is formed to be shorter than this major axis.

In addition, for example, when a filter paper made of cellulose fiber is used as the material of the base material 11, and elliptical through-holes 10*h* are formed in the base material 11 made of the cellulose fiber filter paper, the major axis of the opening 10ha/10hb of each through-hole 10h is 300 μm to 500 μm and the minor axis thereof is 250 μm to 300 μm.

In addition, for example, when a filter paper made of glass fiber is used as the material of the base material 11, and elliptical through-holes 10h are formed in the base material 11 made of the glass fiber filter paper, the major axis of the opening 10ha/10hb of each through-hole 10h is 350 μm to 600 μm and the minor axis thereof is 300 μm to 400 μm.

Further, for example, when a filter paper made of nitrocellulose fiber is used as the material of the base material 11, and elliptical through-holes 10h are formed in the base material 11 made of the nitrocellulose fiber filter paper, the major axis of the opening 10ha/10hb of each through-hole 10h is 250 μm to 500 μm and the minor axis thereof is 200 μm to 300 μm.

Number of Through-Holes 10h

A plurality of through-holes 10h can be formed in the through-hole region of the base material 11. The number of the through-holes 10h is not particularly limited.

For example, when the through-holes 10h have a substantially circular shape having an inner diameter of about 250 μm, or an elliptical shape having a major axis of about 300 μm and a minor axis of about 200 μm, 100 to 1000 through-holes 10h are formed per $cm^2$ in the through-hole region.

If a plurality of through-holes 10h are formed, a plurality of liquid films Lf are provided. Therefore, a larger amount of data for optical analysis can be also obtained. Therefore, the accuracy of quantitative determination of the target component in the sample L can be improved. In addition, by forming a plurality of through-holes 10h, it can be easily performed positioning of each liquid film Lf formed in the through-hole 10h in the measurement using the spectrometer SM. Therefore, the operability upon the analysis can be improved. Furthermore, by forming a plurality of through-holes 10h, it is possible to suppress variation in the quantitative values obtained from the measurement, thereby becoming possible to tolerate a wider range of variation in the shape of the through-holes 10h to some extent. Therefore, the through-holes 10h can be formed with inferior processing accuracy, thereby improving the productivity of the optical analysis chip.

On the other hand, when a single hole is formed as the through-hole 10h, there is an advantage that the cost of the base material 11 can be reduced and the processing time of the through-hole 10h can be reduced.

A method for forming the through-holes 10 is not particularly limited insofar as the through-holes 10 have the size and the shape described above.

Example of the method for forming the through-holes 10 can be used laser, mechanical punching, or etching using acids, bases, organic solvents, and the like. In particular, the through-holes 10h substantially orthogonal to the base material 11 can be more easily formed by the method using laser.

Optical Analysis Method Using Optical Analysis Chip 1

Next, optical analysis using the optical analysis chip 1 is described.

Quantitative Determination of Target Component in Sample L Based on Absorption Spectrometry Hereinbelow, firstly, a case where the target component in the sample L is quantified based on, among various optical analysis methods, absorption spectrometry, is described in detail as a representative example.

Note that the following describes, as a representative example, a case where the sample L is supplied to the through-holes 10h of the detection unit 10, and the amount of the sample L is sufficient to fill the entire through-hole 10h and the liquid film Lf is formed in the entire through-hole 10h (see FIG. 5).

In addition, the spectrometer SM and the optical analysis chip 1 described below are representative examples. Therefore, the spectrometer SM and the optical analysis chip 1 are not limited to the configuration as described below.

The spectrometer SM and the optical analysis chip 1 used in the following description are schematically explained below.

The spectrometer SM described below uses a light irradiation fiber disposed below the stage and a light receiving fiber provided above the opposite side relative to the communication hole.

The base material 11 of the detection unit 10 of the optical analysis chip 1 is made of a filter paper (having a predetermined void ratio), and are formed in a square shape, each side of which is approximately 10 mm. This base material 11 has a square through-hole region, each side of which is approximately 5 mm, which is provided inwardly from each side of the base material 11. This through-hole region is formed in the vicinity of the center of the base material 11 so that its center substantially coincides with the center of gravity of the base material 11. Further, in this through-hole region, 200 to 300 circular through-holes 10h are formed per $cm^2$. Each through-hole 10h has a diameter of approximately 100 μm to 1000 μm.

Spreading Sample L

First, the sample L is spread into each through-hole 10h of the detection unit 10.

As shown in FIGS. 4 and 10, a predetermined amount of the sample L is supplied dropwise to a part of the through-hole region or in the vicinity of the through-hole region in the base material 11 of the detection unit 10 of the optical analysis chip 1.

As shown in FIG. 4, the supplied sample L permeates into the base material 11 from a portion near the surface where the sample L was supplied dropwise. The sample L permeates from the surface to the inner part of the base material 11, and moves toward the inside of the through-holes 10h while moving through the voids 11h formed in the base material 11 by capillary action. The plurality of voids 11h are so formed as to allow a liquid to pass through therein by capillarity action. Therefore, the sample L automatically moves inside of the voids 11h to be away from the supply position when the sample L enters into the voids 11h.

Further, the plurality of voids 11h in the base material 11 are so formed as to communicate with the plurality of through-holes 10h. More specifically, an innumerable number of openings of the voids 11h are formed on the inner wall of the through-holes 10h. Thus, when the sample L moved inside the void 11h reaches one of the through-holes 10h, the sample L enters into the through-hole 10h from the voids 11h opening formed on the inner wall of the through-hole 10h. More specifically, the sample L is supplied into the one of the through-holes 10h (see FIG. 4(A)).

As it enters into the through-hole 10h, the sample L forms the liquid film Lf that blocks the through-hole 10h by surface tension of the through-hole 10h (see FIG. 4(B)). On the other hand, this through-hole 10h communicates with an adjacent through-hole 10h via the plurality of voids 11h (see FIG. 2). Therefore, the sample L that entered into one of the through-holes 10h moves to the adjacent through-hole 10h while maintaining a state in which the length of the liquid film Lf is substantially the same as the thickness (distance in the thickness-wise direction of the base material 11) of the through-hole region of the base material 11 (see FIGS. 4(B) to 4(D)).

As such a phenomenon continuously occurs, the sample L is substantially uniformly spread to the plurality of through-holes 10*h* formed in the through-hole region of the base material 11, and a substantially uniform liquid film Lf is formed in each through-hole 10*h* (see FIG. 5).

Moreover, the length of the liquid film Lf can be substantially identical to the distance of the line of the penetration axis-wise direction of the through-hole 10*h* (i.e., the thickness of the through-region of the base material 11) since the liquid film Lf formed in the through-holes 10*h* is formed with its surface and rear side substantially flat with respect to the surface of the through-hole region.

Therefore, by supplying the sample L dropwise to a part of the through-hole region or in the vicinity of the through-hole region of the base material 11 of the detection unit 10 of the optical analysis chip 1, the sample L can be spread into the plurality of through-holes 10*h* while automatically moving inside the voids 11*h* formed in the base material 11 of the detection unit 10 by capillary action, thereby forming a uniform liquid film Lf in each through-hole 10*h* (see FIGS. 4 and 5). More specifically, a plurality of liquid films Lf having a uniform optical path length can be formed in the through-hole region of the base material 11 of the detection unit 10 (see the enlarged view of FIG. 5).

Measurement and Quantitative Determination

The optical analysis chip 1 in which the predetermined liquid films Lf are formed in the plurality of through-holes 10*h* as described above is set on the stage of the spectrometer SM (see FIG. 9).

At this time, the optical analysis chip 1 is set such that the through-hole region formed in the base material 11 of the detection unit 10 of the optical analysis chip 1 is positioned on the opening of the communication hole of the stage. At this time, since the through-holes 10*h* are so formed as to be orthogonal to the base material 11, the liquid films Lf can be disposed in parallel with the optical axis of the irradiation light L1.

In this state, by operating the light source, the irradiation light L1 is emitted from the light irradiation fiber to the through-hole region of the detection unit 10 of the optical analysis chip 1.

This irradiation light L1 passes straight through the liquid film Lf formed in the through-hole 10*h* from the lower surface toward the upper surface of the liquid film Lf (see FIG. 5). At this time, if a material that reacts with the irradiation light L1 is present in the liquid film Lf, the irradiation light L1 incident on the liquid film Lf and the transmitted light L2 transmitted through the liquid film Lf have different light components.

This transmitted light L2 transmitted through the liquid film Lf is received by a light receiving surface of a light receiving fiber provided above the stage of the spectrometer SM. This transmitted light L2 received by the light receiving fiber is transmitted to the analyzing means.

The analyzing means converts the transmitted light L2 transmitted from the light receiving fiber into data signals. Then, the concentration of the target component in the sample L is calculated (i.e., quantified) based on the data signals obtained by the conversion.

As described above, first, the sample L is supplied to the base material 11 of the detection unit 10 of the optical analysis chip 1 to form the liquid film Lf in each through-hole 10*h* of the detection unit 10. Each liquid film Lf is held within each through-hole 10*h* in substantially the same state.

Then, by setting the detection unit 10 in the spectrometer SM, the concentration of the target component in the sample L can be quantified based on the transmitted light L2 obtained from the liquid film Lf. More specifically, in the detection unit 10, a sample having an optical path length necessary for optical analysis can be formed in a uniform state.

Therefore, the detection unit 10 of the optical analysis chip 1 exhibits a function similar to that of a transparent cell made of quartz, glass, or the like, used in previously-known optical analysis methods. Moreover, although the size of each through-hole 10*h* in which the sample L is supplied is small (for example, about 50 μm), the target component in the sample L can be accurately quantified based on the optical analysis method.

Note that the concentration can be calculated based on a general calculation method according to the absorption spectrometry. For example, the concentration of the target component in the sample may be calculated using a calibration curve method or a standard addition method based on the relationship between absorbance and concentration, or may be calculated by an internal standard method using an internal standard substance, which is added to the sample.

In addition, in the measurement of the sample L, it is desirable to perform a blank measurement using the same optical analysis chip 1 in advance. More specifically, by preparing a blank sample that does not contain the target component and performing analysis of the blank sample in a manner similar to the analysis of the sample L using the same optical analysis chip 1, it is possible to suppress data variation such as the correction of background light absorption caused by the optical analysis chip 1. As a result, it is possible to obtain an advantage that the accuracy of quantitative analysis of the target component can be further improved.

In addition, by simply supplying the sample L to a part of the through-hole region provided in the base material 11 of the detection unit 10 or the periphery thereof, the sample can be automatically and uniformly supplied into the plurality of through-holes 10*h*. In other words, the operability of the analysis can be improved since a complicated operation to ensure uniform supply of the sample is not necessary. Moreover, averaging or the like of the data of each liquid film Lf can be more easily performed, and therefore the analysis accuracy can be further improved since the uniform liquid films Lf can be formed.

Furthermore, the sample can be moved inside the base material 11 of the detection unit 10 even when the optical analysis chip 1 is not kept horizontal (for example, even if the base material 11 of the detection unit 10 is fixed in a vertical direction) since the supplied sample L moves inside the base material 11 of the detection unit 10 by capillary action and is held within the through-holes 10*h* by surface tension. Therefore, regardless of the disposition state of the optical analysis chip 1, homogeneous liquid films Lf can be formed in the plurality of through-holes 10*h* formed in the base material 11 of the detection unit 10.

Further, the sample L may be supplied dropwise directly to a part or all of the through-hole region as described above, or may be supplied to a non-through-hole region in the vicinity of the through-hole region. More specifically, with the detection unit 10 of the optical analysis chip 1 configured as described above, it is possible to appropriately spread the sample L into the plurality of through-holes 10*h* regardless of the supply position of the sample L.

Quantitative Determination of Target Component in Sample L Based on Color Tone Analysis Next, a case where the target component in the sample L is quantified using the color tone analysis, which is one of the optical analysis methods, is described in detail.

First, an outline of color tone analysis using the optical analysis chip 1 is described.

As described above, the optical analysis chip 1 is set on the stage of the spectrometer SM, and the detection unit 10 is irradiated with the irradiation light L1 emitted from the light irradiation fiber. As a result, the color tone of the liquid films Lf formed in the plurality of through-holes 10h changes depending on the concentration of the target component in the sample L. The color tone analysis of the present embodiment is a technique of quantifying the target component in the sample L based on this change of the color tone of this changed liquid films Lf.

The color tone analysis is more specifically explained below.

The base end of the optical microscope is connected to the analyzing means to enable conversion of the observed image of the liquid films Lf formed in the through-holes 10h to data, as well as transmission of the data to the analyzing means.

The analyzing means calculates the concentration of the target component in the sample based on the image data. More specifically, the analyzing means is capable of calculating the concentration of the target component in the sample L by analyzing coloring based on the image data using a color space (a color system such as RGB or L*A*B* (Lab color space)).

More specifically, since the absorption wavelength and the absorption amount of the target component present in the sample (i.e., in the liquid film Lf) and its concentration are specific to the component, it is possible to identify and quantify the substance in the sample from the color tone based on the image data observed by an optical microscope (see FIG. 14).

Since optical microscopes have an option of flexible magnification adjustment, it is possible to analyze the color tone of a single liquid film Lf formed in one of the plurality of through-holes 10h of the base material 11 of the detection unit 10. In this case, it is possible to identify and quantify substances in the sample regardless of the diameter of the through-holes 10h.

On the other hand, the color tones of the liquid films Lf formed in the plurality of through-holes 10h may be summed and then averaged the values. By averaging the data, the quantitativity and reproducibility of the target component in the sample can be improved. More specifically, by using the optical analysis chip 1, the concentration of the target component in the sample can be appropriately quantified based on the color tone analysis even when a small amount of sample is used.

Note that the light emitted from the light irradiation fiber may have a single wavelength or may be white light. When measurement of a limited kind of target component is assumed, monochromatic light (for example, LED) in the vicinity of the maximum absorption wavelength of the target component may be emitted. When a plurality of target components are simultaneously measured or when time-resolved measurement for dynamically observing a reaction of the target component is performed, white light having a wide wavelength may be used.

In addition, the calculation of the concentration of the target component in the sample can be performed, for example, by converting the color tone to a numerical value and expressing it in a biaxial plane or a triaxial space in the form of an XY color system or a Lab color system, measuring a solution having a known concentration, and calculating the concentration of the target component in the sample based on the numerical correlation between the concentration and the color tone.

Furthermore, as described above, another possible configuration may be such that the detection unit 10 of the optical analysis chip 1 is provided with a cover member 30 (described later) on the surface and/or the back side of the base material 11, as well as a material that reacts with the target component in the sample to generate a color or the like when the liquid film Lf is formed in the through-hole 10h. For example, by placing a reaction reagent that reacts with the target component in the sample to generate a color or the like on an inner surface (i.e., a plane positioned on the surface or the back side of the base material 11) of the cover member 30 (described later), it is possible to react the reagent according to the concentration or the like of the target component in the sample.

In this manner, even if the concentration of the target component is low, the target component in the sample becomes possible to be quantified based on changes in color tone such as coloration. Moreover, even if the target component in the sample does not react with the irradiation light, the use of the reaction reagent enables calculation of the concentration of the target component. This improves the flexibility in the analysis.

Details of Base Material 11

As described above, various configurations may be employed to comprise the base material 11, and examples include a configuration including only the water-permeable material 12, a configuration including the water-permeable material 12 and the water-impermeable material 13, a configuration including the nanofiber layer 14 and the water-impermeable material 13, and a configuration including all of them.

Hereinafter, the materials (the water-permeable material 12, the water-impermeable material 13, and the nanofiber layer 14) of the base material 11 of the detection unit 10 are more specifically described.

Water-Permeable Material 12

As shown in FIG. 2(A), the water-permeable material 12 is a fiber assembly in which thin fibers f are bundled. The water-permeable material 12 is not particularly limited insofar as it has a property of allowing a liquid such as water to permeate inside thereof or flow along the surface thereof.

Further, as shown in FIG. 2(A), the base material 11 may have a structure constituted only of the water-permeable material 12 so that it has a certain degree of void ratio. Example of such a structure includes commercially available filter paper described later.

The following materials can be employed as the water-permeable material 12.

Examples of the fibers constituting the water-permeable material 12 include natural fibers such as cellulose fibers, fibers, hemp fibers, and pulp fibers; synthetic resin fibers (chemical fibers) made of a synthetic resin-based material (e.g., polyester, nylon, rayon, acrylic, polypropylene, polyethylene, polyvinyl alcohol, nitrocellulose, or carbon); metallic fibers (metal fibers) made of steel wool, copper, silver or the like; and fibers f made of an inorganic compound-based material such as oxides of silicon or titanium, hydroxides of magnesium or the like, carbonates of calcium or the like, and sulfates of barium or the like. Of course, a suitable mixture of two or more kinds of those described above can be also used.

As shown in FIG. 2(A), the water-permeable material 12 is an assembly in which a plurality of the fibers f are bundled. Further, in the water-permeable material 12, a minute gap 12h having a width narrower than that of the void 11h of the base material 11 is formed between the fibers f. This gap 12h, for example, has a width of about several μm to several tens of μm. Therefore, once a liquid such as water comes into contact with the water-permeable material 12, the liquid can permeate into the minute gap 12h between the fibers f. Once it enters the gaps between the fibers f, the liquid automatically moves inside the gap 12h by surface tension or similar interaction between the liquid and the surface of the fibers f having the gap 12h. More specifically, the water-permeable material 12 has a function of causing the sample to permeate inside thereof when the sample comes into contact with it and moving the sample inside the gap 12h by capillary action.

The following describes a case of base material 11 constituted only of a plurality of water-permeable materials 12 described above so that it has a structure having a predetermined void ratio. In this case, the mesh-like voids 11h of the base material 11 are formed of the plurality of voids 11h formed between the water-permeable materials 12 and a plurality of gaps 12h in the water-permeable materials 12. Examples of the material that can be used as the base material 11 having such a structure include, but not limited to, the above-described commercially available filter paper (for example, the filter paper described in Examples below), filter cloth (felt), and nonwoven fabric.

Further, the water-permeable material 12 may contain a fine inorganic pigment or the like that is added intentionally or contained as impurities when the water-permeable material 12 itself is manufactured. This is because such fine impurities do not contribute to the formation of a flow path in which the sample L moves.

Water-Impermeable Material 13

The water-impermeable material 13 has a property that does not allow a liquid such as water to permeate inside thereof.

As shown in FIG. 2(X), the water-impermeable material 13 is disposed between the plurality of water-permeable materials 12 in the base material 11.

Examples of the material of the water-impermeable material 13 can include polyethylene terephthalate (PET), synthetic resins such as polyethylene (PE) or polypropylene (PP), carbon, glass, silica, metal, calcium carbonate, and silicon dioxide. In particular, when an animal body fluid such as blood is used as a sample, it is preferable to use the water-impermeable material 13 made of PET having low reactivity with such a body fluid.

The shape of the water-impermeable material 13 is not particularly limited, and the water-impermeable material 13 can be made of any materials of various shapes, having a lump shape, a spherical shape, and a short fibrous shape. Alternatively, the water-impermeable material 13 may be formed of a plurality of entangled fibrous materials.

When the water-impermeable material 13 is made of a fibrous material, the size thereof is not particularly limited. For example, the fibrous water-impermeable material 13 can use a fiber diameter of about 10 μm to 500 μm and a fiber length of about 20 μm to 5 mm, or a fiber diameter of about 50 μm to 100 μm and a fiber length of about 50 μm to 1 mm.

The base material 11 has a structure in which the fibrous water-impermeable material 13 and the water-permeable material 12 described above are provided. In this case, the voids 11h having a predetermined void width can be easily formed in the base material 11. Further, the mesh-like voids 11h of the base material 11 are formed by the voids 11h between the plurality of water-permeable materials 12, the voids 11h between the water-permeable material 12 and the water-impermeable material 13, the voids 11h between the plurality of water-impermeable materials 13, and the gaps 12h in the water-permeable material 12. Therefore, more complicated mesh-like voids 11h are formed in the base material 11.

In particular, it has the following advantages when the base material 11 has a structure providing the water-impermeable material 13 and the water-permeable material 12.

First, the base material 11 is provided with the water-impermeable material 13. This water-impermeable material 13 is disposed between the plurality of water-permeable materials 12 in the base material 11. Moreover, the plurality of water-impermeable materials 13 are present non-uniformly (randomly) in the base material 11.

Therefore, a plurality of mesh-like voids 11h are formed inside the base material 11. More specifically, a mesh-like void network is formed inside the base material 11. Further, this mesh-like voids 11h are formed such that the change in the width of each void 11h (i.e., the flow path width) in which the sample L flows increases (changes non-uniformly) along the direction (the flow path direction) in which the sample L flows.

Then, the supplied sample L permeates into the base material 11 and moves toward the through-holes 10h while moving inside the plurality of mesh-like voids 11 when the sample L is supplied dropwise near the through-hole region of the base material 11. Then, impurities are separated and removed while the sample L moves inside the mesh-like voids 11h. More specifically, the base material 11 of the detection unit 10 of the optical analysis chip 1 has a filter function of separating and removing impurities and the like contained in the sample L.

Then, the base material 11 is also provided with the water-permeable material 12. This water-permeable material 12 therein has a plurality of gaps 12h in which the sample L can moves by capillary action.

Therefore, by providing the water-impermeable material 13 and the water-permeable material 12 in the base material 11, it is possible to make the void network formed inside the base material 11 more complicated. More specifically, by providing the water-permeable material 12 in the base material 11 of the detection unit 10 of the optical analysis chip 1, the base material 11 becomes possible to exhibit a higher filter function.

As described above, the filter function of the base material 11 of the analysis chip 1 is the smallest in the case where the base material 11 is formed only of the water-permeable material 12, and increases in the ascending order from the case where the base material 11 is formed of the water-permeable material 12 and the water-impermeable material 13 to the case where the base material 11 is formed of the nanofiber layer 14 (described later) and the water-impermeable material 13, which is the highest. In other words, in the base material 11, the non-uniformity of the voids 11h formed therein tends to increase as the filter function increases.

Therefore, the target component of the sample L becomes possible to be appropriately quantified by appropriately adjusting the structure of the base material 11 of the detection unit 10 according to the amount of impurities in the sample L when the target component in the sample L is quantified. More specifically, in analysis of a sample L containing a large amount of impurities, it is more preferable to use the base material 11 made of the water-permeable material 12 and the water-impermeable material 13 or the base material 11 made of the nanofiber layer 14 (described later) and the water-impermeable material 13, rather than using the base material 11 made only of the water-permeable material 12.

Blending Ratio of Water-Permeable Material 12 and Water-Impermeable Material 13

The blending ratio of the water-permeable material 12 and the water-impermeable material 13 constituting the base material 11 is not particularly limited insofar as the filter function described above can be exhibited.

For example, the water-permeable material 12 and the water-impermeable material 13 can be blended such that the blending ratio (mass ratio) of the water-permeable material 12 to the water-impermeable material 13 is 1:9 to 9:1.

Further, the base material 11 having a configuration in which the water-impermeable material 13 is disposed between the water-permeable materials 12 or the nanofiber layers 14 was described in the above example; however, the base material 11 may be formed of only using the water-impermeable material 13. More specifically, the base material 11 may be formed of using a plurality of fibrous water-impermeable materials 13 that are entangled to form a filter paper-like structure.

Nanofiber Layer 14 and Water-Impermeable Material 13

Next, a case where the base material 11 includes the nanofiber layer 14 and the water-impermeable material 13 is specifically described.

As shown in FIG. 2(Y), the base material 11 includes a plurality of nanofiber layers 14 and the plurality of water-impermeable includes materials 13, and thus has a structure in which the plurality of nanofiber layers 14, and the plurality of water-impermeable materials 13 disposed between the plurality of nanofiber layers 14 are provided therein. As described later, the plurality of nanofiber layers 14 are formed of a plurality of holes penetrating through the surface and the rear side thereof due to the influence of the water-impermeable materials 13.

As shown in FIG. 2(Y), in the base material 11, a plurality of mesh-like voids 11$h$ (the mesh-like void network) are formed between adjacent nanofiber layers 14, between the nanofiber layer 14 and the water-impermeable material 13, and between adjacent water-impermeable materials 13.

The plurality of water-impermeable materials 13 are disposed while being bundled by the plurality of nanofiber layers 14. With this structure in which the plurality of water-impermeable materials 13 are bundled, the distance between the adjacent water-impermeable materials 13 can be reduced. Thus, the width (flow path width) of each void 11$h$ between the adjacent water-impermeable materials 13 can be reduced.

Therefore, by providing the nanofiber layers 14 and the water impermeable materials 13 in the base material 11 of the detection unit 10, making the flow path width of the plurality of voids 11$h$ formed therein can be more complicated. That is, making the void network formed in the base material 11 can be further more complicated.

Therefore, by providing the nanofiber layers 14 and the water impermeable materials 13 in the base material 11 of the detection unit 10 of the optical analysis chip 1, the base material 11 becomes possible to exhibit a superior filter function.

The nanofiber layer 14 has a membrane form and is made of nanofibers nf that are fine fibers. More specifically, the nanofiber layer 14 is an assembly in which a plurality of nanofibers nf are entangled and aggregated.

Examples of the nanofibers nf constituting the nanofiber layer 14 can be made of a synthetic resin or a natural material.

Example of natural materials can include cellulose nanofibers nf. Since the cellulose nanofibers nf have a large number of hydroxyl groups on the surface thereof, the hydrophilicity of the cellulose nanofibers nf is higher than that of general synthetic resin nanofibers nf in which hydrophilic functional groups are chemically bonded. The cellulose nanofibers nf therefore easily get wet with water.

Accordingly, by using this property to form the base material 11 from the nanofiber layer 14 (may also be simply referred to as a CNF layer 14) used the cellulose nanofibers nf, the capillary action generated in the voids 11$h$ formed between a plurality of CNF layers 14 can be further improved.

Therefore, the base material 11 including the plurality of CNF layers 14 enables to obtain an advantage that the movement of the sample L inside the base material 11 becomes smoother. In other words, the base material 11 including the plurality of CNF layers 14 exerts a high water absorption function while exerting an excellent filter function.

Note that the size of the cellulose nanofibers nf is not particularly limited.

For example, fibers having an average fiber diameter of about 1 to 100 nm or an average fiber length of about 100 nm to 1 μm can be used.

The blending ratio of the nanofibers nf as a raw material of the nanofiber layer 14 constituting the base material 11 to the water-impermeable material 13 is not particularly limited.

For example, the cellulose nanofibers nf and the water-impermeable material 13 can be mixed such that the mass ratio of the cellulose nanofibers nf to the water-impermeable material 13 is 1:9 to 9:1.

Further, a nanofiber layer made of the nanofibers nf generally has a property that does not easily allow a liquid such as water to permeate. If the base material is formed only of such a nanofiber layer, the liquid is repelled on the surface of the base material and cannot permeate into the base material.

On the other hand, the base material 11 of the detection unit 10 of the analysis chip 1 is formed of a mixture of the nanofibers nf as a raw material of the nanofiber layer 14 and the water-impermeable material 13. Therefore, a plurality of fine holes penetrating through the surface and the rear side thereof are formed in the nanofiber layer 14 disposed inside the base material 11 and on the surface of the base material 11.

Therefore, even if the base material 11 of the detection unit 10 is configured to have the nanofiber layer 14, the supplied sample L permeates into the base material 11 without being repelled by the nanofiber layer 14 positioned on the outermost layer (i.e., the surface of the base material 11) when the sample L is supplied dropwise to the surface of the base material 11 during the supply operation of the sample L.

In addition, the material of the base material 11 is not limited to these materials although the above example describes the structure in which the base material 11 of the detection unit 10 has the water-permeable material 12, the water-impermeable material 13, and the nanofiber layer 14. Various additives and the like may be included insofar as the base material 11 has the structure with the voids 11$h$ described above. Examples of the materials include, but not limited to, a material that adsorbs impurities in the sample, a pigment having an attachment/detachment function, and a material that controls wettability of the base material.

Flow Path Unit 20

As shown in FIGS. 1 and 3, the optical analysis chip 1 may include a flow path unit 20 connected to the base material 11 of the detection unit 10.

This flow path unit 20 includes a flow path base material 21 that allows a liquid to permeate. More specifically, the flow path unit 20 is so formed as to move the sample L supplied from a sample L supply portion to the base material 11 through the flow path base material 21 when the sample L is supplied to a portion on the base end side of the flow path base material 21 (i.e., a portion distant from the junction with the base material 11, see FIG. 4) in a state in which the top end portion of the flow path base material 21 is connected to the base material 11. Further, this flow path base material 21 of the flow path unit 20 has a filter function similar to that of the base material 11 of the detection unit 10.

Therefore, by providing the optical analysis chip 1 with the flow path unit 20, impurities (contaminants) contained in the sample L can be removed by the filter function of the flow path base material 21 of the flow path unit 20. More specifically, due to the filter effect of the flow path base material 21, a plurality of components contained in the sample L are appropriately screened by size. More specifically, the supplied sample L can be moved to the base material 11 of the detection unit 10 while the components contained in the sample L are separated into the target component and components other than the target component (non-target components), and the non-target components are removed. Then, the sample L containing less contaminants (i.e., purified sample L) can be spread into the plurality of through-holes 10h of the detection unit 10.

Therefore, with this optical analysis chip 1 provided with the flow path unit 20, the amount of impurities contained in the liquid film Lf can be reduced, thereby becoming capable of quantitative determination of the target component in the sample L with higher accuracy. In other words, it may be appropriately used either the optical analysis chip 1 providing the flow path unit 20 or the optical analysis chip 1 providing only the detection unit 10 depending on the state of impurities contained in the sample L.

Further, the supplying position of the sample L may be adjusted depending on the amount of impurities in the sample L even if the optical analysis chip 1 has the structure including the flow path unit 20. For example, the sample L is supplied in the vicinity of the through-hole region in the detection unit 10 if the sample L contains a small amount of impurities. The sample L is supplied to a portion separated from the through-hole region in the detection unit 10 or to a portion of the flow path unit 20 near the through-hole region of the detection unit 10 if the amount of impurities in the sample L is moderate. The sample L is supplied dropwise to a portion of the flow path unit 20 separated from the through-hole region of the detection unit 10 if the sample L contains a large amount of impurities.

Further, the detection material described above may be supported or held in a portion of the flow path unit 20 where the sample L passes. More specifically, in the flow path unit 20, a reaction field is provided between the sample L supplying position in the flow path unit 20 and the through-hole region of the detection unit 10. In this reaction field, a detection material such as the reaction reagent that binds to the target component in the sample L is supported by the material (for example, the water-permeable material 22) constituting the flow path base material 21, or is held between the materials. A method for supporting or holding the detection material is not particularly limited. For example, the detection material can be held in the reaction field by, for example, applying the detection material to the reaction field, followed by drying.

Structure of Flow Path Base Material 21

Hereinafter, the structure of the flow path unit 20 is specifically described.

The flow path base material 21 of the flow path unit 20 of the optical analysis chip 1 may have a structure similar to that of the base material 11 of the detection unit 10 described above. More specifically, the flow path base material 21 of the flow path unit 20 may have any structure having therein a plurality of voids 21h that allow a liquid to pass through by capillary action.

The material of the flow path base material 21 is not particularly limited insofar as it has the structure described above.

For example, a material similar to the material of the base material 11 of the detection unit 10 to which the flow path unit 20 is connected may be used for the flow path base material 21. A different material may also be used. When the same material as that of the base material 11 is used, the movement state of the sample supplied to the flow path base material 21 of the flow path unit 20 can be predictable to some extent.

For example, as shown in FIG. 3, examples of the material of the flow path base material 21 of the flow path unit 20 can include the water-permeable material 22 similar to the water-permeable material 12 of the base material 11, the water-impermeable material 23 similar to the water-impermeable material 13 of the base material 11, and the nanofiber layer 24 made of nanofibers of similar to those of the nanofiber layer 14 of the base material 11.

For example, FIG. 3(B) shows a structure in which the flow path base material 21 of the flow path unit 20 uses the same material as that of the base material 11 of the detection unit 10 and has the same structure as that of the base material 11 of the detection unit 10. More specifically, the flow path base material 21 of the flow path unit 20 and the base material 11 structure of the detection unit 10 are formed as a continuous structure. In other words, the base material 11 of the detection unit 10 and the flow path base material 21 of the flow path unit 20 are integrally formed. In this structure, the structural difference at the junction between these members can be reduced; therefore, it is possible to more smoothly move the sample L from the flow path unit 20 to the detection unit 10. In addition, such integral formation with the detection unit 10 using the same material as that of the detection unit 10 increases productivity.

In addition, for example, FIG. 3(X) shows a structure in which the flow path base material 21 of the flow path unit 20 includes a plurality of water-permeable materials 22 and a plurality of water-impermeable materials 23, and the plurality of water-impermeable materials 23 are disposed between the plurality of water-permeable materials 22. In this case, as in the base material 11 of the detection unit 10, it is possible to form further complicated mesh-like voids 21h, compared with a structure formed only of the water-permeable material 22. More specifically, a more complicated void network can be formed in the flow path base material 21 of the flow path unit 20, as in the base material 11 of the detection unit 10.

In particular, as shown in FIG. 3(X), by incorporating fibrous water-impermeable material 23 in the flow path base material 21, the plurality of water-impermeable materials 23 are oriented in the same direction. More specifically, this flow path base material 21 can have a structure in which the plurality of fibrous water-impermeable materials 23 are arranged along the same direction. For example, the flow path base material 21 is formed in a strip shape, and the longitudinal top end of the flow path base material 21 is connected to the base material 11 of the detection unit 10. In this case, the optical analysis chip 1 can have a structure in which the plurality of fibrous water-impermeable materials 23 are arranged from the base end to the top end (the junction between the flow path base material 21 and the base material 11) of the flow path base material 21 of the flow path unit 20. More specifically, the plurality of fibrous water-impermeable materials 23 are arranged along the direction toward the detection unit 10. Therefore, the sample L is more smoothly moved toward the detection unit 10 along the plurality of water-impermeable materials 23 when the sample L is supplied to the flow path base material 21 of the flow path unit 20 of this optical analysis chip 1.

Moreover, the plurality of fine void networks as described above are formed in the flow path base material 21. Therefore, the sample L automatically and more smoothly moves along the fibrous water-impermeable material 23 from the base end toward the top end (in the direction toward the junction between the flow path unit 20 and the detection unit 10) of the flow path base material 21 when the sample L is supplied to the flow path base material 21 of the flow path unit 20 of this optical analysis chip 1.

Although the structure in which the fibrous water-impermeable materials 23 are arranged along the longitudinal direction of the flow path base material 21 was described above, it is not limited to the structure.

For example, a structure in which the fibrous water-impermeable materials 23 intersect the longitudinal direction of the flow path base material 21 may be employed. More specifically, a plurality of water-impermeable materials 23 are arranged so as to intersect the direction toward the detection unit 10. In other words, a structure in which the plurality of water-impermeable materials 23 are arranged so that the axis-wise direction thereof is oblique to the detection unit 10 may be employed. In this case, it is possible to make the feed of the sample L slower than that in the case where the water-impermeable materials 23 are arranged right along the longitudinal direction of the flow path base material 21. In this case, the time for retaining the sample L in the reaction field described above can be increased, thereby giving sufficient time to bond the detection material and the sample L. This provides an advantage that the sensitivity of the target component in the sample L can be further improved.

As described above, in the flow path base material 21, it is sufficient that the fibrous water-impermeable materials 23 are arranged so as to intersect with the longitudinal direction of the flow path base material 21 to thereby slow down the feeding speed of the sample L. For example, the fibrous water-impermeable materials 23 can be arranged so as to intersect with the longitudinal direction of the flow path base material 21 at an angle of 10 degrees or more, more preferably 70 degrees or more, and still more preferably substantially orthogonal.

In addition, as shown in FIG. 3(Y), the flow path base material 21 can have a structure having a plurality of nanofiber layers 24, and a plurality of fibrous water-impermeable materials 23 that are arranged between the nanofiber layers 24. In this case, this flow path base material 21 has a state in which the plurality of fibrous water-impermeable materials 23 are oriented (arranged) toward the junction between the flow path unit 20 and the detection unit 10.

Further, the plurality of fibrous water-impermeable materials 23 arranged in the same direction are bundled together by the nanofiber layer 24 (see FIG. 3(Y)). Therefore, the sample L more smoothly can move toward the detection unit 10 along the bundled plurality of fibrous water-impermeable materials 23 and the nanofiber layer 24 when the sample L is supplied to the flow path base material 21 of the flow path unit 20 of this optical analysis chip 1.

In addition, the mechanical strength of the flow path base material 21 of the flow path unit 20 can be improved since the plurality of fibrous water-impermeable materials 23 are bundled by the nanofiber layer 24. This provides an advantage that the flexibility in use can be improved.

Size and Shape of Flow Path Base Material 21

Note that the size, shape, and the like of the flow path base material 21 of the flow path unit 20 are not particularly limited.

For example, the flow path base material 21 of the flow path unit 20 can be formed in a rectangular plate shape in a plan view, and the edge of the short side of the flow path base material 21 can be connected to the base material 11 of the detection unit 10. In this case, it is possible to efficiently move the sample to the detection unit 10 if the width of the short side of the flow path base material 21 is equal to or slightly smaller than the edge width of the base material 11 in the other end of connection.

In addition, the flow path unit 20 can be formed in various shapes, such as an I-shape, a Y-shape, a cross shape, or a radial shape. For example, a structure in which the detection unit 10 is connected to each of the tips of two branched Y-shape flow path or each of the tips of a cross-shaped flow path enables simultaneous measurement of a plurality of target components in the sample L.

Further, for example, the detection unit 10 is configured to be connected to the base end of the flow path unit 20 formed in a Y-shape. Then, samples L having different properties are added to the two tips of the branched flow paths. As a result, the resulting mixture can be transported to the detection unit 10 while the samples L having different properties are mixed at the junction.

The length of the flow path base material 21 of the flow path unit 20 is not particularly limited, and may be appropriately adjusted according to the amount of the sample L, the size of the stage of the spectrometer SM, and the like. For example, in the case of the flow path base material 21 having a rectangular plate shape in a plan view with its short side connected to the base material 11, the long sides thereof can be formed to be approximately 10 mm to 50 mm.

Water-Impermeable Region 11c

Figure 7A:
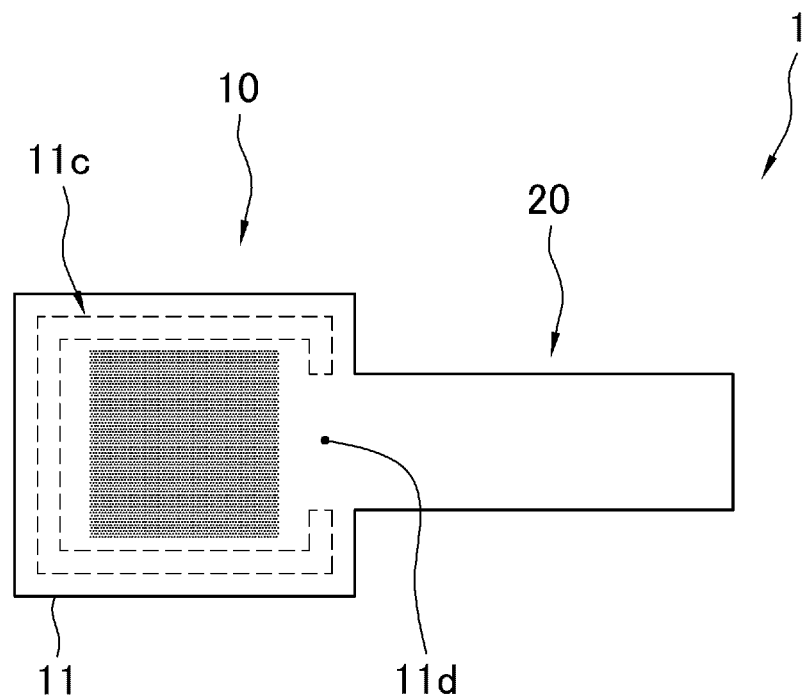
FIG. 7 is a schematic explanatory view illustrating a water-impermeable region 11$c$ of the detection unit 10 of the optical analysis chip 1 of the present embodiment.
Figure 7B:
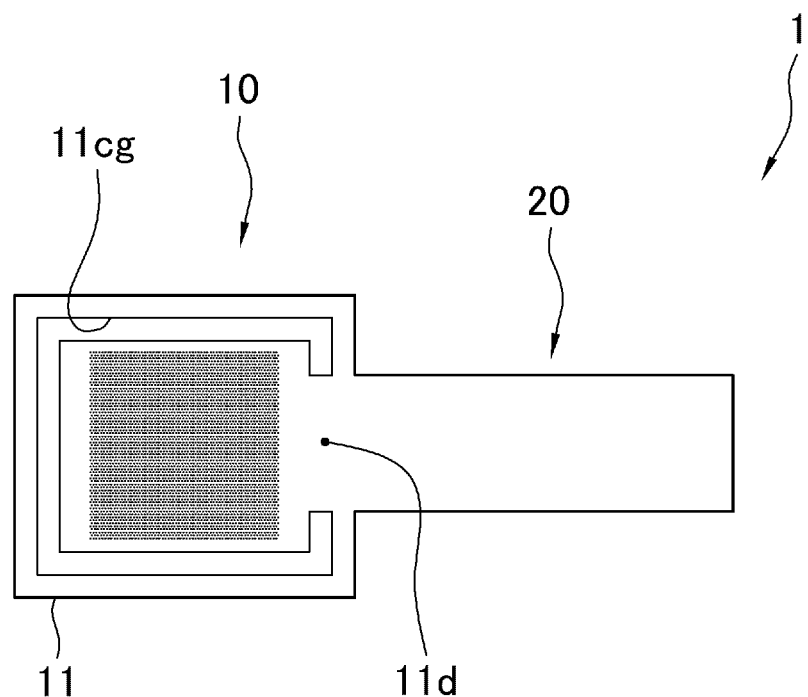

As shown in FIG. 7, in the base material 11 of the detection unit 10 of the optical analysis chip 1, a water-impermeable region 11c that does not allow a liquid to pass through may be provided so as to surround the peripheral portion of the through-hole region forming and providing the plurality of through-holes 10h.

More specifically, the water-impermeable region 11c is provided along the peripheral portion of the through-hole region so as to cover the peripheries of the gaps 12h of the water-permeable material 12 and the voids 11h formed on the outer end surface of the peripheral portion of the through-hole region so as to prevent them from being exposed to the outside. More specifically, the peripheral portion of the through-hole region is shielded from the outside by the water-impermeable region 11c.

If the base material 11 of the detection unit 10 of the optical analysis chip 1 has the water-impermeable region 11c configured as described above, when the sample is spread into the plurality of through-holes 10*h*, the movement of the sample from the inside of the through-hole 10*h* located in the vicinity of the inner side of the peripheral portion toward the peripheral portion can be restricted by the water-impermeable region 11*c*. In this case, the sample being spread to the plurality of through-holes 10*h* of the detection unit 10 can be appropriately kept in this state, thereby further improving the operability of the analysis.

In addition, the water-impermeable region 11*c* of the base material 11 of the detection unit 10 of the optical analysis chip 1 may have a structure having a water-permeable region 11*d* that allows a liquid to pass through in a part thereof.

More specifically, by providing the water-permeable region 11*c* in the base material 11 of the detection unit 10, the plurality of voids 11*h* extending toward the peripheral portion of the through-hole region and the gaps 12*h* of the water-permeable material 12 are not completely blocked. For example, as shown in FIG. 7, this water-impermeable region 11*c* can be formed in a C-shape in a plan view so as to surround the peripheral portion of the through-hole region of the base material 11, and can have a structure having the water-permeable region 11*d* between the edges of the C-shape.

The following assumes a case where the base material 11 of the detection unit 10 has a structure in which the water-permeable region 11*d* described above is provided in a part of the water-impermeable region 11*c*. In this case, by supplying a sample to the vicinity of the water-permeable region 11*d*, the sample automatically and appropriately can move to a region surrounded by the water-impermeable region 11*c* (i.e., the through-hole region in which the plurality of through-holes 10*h* are provided).

This provides an advantage that, even when the amount of the sample is small, the sample can be more appropriately spread into the plurality of through-holes 10*h*.

It may also have a structure in which a part of the base material 11 of the detection unit 10, i.e., the water-permeable region 11*d* of the base material 11, is extended outward. In this case, the extended portion corresponds to the flow path unit 15 described above.

In addition, the water-impermeable region 11*c* of the base material 11 may be formed by providing a groove excluding a water-permeable region PS.

More specifically, the base material 11 of the detection unit 10 has a groove 11*cg* that penetrates through the surface and the rear side of the base material 11 while surrounding the peripheral portion of the through-hole region, and the water-permeable region 11*d* provided between both edges of the groove protrudes from the peripheral portion of the base material 11.

For example, the base material 11 of the detection unit 10 may have a structure having a C-shaped (in a plan view) groove formed to surround the peripheral portion of the through-hole region of the base material 11, and a water-permeable region 11*d* connected to the peripheral portion of the through-hole region of the base material 11 provided between the edges of the C-shape.

With such a peripheral structure of the through-hole region in the detection unit 10 as described above, it is possible to cut the base material along the groove-shaped portion (i.e., the water-impermeable region 11*c* other than the water-permeable region 11*d*).

By doing so, in the detection unit 10, a part of the base material 11 having only the through-hole region in which the plurality of through-holes 10*h* are formed becomes possible to be separated. As a result, it is possible to operate only a part of the base material 11 of the detection unit 10 in which the through-hole region is formed when the measurement is performed, thereby further improving the flexibility in the operation during the measurement.

In addition, the end surface of the peripheral portion of the through-hole region in the base material 11 is exposed to the groove (the portion corresponding to the water-impermeable region 11*c*) when the detection unit 10 has the above-described structure. More specifically, the openings of the plurality of voids 11*h* or the openings of the plurality of gaps 12*h* are formed on the end surface. As a result, the sample L moves in the base material 11 and may reach these openings when the sample L is supplied to such a detection unit 10. However, the sample L is held in the vicinity of the openings of the plurality of voids 11*h* or of the openings of the plurality of gaps 12*h* made on the end surface due to the surface tension of the end surface when the sample L reaches the end surface. More specifically, also for the detection unit 10 having the above-described structure, the movement of the sample L that has reached the end surface is stopped at the end surface. Then, the sample L is thus prevented from flowing into the groove.

Shape Retaining Layer 11*b*

As shown in FIG. 8, the detection unit 10 of the optical analysis chip 1 may have a shape retaining layer 11*b* for retaining the shape of the base material 11 of the detection unit 10.

More specifically, the base material 11 of the detection unit 10 may have a structure having a void layer 11*a* on the surface side and a shape retaining layer 11*b* provided below the void layer 11*a*. The shape retaining layer 11*b* is formed from a material that is less likely to swell, compared with the void layer 11*a*. Further more specifically, the void layer 11*a* of the base material 11 has the structure with the plurality of voids 11*h* described above. The shape retaining layer 11*b* of the base material 11 is laminated on the void layer 11*a* provided above so that its surface is in contact with the rear side of the void layer 11*a*, and its back side serves as the rear side of the base material 11.

Figure 8A:
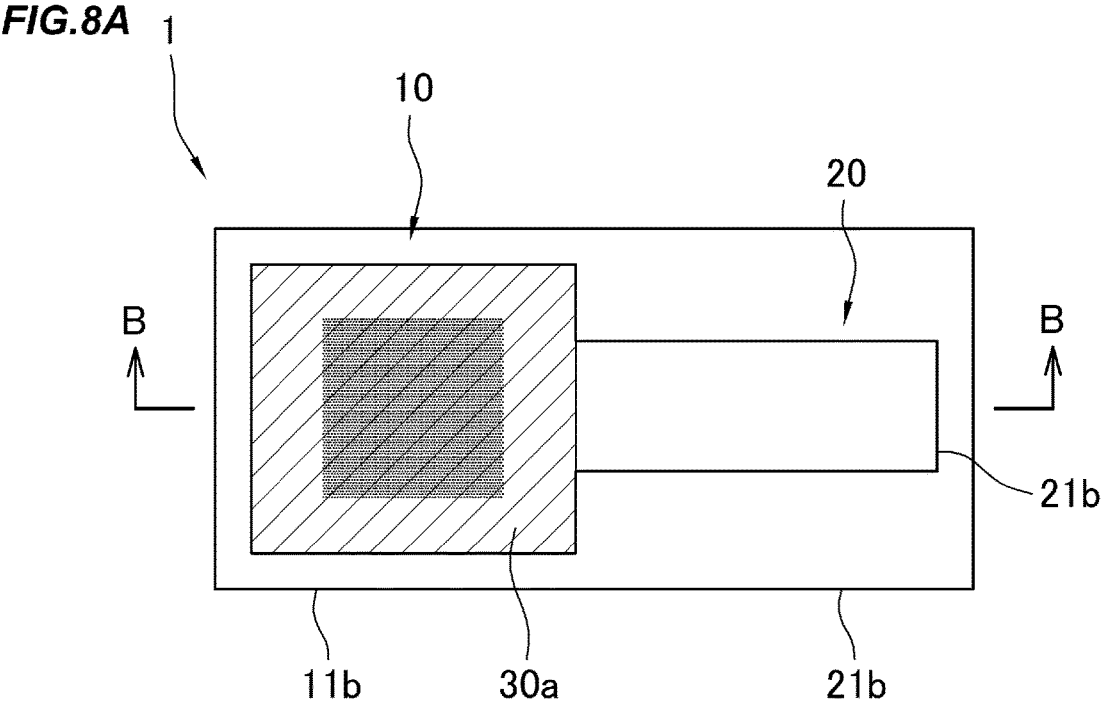
FIG. 8 is a schematic explanatory view illustrating a structure in which the detection unit 10 of the optical analysis chip 1 of the present embodiment has a shape retaining layer 11$b$ and cover members 30$a$ and 30$b$.
Figure 8B:
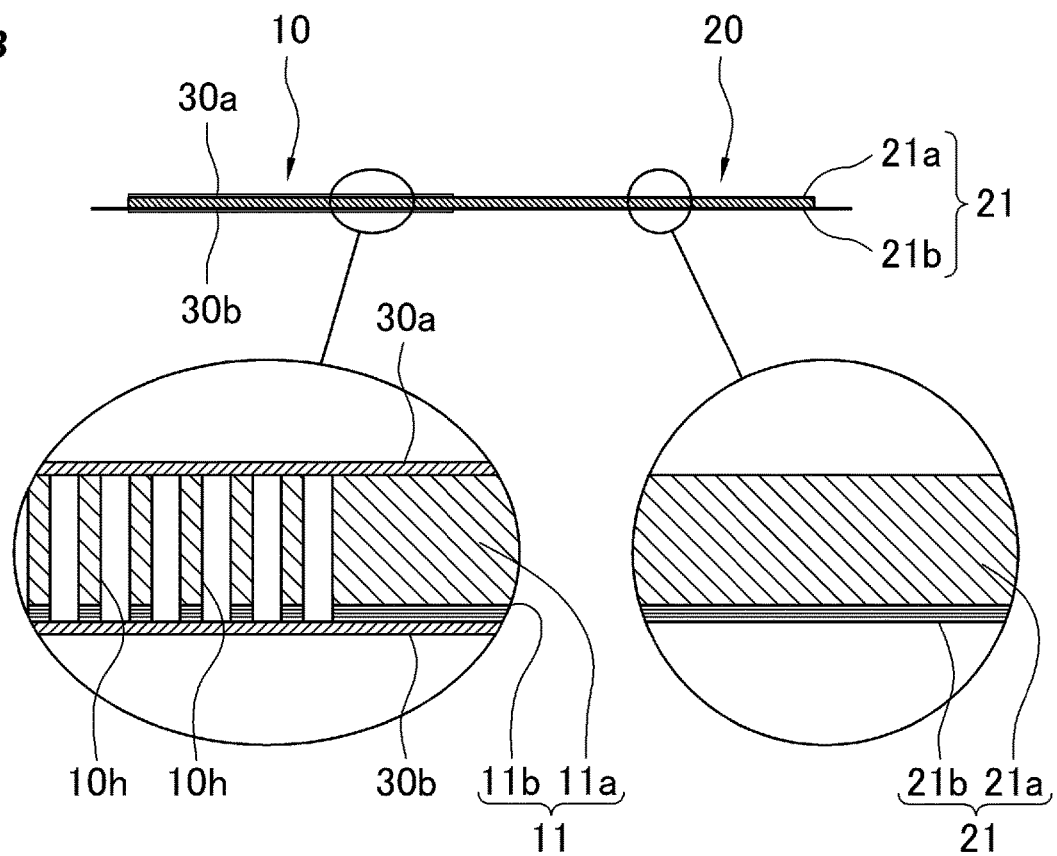

As shown in FIG. 8(B), the plurality of through-holes 10*h* are so formed as to penetrate through the void layer 11*a* and the shape retaining layer 11*b* of the base material 11. More specifically, the openings of the through-holes 10*h* on the back side of the base material 11 are formed on the rear side of the shape retaining layer 11*b* of the base material 11.

For example, if the void layer 11*a* of the base material 11 contains an additive or the like (for example, acrylic acid polymer gel or the like) that is likely to be swollen by solvents or the like in the sample L, when the sample L is supplied to the base material 11, the void layer 11*a* of the base material 11 may be swollen by the additive or the like. The stresses are more likely to mainly exert on the through-holes 10*h* when the void layer 11*a* of the base material 11 is swollen.

The swelling of the void layer 11*a* of the base material 11 may induce a change in the size of the through-holes 10*h* (such as a change of the opening of the through-hole 10*h* or a change in the length of the through-holes 10*h* (the distance between the surface opening and the rear side opening of the through-hole 10*h*). Such a phenomenon may result in variation in the thickness of the liquid films Lf formed in the through-holes 10*h* when the sample L is supplied to the plurality of through-holes 10*h*. In other words, this may result in variation in the optical path length based on the liquid film Lf formed in the through-holes 10*h*. The value obtained by the quantitative determination of a target component in the sample may vary if the optical analysis chip 1 is set in the spectrometer SM and analysis is performed in this state.

However, as described above, when the base material 11 of the detection unit 10 of the optical analysis chip 1 has the shape retaining layer 11b as described above, the shape retaining layer 11b becomes possible to suppress such swelling of the void layer 11a when the sample L is supplied.

Therefore, by forming the base material 11 into the above-described structure, the target component in the sample can be appropriately quantified even when the base material 11 of the detection unit 10 contains an additive or the like that is easily swollen by the sample L.

The shape retaining layer 11b of this base material 11 is not particularly limited insofar as it is formed of a material that is less likely to swell than the void layer 11a of the base material 11 as described above.

For example, the shape retaining layer 11b may be formed by laminating and adhering a plate-shaped member made of paper that does not easily swell (for example, paper having water resistance), a resin such as plastic, wood, metal, glass, or the like on the void layer 11a. Alternatively, the shape retaining layer 11b may be formed on the rear side of the base material 11 by immersing the base material 11 in an adhesive, a resin such as plastic, a nanofiber dispersion liquid, or the like, from the rear side of the base material 11.

the shape retaining layer 11b can be formed so that the outer edge of the plate-shaped member has an outer edge portion (the portion of the void layer 11a located outward from the cover member 30a of FIG. 8(A)) that protrudes outward from the outer edge of the void layer 11a of the base material 11 when the shape retaining layer 11b of the base material 11 is configured to be formed by laminating the above-described plate-shaped member on the void layer 11a of the base material 11.

In this case, handling property while preventing contamination can be improved since the outer edge portion can be used as a portion to be gripped during the operation.

Further, the flow path base material 21 of the flow path unit 20 may have a structure having a shape retaining layer similar to the shape retaining layer 11b of the base material 11 although the above example described the base material 11 having the shape retaining layer 11b. For example, as shown in FIG. 8(B), the structure in which the flow path base material 21 provides a shape retaining layer 21b laminated on the void layer 21a, and this shape retaining layer 21b is connected to the shape retaining layer 11b of the base material 11 can be made.

Cover Member 30

In addition, as shown in FIG. 8, the detection unit 10 of the optical analysis chip 1 may have a configuration in which a film-shaped cover member 30 (a front cover member 30a and a back cover member 30b) formed of a light transmissive member is provided on the surface and/or the back side of the base material 11. More specifically, the cover member 30 is provided in the through-hole region having the plurality of through-holes 10h of the base material 11. For example, the cover member 30 can be so provided as to be connected to the surface and/or the back side of the base material 11, thereby covering the openings 10ha and 10hb formed on the surface and/or the back side of the plurality of through-holes 10h formed in the through-hole region of the base material 11.

When thus providing the cover member 30 on the surface and/or the back side of the base material 11 of the detection unit 10, it is possible to further stabilize the steric shape of the through-holes 10h. Therefore, it is possible to prevent variation in the thickness of the liquid films Lf formed in the through-holes 10h when the sample is supplied to the base material 11, thereby further improving quantitativity of the target component in the sample.

Furthermore, the cover member 30 becomes possible to prevent the liquid films Lf formed in the through-holes 10h from volatilizing. More specifically, it can prevent changes in concentration of the target component in the sample L due to volatilization of the liquid films Lf. For example, the liquid films Lf formed in the through-holes 10h are easily volatilized when the optical analysis chip 1 is heated to allow the sample L to react in the reaction field. However, the cover member becomes possible to prevent such volatilization. Therefore, in the case in which it takes some time before performing the measurement after the liquid films Lf are formed, using the structure in which the cover member is provided becomes possible to more appropriately quantify the target component in the sample L.

Furthermore, as described above, the cover member 30 can be used as a reaction field supporting a reagent advantageous for the detection. More specifically, a detection material such as a reaction reagent that binds to the target component in the sample L is provided on the inner face (the plane facing the through-hole region) of the cover member 30 (the front cover member 30a, the rear cover member 30b) in the reaction field.

A method for providing this detection material on the cover member 30 is not particularly limited; for example, the detection material can be provided by being supported or held. Examples of the method for supporting or holding the detection material in the cover member 30 can use a method of, for example, applying a detection material to the inner surface of the cover member, followed by drying.

In this manner, for example, the applied detection material is eluted when a liquid comes into contact with the surface of the cover member 30 supporting the detection material. Then, the sample L supplied to the optical analysis chip 1 reaches the inside of the through-holes 10h and forms liquid films Lf. Further, the detection material advantageous for the detection can be eluted from the cover member 30 to the liquid films Lf when the liquid surface of the liquid films Lf come into contact with the inner face of the cover member 30. The target component and the detection material can be combined if the target component is present in the liquid film Lf. Light absorption based on the target component in the liquid film Lf occurs during the optical analysis if the detection material has a function of absorbing specific wavelengths in the irradiation light L1, thereby becoming capable of more appropriate quantitative determination of the target component in the sample L.

In addition, for example, it is possible to allow the target component to be adsorbed or bonded to the detection material supported on the inner face of the cover member 30 when the detection material is supported on the inner face of the cover member 30. More specifically, since the target component can be directly held on the inner face of the cover member 30, when the irradiation light L1 is emitted to the liquid film Lf in such a state, the target component can be appropriately quantified in the same manner as described above.

Furthermore, the detection material may be provided on the cover member 30 in such a way that the detection material is present on the surface and inside the cover member 30. For example, the cover member 30 is formed by mixing the detection material with a material (e.g., plastic or nanofiber nf) of the cover member 30. By using this cover member 30, the target component can be adsorbed or bonded to the inner face of the cover member 30 and the detection material positioned slightly inside relative to the inner face of the cover member 30. By doing so, light absorption or the like can be induced in the inner face and inside of the cover member 30. In this case, the target component in the sample L becomes possible to be more stably and appropriately quantified.

Further, it is possible to reduce the influence of the cover member 30 on the analysis since the cover member 30 has a light transmissive property.

The material of this cover member 30 is not particularly limited insofar as the material has a light transmissive property. Examples of the material of the cover member can use such as plastic, glass, or nanofibers.

Note that the cover member 30a provided on the surface side of the base material 11 of the detection unit 10 of the optical analysis chip 1 corresponds to the "surface cover member" in the claims, and the cover member 30b provided on the back side of the base material 11 of the detection unit 10 of the optical analysis chip 1 corresponds to the "back cover member" in the claims.

EXAMPLES

The present invention is explained below with reference to Examples; however, the present invention is not limited to these Examples.

Experiment 1
Determination of Fe(II)-1,10-Phenanthroline Complex Using Optical Analysis Chip Having Elliptical Through-Holes
Preparation of Optical Analysis Chip A cellulose qualitative filter paper (manufactured by ADVANTEC, model number: No. 2, mass: 125 g/m$^2$, thickness: 0.26 mm, binder-free, void ratio: about 68%) was used. A rectangle with a short side (length in the vertical direction with respect to the paper plane) of about 6 mm and a long side (length in the horizontal direction with respect to the paper plane) of about 12 mm was cut out from the filter paper. A 5 mm square through-hole region having a plurality of through-holes was formed in the vicinity of one of the short sides of the cut piece (see FIG. 10(A)).

Preparation of Through-Holes

A laser processing device (manufactured by Universal Systems Co., Ltd., model number: ILS9.75, laser output: 40 W) was used to form fine perforations (through-holes) penetrating through the surface and the rear side of the filter paper.

The irradiation condition was as follows: laser power=10%, speed=5, 40 pulses/inch.

Figure 10A:
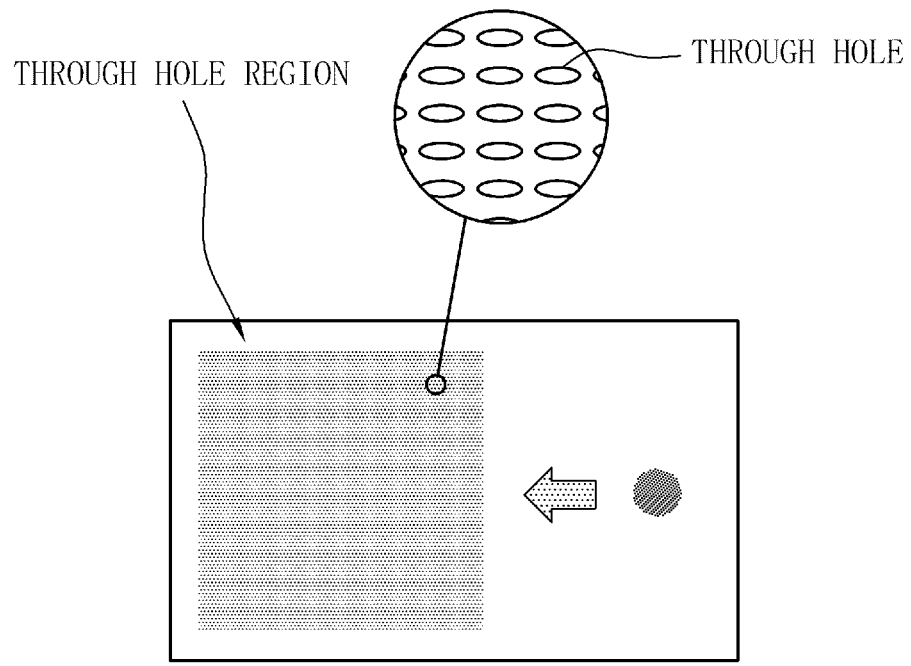
FIGS. 10(A) and 10(B) are schematic explanatory views each illustrating the optical analysis chip 1 of the present embodiment used for an experiment.
Figure 10B:
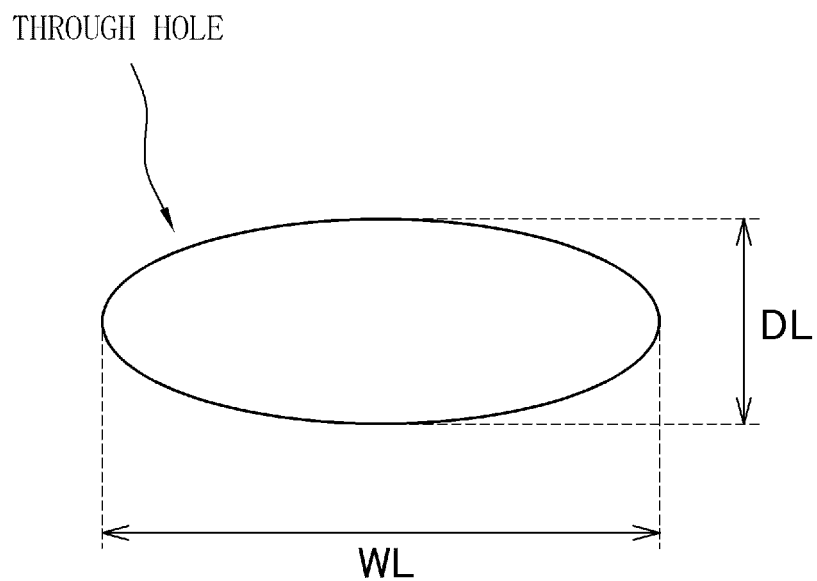

As shown in FIG. 10(B), each through-hole was formed to have an elliptical shape with a major axis WL of about 600 μm and a minor axis DL of about 300 μm.

The shape of the through-hole and the liquid film formed in the through-hole were observed in a transmitted light mode using an optical microscope (Keyence VH-Z100R).

Preparation of Samples

Each solution of Fe(II)-1,10-phenanthroline complex was prepared.

Each solution was prepared so that the concentration of iron was 0 (blank), 0.40 mmolkg$^{-1}$, 0.79 mmolkg$^{-1}$, 1.17 mmolkg$^{-1}$, and 1.55 mmolkg$^{-1}$.

Further, the Fe(II)-1,10-phenanthroline complex solutions were prepared so as to contain a predetermined concentration of ammonium Fe(II)sulfate hexahydrate, 0.5% w/w of hydroxylammonium chloride as an antioxidant (reducing agent to Fe(II)), 0.1 gkg$^{-1}$ of 1,10-phenanthroline as a complex-forming agent, and 0.02 molkg$^{-1}$ of acetic acid-sodium acetate as a pH buffer.

Analysis
Analysis Based on Absorption Spectrometry

The spectrometer used herein included a stage, a light irradiation fiber for emitting light to a portion below the measurement window (having a diameter of about 10 mm) of the stage, and a light receiving fiber for receiving transmitted light provided above the measurement window (see FIG. 9).

A deuterium-halogen light source (manufactured by Ocean Optics, Inc., DH-2000L) was used as the light source of the light irradiation fiber.

The base end of the light receiving fiber was connected to a spectrometer (UV-VIS-IR spectrometer, manufactured by Ocean Optics, Inc., USB2000) to enable measurement of absorbance in the range from 250 nm to 860 nm (so-called UV-VIS-IR region).

A calibration curve was made by plotting the values obtained by subtracting the absorbance at 560 nm from the absorbance at 510 nm versus the concentration.

The experimental was performed as follows.
1) The optical analysis chip is set so that the through-hole region thereof is positioned in the measurement window of the stage of the spectrometer.
2) Ultraviolet/visible light is emitted from a light source (balanced deuterium halogen light source) of the light irradiation fiber.
3) Light is blocked by a shutter, and measurement (zero adjustment) is performed.
4) The shutter is opened, and ultraviolet, visible, infrared light is emitted.
5) A predetermined amount of ultrapure water is added dropwise as a blank; after a predetermined time has elapsed, the transmitted light is measured ($I_0$).
6) The blank solution is absorbed with absorption paper.
7) A predetermined amount of a sample is supplied dropwise; after a predetermined time has elapsed, the transmitted light is measured (I).
8) An absorption spectrum is prepared based on the Lambert-Beer equation.

Addition of Sample

The optical analysis chip was set so that the through-hole region thereof was positioned in the measurement window of the stage of the spectrometer, and Fe(II)-1,10-phenanthroline complex solutions having different concentrations were prepared and 50 μL of each solution was supplied to a space having no through-holes near the through-hole region (see FIG. 10(A)). More specifically, the sample was supplied so that the left edge of the outline of the sample thus supplied was positioned approximately 3 to 5 mm inward (i.e., on the right edge side) from the left edge of the optical analysis chip.

Results

It was confirmed that a liquid film was formed in the through-holes even when a sample was supplied to a portion away from the through-hole region in a state where the optical analysis chip was level. The results of the observation of through-holes further revealed that a liquid film of Fe(II)-1,10-phenanthroline solution was formed in each through-hole.

Figure 11:
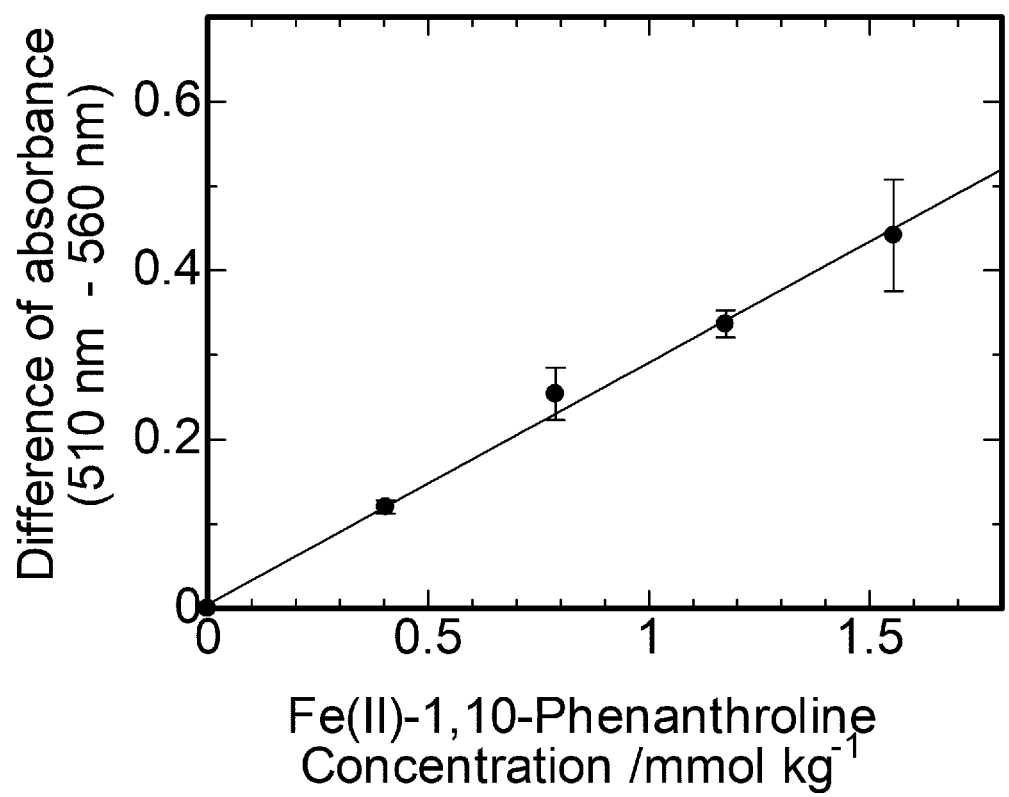
FIG. 11 is a graph showing the results (calibration curve) of Experiment 1.

FIG. 11 shows a calibration curve of ultraviolet-visible absorption spectrum of Fe(II)-1,10-phenanthroline. It was confirmed that a calibration curve with a correlation coefficient $R^2$ of 0.990 was obtained.

Experiment 2
Quantitative Determination of Sodium Copper Phthalocyanine Tetrasulfonate Using Optical Analysis Chip Having Elliptical Through-Holes
Preparation of Optical Analysis Chip A rectangle having a short side of about 6 mm and a long side of about 12 mm was cut out from the filter paper similar to that used in Experiment 1. A 5 mm square through-hole region having the plurality of through-holes was formed in the vicinity of one of the short sides of this cut piece (see FIG. 10(A)).
Preparation of Through-Holes A laser processing device similar to that used in Experiment 1 was used to form fine perforations (through-holes) penetrating through the surface and the rear side of the filter paper.

The irradiation condition was as follows: laser power=10%, speed=5, 40 pulses/inch.

Each through-hole was formed to have an elliptical shape with a major axis of about 600 and a minor axis of about 300 μm (see FIG. 10(B)).

The shape of the through-hole and the liquid film formed in the through-hole were observed in a transmitted light mode using an optical microscope similar to that used in Experiment 1.
Preparation of Sample 0.098 g ($1.0 \times 10^{-4}$ mol) of sodium copper phthalocyanine tetrasulfonate (manufactured by Fujifilm Wako Pure Chemical Industries, Ltd., special grade) was dissolved in 10 ml of pure water to prepare a solution of 10 mmolkg$^{-1}$. This solution was further diluted to prepare solutions having concentrations of sodium copper phthalocyanine tetrasulfonate of 0.1 mmolkg$^{-1}$, 0.22 mmolkg$^{-1}$, 0.47 mmolkg$^{-1}$, and 0.76 mmolkg$^{-1}$. A blank sample was prepared using pure water.
Analysis 1
Analysis Based on Absorption Spectrometry A spectrometer similar to that used in Experiment 1 was used.

A light source similar to that used in Experiment 1 was used as the light source of the light irradiation fiber.

The base end of the light receiving fiber was connected to a spectrometer (UV-VIS-IR spectrometer, manufactured by Ocean Optics, Inc., USB2000) to enable measurement of absorbance in the range from 250 nm to 860 nm.

A calibration curve was made by plotting the values obtained by subtracting the absorbance at 620 nm from the absorbance at 760 nm versus the concentration.
Addition of Sample 20 μL each of sodium copper phthalocyanine tetrasulfonate solutions having various concentrations prepared in the same manner as in Experiment 1 were added (see FIG. 10(A)).
Results of Analysis 1

From the results of observation of the through-holes, it was confirmed that the liquid film of the sodium copper phthalocyanine tetrasulfonate solution was formed in each through-hole.

In the observation upon the formation of the liquid film, it was confirmed that the supplied sodium copper phthalocyanine tetrasulfonate solution was spread to inside of the through-hole via the portions having a small curvature of the elliptical through-hole (near the two points used for measurement of major axis; the left and right portions of the through-hole in FIG. 10(B)).

Figure 12:
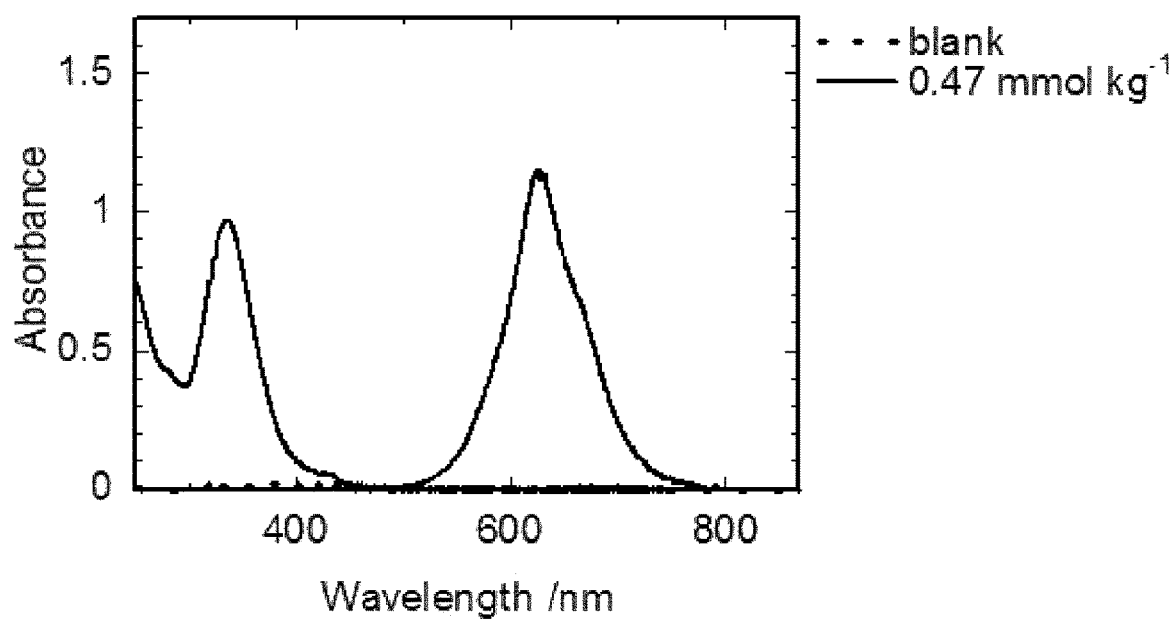
FIG. 12 is a diagram showing the results (absorption spectrum) of Analysis 1 of Experiment 2.

FIG. 12 shows an absorption spectrum.

As shown in FIG. 12, a clear absorption spectrum in the UV-VIS-IR wavelength range associated with the presence of sodium copper phthalocyanine tetrasulfonate was confirmed. On the other hand, no significant background absorption spectrum was confirmed in the same wavelength range for pure water added as a blank. This confirmed that the optical analysis chip, which serves as an absorption cell, having through-holes is capable of measuring a wide range of spectrum in the UV-VIS-IR wavelength range.

Figure 13:
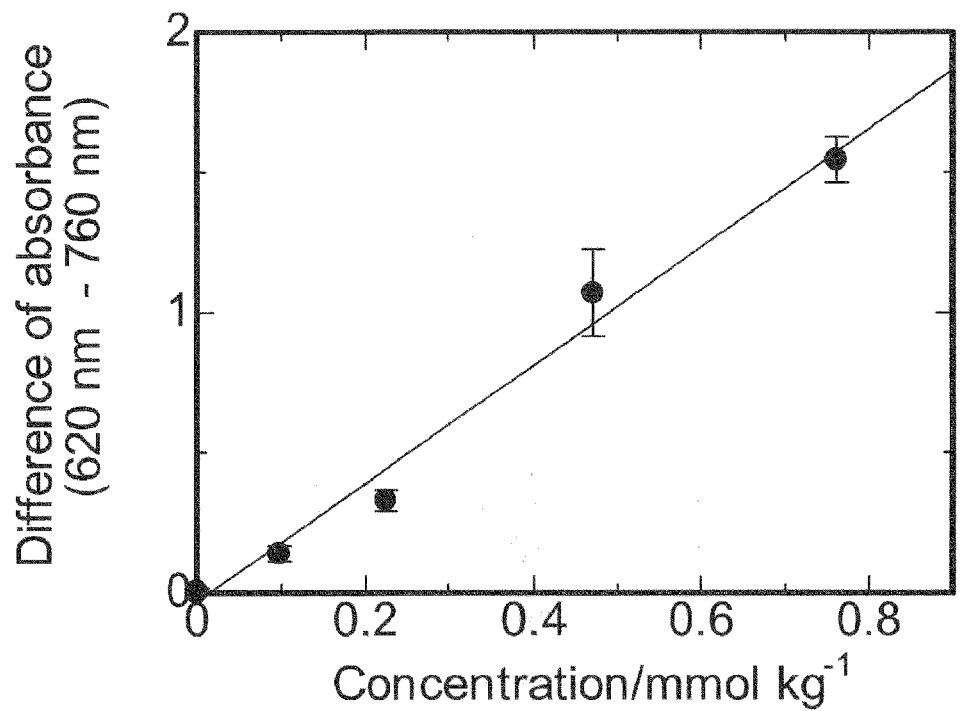
FIG. 13 is a graph showing the results (calibration curve) of Analysis 1 of Experiment 2.

FIG. 13 shows a calibration curve of ultraviolet-visible absorption spectrum of sodium copper phthalocyanine tetrasulfonate. It was confirmed that a calibration curve with a correlation coefficient $R^2$ of 0.992 was obtained.
Thickness of Liquid Film Formed in Through-Hole The observation of the liquid film revealed that the thickness of the liquid films formed in the through-holes had substantially the same thickness as that of the through-hole region of the optical analysis chip.

The thickness of the liquid film formed in the through-holes of the optical analysis chip was determined by conversion according to the Lambert-Beer equation based on the results of absorbance measurement of an aqueous sodium copper phthalocyanine tetrasulfonate solution when a general ultraviolet-visible absorption photometer and a plastic cell having a 1 cm optical path length were used.

The results revealed that the absorbance of $9.22 \times 10^{-3}$ mmolkg$^{-1}$ of aqueous sodium copper phthalocyanine tetrasulfonate solution measured using a plastic cell having an optical path length of 1 cm was 0.481.

The absorbance ratio at the same concentration was determined, with the result that through-hole:1 cm=1:23.4. Accordingly, the thickness of the liquid film formed in the through-hole was able to be determined with 0.427 mm.

Since the filter paper used in the experiment had a thickness of 0.26 mm in a dry state, it was confirmed that the thickness (film length) of the liquid film formed in the through-hole was slightly larger (about 1.6 times larger) than the dry thickness of the filter paper.

This is presumably attributable to the fact that the filter paper is swollen and the surface and the rear side of the liquid film have a convex meniscus shape.
Analysis 2
Analysis Based on Color Tone Method The liquid films formed in the through-holes were observed in a transmitted light mode using an optical microscope (Keyence VH-Z100R), and the color tone of the liquid films formed in the through-holes after each of the sodium copper phthalocyanine tetrasulfonate solutions was added was observed. Further, the observation was performed by emitting white light from the back side of the through-hole region of the optical analysis chip, and the transmitted light was received in a transmitted light mode, and a received image was captured by a camera.

The color tone was evaluated according to the RGB color system using software (Paint, version 6.1) manufactured by Microsoft Corporation based on the image captured by a built-in digital camera of the optical microscope.
Addition of Sample 20 μL each of sodium copper phthalocyanine tetrasulfonate solutions having various concentrations prepared in the same manner as in Experiment 1 were added (see FIG. 10(A)).
Evaluation of Color Tone The liquid film formed in each through-hole was observed using an optical microscope, and the RGB color system was evaluated based on the observed image.

For the color tone evaluation, first, liquid films formed in the through-holes at three positions of a through-hole region (sample supplying side, the center, and sample sending end side are equally divided into three sections) were observed, and RGB of the liquid films at the three positions were obtained according to the RGB color system. Next, an average value (average RGB) of the obtained RGB at the three positions is determined. The same operation is performed for each concentration, thereby determining the average RGB for each concentration.

Results of Analysis 2

FIG. 14(A) is a graph representing the RGB color system as an XY biaxial plane. The value on the X-axis is represented by X value=(R value/R value+G value+B value) and the value on the Y-axis is represented by Y value=(G value/R value+G value+B value). The black circle in the graph represents the average RGB for each concentration.

FIG. 14(B) shows coloring state of the liquid film.

As shown in FIG. 14(B), it was observed that the coloring state of the liquid film changes depending on the concentration of the sodium copper phthalocyanine tetrasulfonate solution. This indicates that the light absorption changes depending on the concentration.

Figure 15:
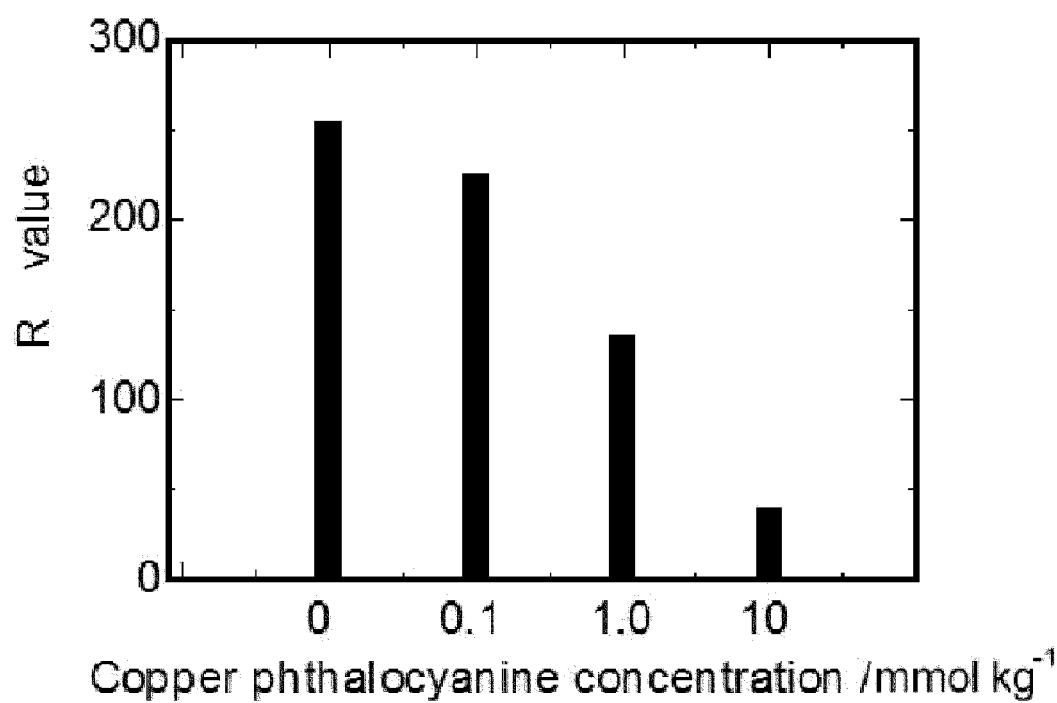
FIG. 15 is a diagram showing the results (relationship between R value and concentration of sodium copper phthalocyanine tetrasulfonate solution) of Analysis 2 of Experiment 2.

FIG. 15 shows the relationship between the R value and the concentration of the sodium copper phthalocyanine tetrasulfonate solution.

As shown in FIG. 15, the color tone of the liquid film formed in the through-hole was expressed as a value according to the RGB color system based on the obtained image, and a correlation between the R value and the concentration could be confirmed.

Experiment 3

Quantitative Determination of Sodium Copper Phthalocyanine Tetrasulfonate Using Optical Analysis Chip of Bulky Glass Fiber Filter Paper Preparation of Optical Analysis Chip A glass fiber filter paper (manufactured by ADVANTEC, model number: GA-100, mass: 110 g/m$^2$, thickness: 0.44 mm, binder-free, void ratio: about 89%) was used as the filter paper. A rectangle having a short side of about 6 mm and a long side of about 12 mm was cut out from this filter paper in the same manner as in Experiment 1. A 5 mm square through-hole region having a plurality of through-holes was formed in the vicinity of one of the short sides of this cut piece (see FIG. 10(A)).

Preparation of Through-Holes

A laser processing device similar to that used in Experiment 1 was used to form fine perforations (through-holes) penetrating through the surface and the rear side of the filter paper.

The irradiation condition was as follows: laser power=5%, speed=5, 40 pulses/inch.

The through-hole was formed to have an elliptical shape with a major axis of about 510 and a minor axis of about 380 μm (see FIG. 10(B)).

The shape of the through-hole and the liquid film formed in the through-hole were observed in a transmitted light mode using an optical microscope (Keyence VH-Z100R).

Preparation of Sample 0.098 g ($1.0 \times 10^{-4}$ mol) of sodium copper phthalocyanine tetrasulfonate (manufactured by Fujifilm Wako Pure Chemical Industries, Ltd., special grade) was dissolved in 10 ml of pure water to prepare a solution of 10 mM. This solution was further diluted to prepare a solution having a concentration of sodium copper phthalocyanine tetrasulfonate of 0.47 mM.

Analysis

Analysis Based on Absorption Spectrometry

A spectrometer similar to that used in Experiment 1 was used.

A light source similar to that used in Experiment 1 was used as the light source of the light irradiation fiber.

The base end of the light receiving fiber was connected to a spectrometer (UV-VIS-IR spectrometer, manufactured by Ocean Optics, Inc., USB2000) to enable measurement of absorbance in the range from 620 nm to 760 nm.

Addition of Sample

40 μL of the sodium copper phthalocyanine tetrasulfonate solution prepared in the same manner as in Experiment 1 was added (see FIG. 10(A)).

Results

The results of observation of the through-holes revealed that the liquid film of the sodium copper phthalocyanine tetrasulfonate solution was formed in each through-hole.

The absorbance of 0.47 mM sodium copper phthalocyanine tetrasulfonate was 1.66±0.26 (average±standard deviation of three measurements).

In Experiment 3, a slightly higher absorbance was obtained, compared with the absorbance at the same concentration in Experiment 2. Based on the greater absorbance at the same concentration, a slight increase in the thickness of the liquid film formed in the through-hole could be confirmed.

Thickness of Liquid Film Formed in Through-Hole

The thickness of the liquid film formed in the through-hole was calculated in the same manner as in Experiment 2, and was determined to be 0.69 mm.

It was confirmed that the thickness of the liquid film formed in the through-hole was slightly larger (about 1.5 times) than the dry thickness of the glass fiber as in Experiment 2 because the thickness of the filter paper (glass fiber filter paper) used in the experiment was 0.44 mm in a dry state.

This is presumably attributable to the fact that the filter paper (glass fiber filter paper) is swollen and the surface and the rear side of the liquid film have a convex meniscus shape.

In addition, the reason why the increase rate of the thickness of the liquid film relative to the dry thickness of the filter paper (glass fiber filter paper) is smaller than that of the filter paper (cellulose fiber filter paper) used in Experiment 2 is presumably attributable to the property of the glass fiber filter paper which does not easily swell. More specifically, the glass fiber filter paper in a dry state has a fluffy and coarse state since hydrogen bonds between the fibers are insignificant in the glass fiber filter paper. On the other hand, the fibers of the cellulose fiber filter paper used in Experiment 2 undergo hydrogen bond in a dry state, thus having a hard and dense state. It is assumed that, when water is supplied to them, the cellulose fiber filter paper absorbs water and the hydrogen bond between the fibers becomes relatively weak as compared with the dry state, and therefore the fibers easily swell, whereas the swelling ratio of the glass fiber filter paper is low as compared with that of the cellulose fiber filter paper because the fibers of the glass fiber filter paper are not closely bonded even in the original state.

Experiment 4

Quantitative Determination of Sodium Copper Phthalocyanine Tetrasulfonate Using Optical Analysis Chip Having Shape Retaining Layer Preparation of Optical Analysis Chip A filter paper combined with a water-resistant paper was prepared by overlaying a water-resistant paper on a filter paper, and a rectangle with a short side of about 6 mm and a long side of about 13 mm was cut out from this combined filter paper. A 5 mm square through-hole region having a plurality of through-holes was formed in the vicinity of one of the short sides of this cut piece (see FIG. 10(A)).

The water-resistant paper portion in this filter paper combined with a water-resistant paper corresponds to the shape retaining layer of this optical analysis chip.

The filter paper combined with a water-resistant paper was produced by the following method.

A water-resistant paper (water-resistant paper for color laser, extra thick, product number: LBP-WPF22MDP, manufactured by Sanwa Supply Inc.) is perpendicularly fixed. A spray adhesive (product number: 51071448, manufactured by Kokuyo Co., Ltd.) is sprayed on the entire water-resistant paper for 10 seconds. Immediately after the spraying, the filter paper is placed on the sprayed surface, and the papers are bonded together by applying a pressure using a desk press (10 MPa, 1 minute), thereby preparing the filter paper combined with a water-resistant paper. The filter paper combined with a water-resistant paper thus prepared was stored in a sealed environment until through-holes were formed.

As the filter paper, three types of filter paper for chromatography (manufactured by ADVANTEC, model numbers: No. 590, No. 526, No. 514) were used.

The thickness of the filter paper increases in an ascending order of No. 514, No. 526, and No. 590. The basis weight of the filter paper per unit area decreases in a descending order of No. 526, No. 590, and No. 514.

Preparation of Through-Holes

A laser processing device similar to that used in Experiment 1 was used to form fine perforations (through-holes) penetrating through the surface and the rear side of the filter paper, thereby preparing an optical analysis chip made of a filter paper combined with a water-resistant paper.

Irradiation conditions: the conditions shown in Table 1 below were used for filter paper No. 590. For filter paper No. 526, the conditions were as follows: laser power=10%, speed=5, 40 pulses/inch. For filter paper No. 514, the conditions were as follows: laser power=8%, speed=5, 40 pulses/inch.

TABLE 1

CONDITIONS OF LASER PROCESSING DEVICE

| LASER POWER OUTPUT RATIO/% | SPEED OUTPUT RATIO/% | PULSE PER INCH (PPI) |
|---|---|---|
| 10% | 5% | 40 |
| 20% | 5% | 40 |
| 30% | 5% | 40 |
| 20% | 3% | 30 |

The through-hole was formed to have an elliptical shape with a major axis of 300 to 700 μm and a minor axis of 200 to 400 μm (see FIG. 10(B)).

The shape of the through-hole in this optical analysis chip and the liquid film formed in the through-hole were observed in a transmitted light mode using an optical microscope similar to that used in Experiment 1.

Table 2 below shows the results of the observation of the through-hole of this optical analysis chip (filter paper; No. 590, paper thickness; 0.954 mm) as a representative example.

Note that the shape of the through-hole was measured by measuring the opening on the surface side (filter paper side) of the optical analysis chip. The shape of the through-hole was slightly elliptical. The hole diameters in the table are measured values of the major axis of the elliptical shape.

TABLE 2

OBSERVATION OF THROUGH-HOLES (FILTER PAPER COMBINED WITH WATER-RESISTANT PAPER)

| | SAMPLE A | SAMPLE B | SAMPLE C | SAMPLE D |
|---|---|---|---|---|
| LASER POWER | 10% | 20% | 30% | 20% |
| SPEED/PULSE | 5% · 40 | 5% · 40 | 5% · 40 | 3% · 30 |
| HOLE DIAMETER/μm | 476.8 ± 49.6 | 574.2 ± 53.1 | 648.3 ± 59.4 | 552.1 ± 47.4 |
| NUMBER OF HOLES/holes | 88 | 88 | 88 | 64 |

Preparation of Sample 0.098 g ($1.0 \times 10^{-4}$ mol) of sodium copper phthalocyanine tetrasulfonate (manufactured by Fujifilm Wako Pure Chemical Industries, Ltd., special grade) was dissolved in 10 ml of pure water to prepare a solution of 10 mmolkg$^{-1}$. This solution was further diluted to prepare a sample having a concentration of sodium copper phthalocyanine tetrasulfonate of 0.2 mmolkg$^{-1}$.

Analysis

Analysis Based on Absorption Spectrometry

A balanced deuterium-halogen light source (manufactured by Ocean Optics, Inc., DH-2000 BAL) was used as the light source of the light irradiation fiber.

The base end of the light receiving fiber was connected to a spectrometer (UV-VIS-IR spectrometer, manufactured by Ocean Optics, Inc., FLAME-S) to enable measurement of absorbance in the range from 250 nm to 860 nm.

Note that the measurement results were analyzed by spectrometry measurement software (Ocean Optics, Inc., OCEANVIEW).

The experimental operation was performed as follows.

The operations 1) to 5) were performed in the same manner as in Experiment 1, and the operation 5) and subsequent operations were performed as follows.

6) After the optical analysis chip is exchanged, a predetermined amount of sample is supplied dropwise. After a certain period of time elapsed, the transmitted light is measured (I).

7) An absorption spectrum is made based on the Lambert-Beer equation.

Addition of Sample

The prepared sodium copper phthalocyanine tetrasulfonate solution was added in the same manner as in Experiment 1. The amount of the sample added was adjusted according to the thickness of the filter paper used for the optical analysis chip.

Figure 17A:
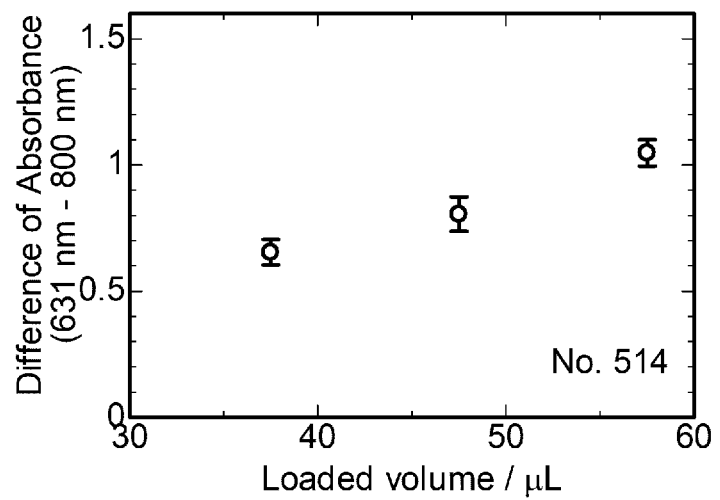
FIG. 17 is a diagram showing the results (relationship between change in dropwise addition amount of sample and absorbance) of Experiment 4.
Figure 17B:
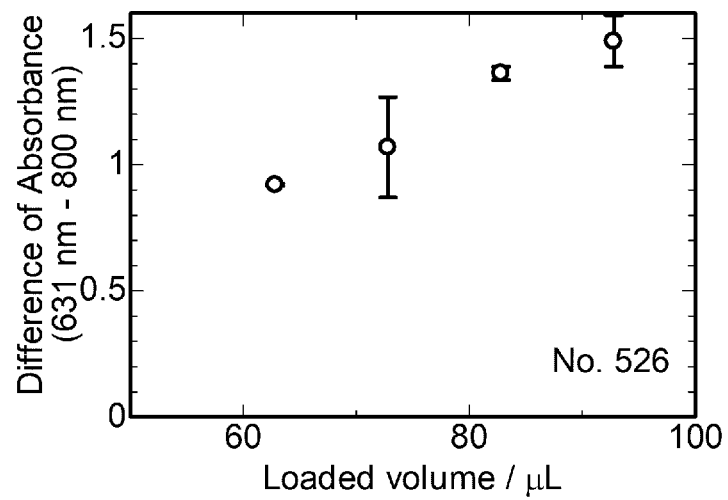
Figure 17C:
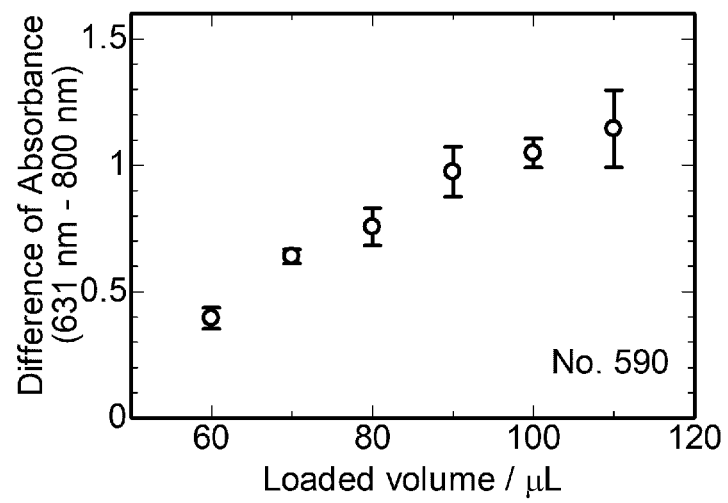

FIG. 17 shows the amount of the sample added to each of the optical analysis chips (made of filter paper No. 590, filter paper No. 526, and filter paper No. 514).

Results

The results of observation of the through-holes revealed that the liquid film of the sodium copper phthalocyanine tetrasulfonate solution was formed such that the opening of each through-hole and the upper face of the liquid film substantially coincide with each other when 60 μL of the sample was used.

Figure 16:
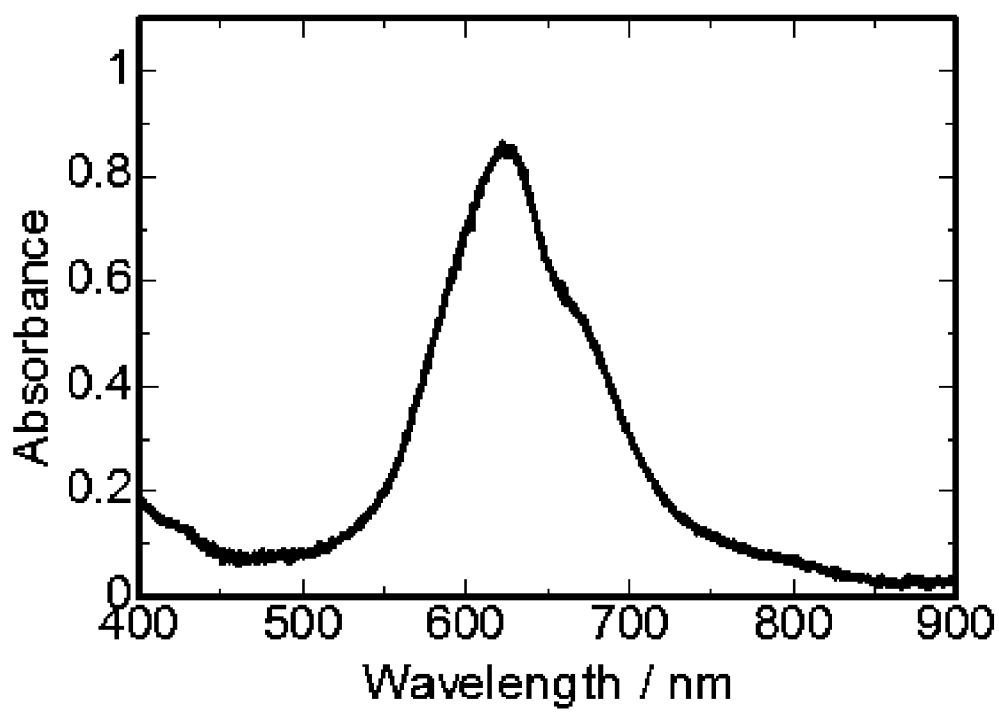
FIG. 16 is a diagram showing the results (absorption spectrum) of Experiment 4.

FIG. 16 shows an absorption spectrum when 100 μL of a sample was added. As shown in FIG. 16, it was confirmed that the optical analysis chip having the shape retaining layer (water-resistant paper) can be appropriately used in the optical analysis according to absorption spectrometry.

FIG. 17 shows the relationship between change in dropwise addition amount of sample and absorbance. The results show the relationship between the dropwise addition amount of the sample A and difference in absorbance (absorbance 631 nm-absorbance 800 nm). Further, similar results were obtained for samples B to D.

As shown in FIG. 17, for each of the optical analysis chips (the one using filter paper No. 590, the one using filter paper No. 526, and the one using filter paper No. 514), the absorbance increased with the increase in the amount of the sample added dropwise. Further, it was confirmed that the repeatability in the measurement of absorbance became more stable as the amount of the sample added dropwise increased.

FIG. 18 shows side-view observation of the through-hole region of the optical analysis chip (sample A, using filter paper No. 590).

Figure 18A:
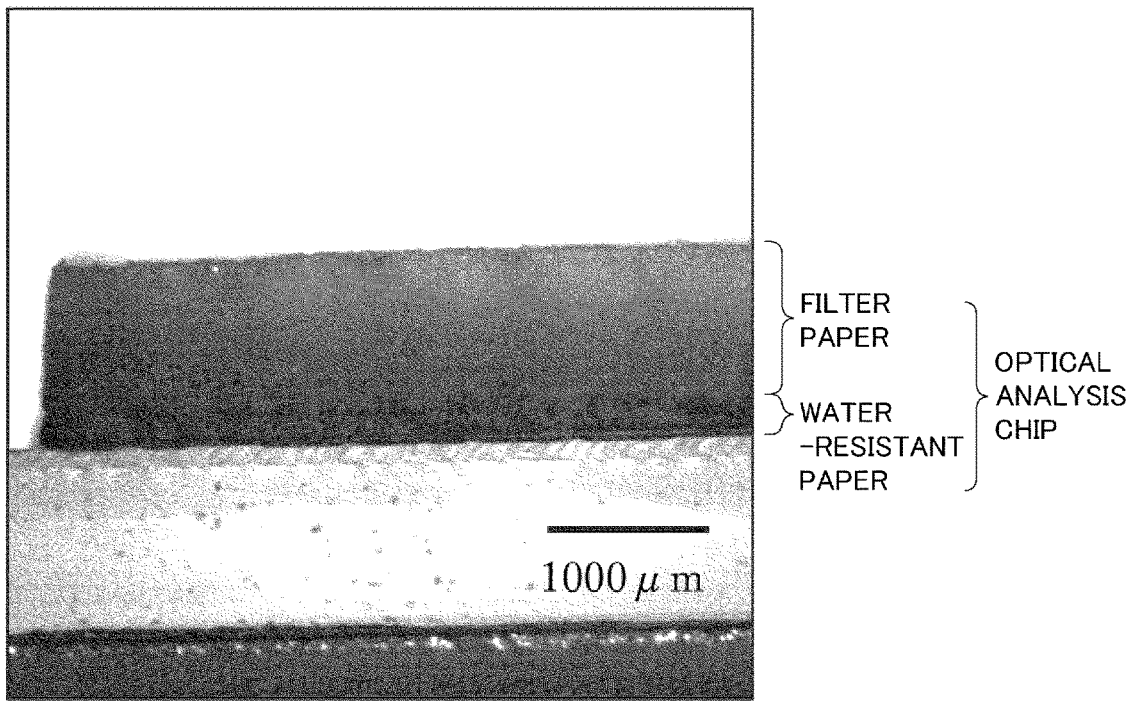
FIG. 18 is a diagram showing the results (observation of through-hole region in a side view) of Experiment 4.
Figure 18B:
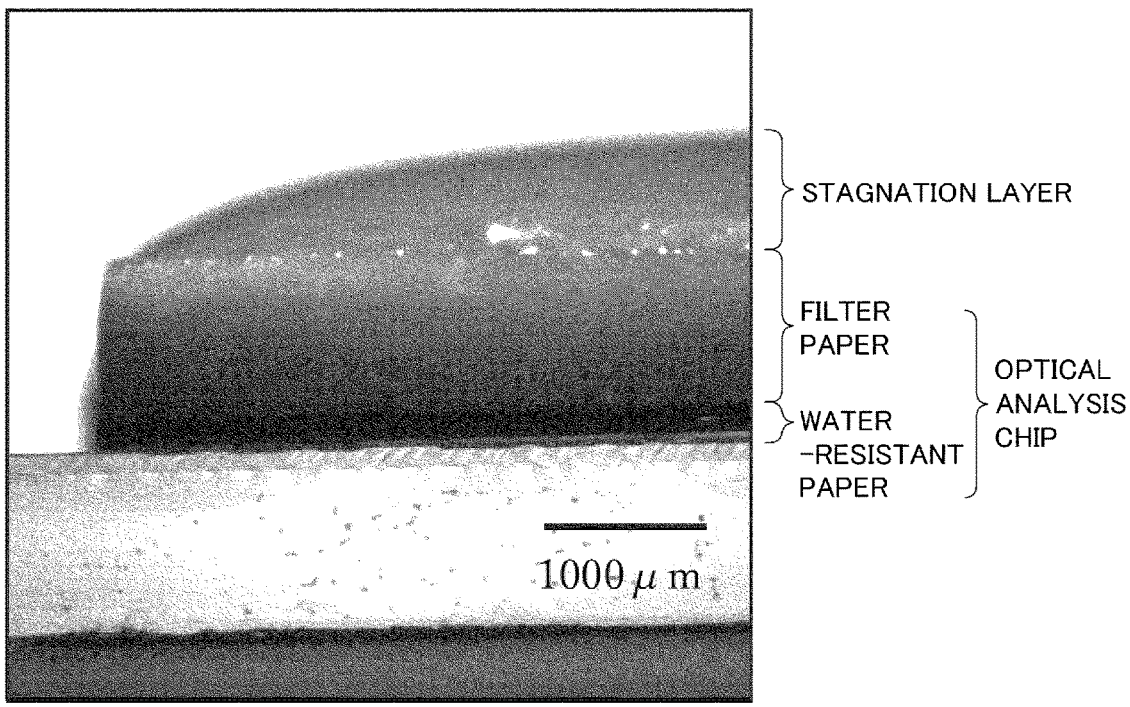

FIG. 18(A) shows an observation result of a state after 60 μL of the sample was added dropwise and spread, and FIG. 18(B) shows an observation result of a state after 100 μL of the sample was added dropwise and spread.

These results were obtained 30 seconds after the addition of the sample. It was confirmed that the sample can be retained on the surface of the through-hole region (a stagnation layer of the sample can be formed) when the addition amount was 100 μL. This stagnation layer was confirmed when the addition amount of the sample was 70 μL or more. It is assumed that the stagnation layer was formed by surface tension of the surface of the optical analysis chip (the surface of the filter paper) and the sample.

The results of the experiment revealed that the liquid film became thicker as the amount of the sample increased, and that, when the amount exceeds a certain amount, a stagnation layer enables to be formed on the surface of the through-hole region. Further, it was confirmed that the optical path length was increased corresponding to the length of the stagnation layer in the absorption spectrometry since the absorbance increased with the increase in the thickness of the stagnation layer.

In addition, in terms of measurement repeatability, it was confirmed that the measurement repeatability enables to be improved under a condition in which the amount of the sample added dropwise was large. This is presumably because of the fact that the sample spread evenly over the entire through-hole region of the optical analysis chip with the increase in the amount of the sample, and hence the degree of swelling of the filter paper and the thickness of the stagnation layer of the sample became stable; as a result, variations in the optical path length were reduced.

Experiment 5

Suitability Test for Sample Containing Impurities

Preparation of Optical Analysis Chip

A filter paper combined with a water-resistant paper was prepared in the same manner as in Experiment 4.

A filter paper for chromatography (No. 590) was used as the filter paper.

Preparation of Through-Holes

A laser processing device similar to that used in Experiment 4 was used to form fine perforations (through-holes) on the filter paper combined with a water-resistant paper under the same conditions as those in the case of sample A so that the perforations (through-holes) penetrate through the surface and the rear side of the filter paper combined with a water-resistant paper, thereby preparing the optical analysis chip made of a filter paper combined with a water-resistant paper.

The shape of the through-hole and the liquid film formed in the through-hole in this optical analysis chip were observed in a manner similar to that of Experiment 4.

Preparation of Sample 0.098 g ($1.0 \times 10^{-4}$ mol) of sodium copper phthalocyanine tetrasulfonate (manufactured by Fujifilm Wako Pure Chemical Industries, Ltd., special grade) was dissolved in 10 ml of pure water to prepare a sodium copper phthalocyanine tetrasulfonate solution of 10 mmolkg$^{-1}$. 0.5 g of activated carbon (manufactured by Nacalai Tesque, Inc., charcoal activated (powder), 350 mesh) was dissolved in 10 ml of pure water to prepare a 5% activated carbon dispersion. These solutions were mixed and the resulting mixture was further diluted to prepare a mixed sample having a sodium copper phthalocyanine tetrasulfonate concentration of 0.1 mmolkg$^{-1}$ and an activated carbon concentration of 0.5%.

In addition, an activated carbon-free sample (concentration of sodium copper phthalocyanine tetrasulfonate: 0.1 mmolkg$^{-1}$) was prepared.

Analysis

Analysis Based on Absorption Spectrometry

A spectrometer similar to that used in Experiment 4 was used.

The light source of the light irradiation fiber and the light receiving fiber used in this analysis were similar to those of Experiment 4.

The absorbance in the range of 250 nm to 860 nm was measured.

Addition of Sample

As in Experiment 4, 60 μL of the prepared mixed sample solution was supplied to the optical analysis chip. 60 μL of the activated carbon-free sample was also added to the optical analysis chip in the same manner.

Results

The observation of the surface of the optical analysis chip to which the mixed sample solution was supplied revealed that black particles indicating the presence of activated carbon were retained in portions other than the through-hole region. This experiment also could confirm absence of the stagnation layer shown in FIG. 18(A) as a result of adjustment of the sample amount.

Figure 19:
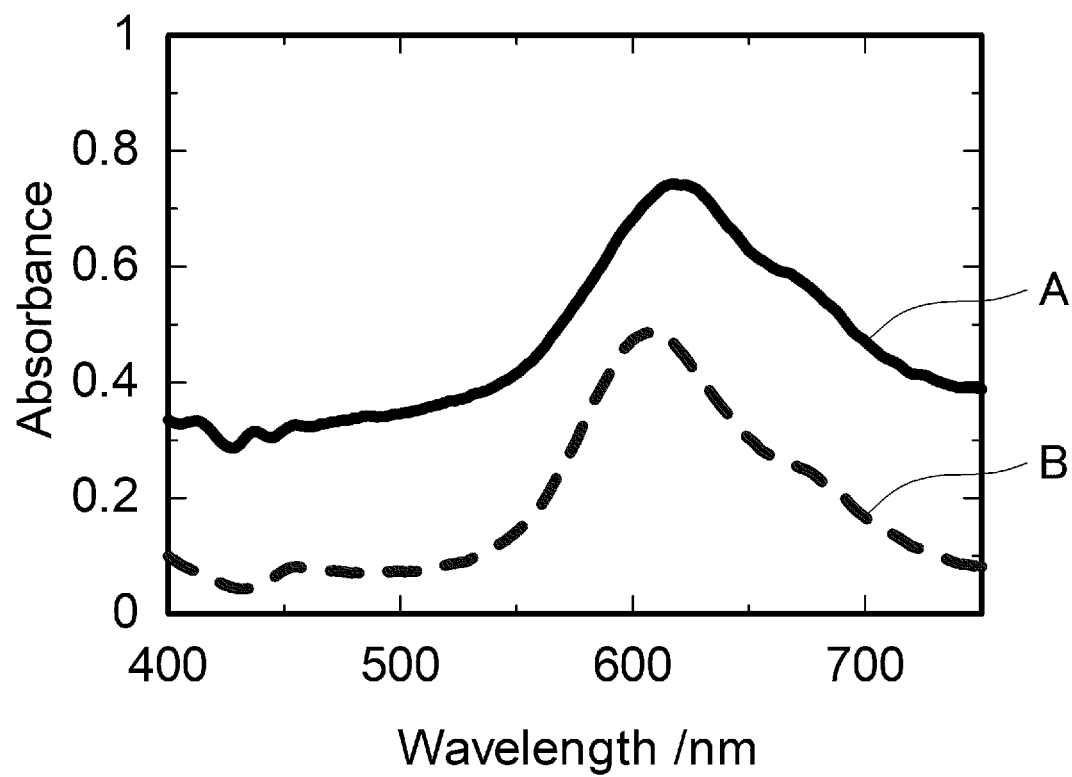
FIG. 19 is a diagram showing the results (absorption spectrum) of Experiment 5.

FIG. 19 shows the absorption spectra of the mixed sample solution (A) and the activated carbon-free sample (B). The measured absorbances (the difference in absorbance between the measured wavelengths 631 nm and 800 nm) of the mixed sample solution and the activated carbon-free sample were 0.355 and 0.341, respectively, and very similar absorbances could be obtained. In addition, the observed absorption spectra had substantially the same shape.

The results of the experiment revealed that the optical analysis chip is capable of appropriately measuring and quantifying the target component in the sample while removing coarse particles that interfere with the spectral measurement from the sample. It was also confirmed that, even when impurities (foreign substances) are contained in the sample, appropriate quantitative determination of the target component was possible by adjusting the addition amount, thereby preventing formation of the stagnation layer. More specifically, it was confirmed that, by preventing the sample from spreading due to the wetting caused by the formation of the stagnation layer, it is possible to prevent unremoved impurities (foreign substances) from spreading to the detection unit via the stagnation layer before the supplied sample permeates into the filter paper of the optical analysis chip.

Experiment 6
Suitability Test for Sample Containing Impurities
Preparation of Optical Analysis Chip A filter paper combined with a water-resistant paper similar to that used in Experiment 4 was prepared, and an aqueous cellulose nanofiber (CNF) solution was applied to the surface of the filter paper combined with a water-resistant paper to form a CNF layer having a film thickness of several tens of micrometers, thereby preparing a CNF filter paper combined with a water-resistant paper. A rectangle having a short side of about 6 mm and a long side of about 13 mm was cut out from this CNF filter paper combined with a water-resistant paper. A 5 mm square through-hole region having the plurality of through-holes was formed in the vicinity of one of the short sides of the cut piece (see FIG. 10(A)). Then, the CNF layer in the region to which the sample is added on the opposite side of the through-hole region was removed so as to allow the added sample to more easily permeate into the filter paper.

The CNF was used by diluting a CNF product produced by fibrillating pulp (CNF product having a solid content of 10%, manufactured by Sugino Machine Ltd., model number: Binfis AMa10010) with pure water at a concentration of 5%. In order to impart water resistance, a solution containing polyamide polyamine epichlorohydrin at a concentration ratio of 0.5% relative to CNF was used as the CNF solution.

A filter paper for chromatography (No. 526) was used as the filter paper.

A coating applicator (manufactured by Tester Sangyo Co., Ltd., model number: PI-1210) was used for the coating of the CNF solution.

Note that this CNF coating film corresponds to the "cover member" in the present embodiment.

Preparation of Through-Hole

A laser processing device similar to that used in Experiment 4 was used to form fine perforations (through-holes) on the filter paper combined with a water-resistant paper under the same conditions as those in the case of sample A so that the perforations (through-holes) penetrate through the surface and the rear side of the CNF filter paper combined with a water-resistant paper, thereby preparing an optical analysis chip made of a CNF filter paper combined with a water-resistant paper. As in the case of sample B of Experiment 4, the irradiation condition was as follows: laser power=20%, speed=5, 40 pulses/inch.

The shape of the through-hole and the liquid film formed in the through-hole in this optical analysis chip were observed in a manner similar to that of Experiment 4.

Preparation of Sample

A mixed sample (activated carbon concentration: 0.5%, sodium copper phthalocyanine tetrasulfonate concentration: 0.1 mmolkg$^{-1}$) and an activated carbon-free sample (sodium copper phthalocyanine tetrasulfonate concentration: 0.1 mmolkg$^{-1}$) were prepared in the same manner as in Experiment 4.

Analysis
Analysis Based on Absorption Spectrometry

A spectrometer similar to that used in Experiment 4 was used.

The light source of the light irradiation fiber and the light receiving fiber used in this analysis were similar to those of Experiment 4.

The measurement of absorbance was performed in the same manner as in Example 4.

Addition of Sample

60 µL of the mixed sample solution was added to the region of the optical analysis chip from which the CNF layer was removed. Similarly, 60 µL of the activated carbon-free sample was added to the region of the optical analysis chip from which the CNF layer was removed.

Results

The surface of the optical analysis chip to which the mixed sample solution was added was observed, with the result that the black particles indicating the presence of activated carbon was hardly observed in regions other than the addition region. The observation also revealed the absence of the stagnation layer shown in FIG. 18(A).

Figure 20:
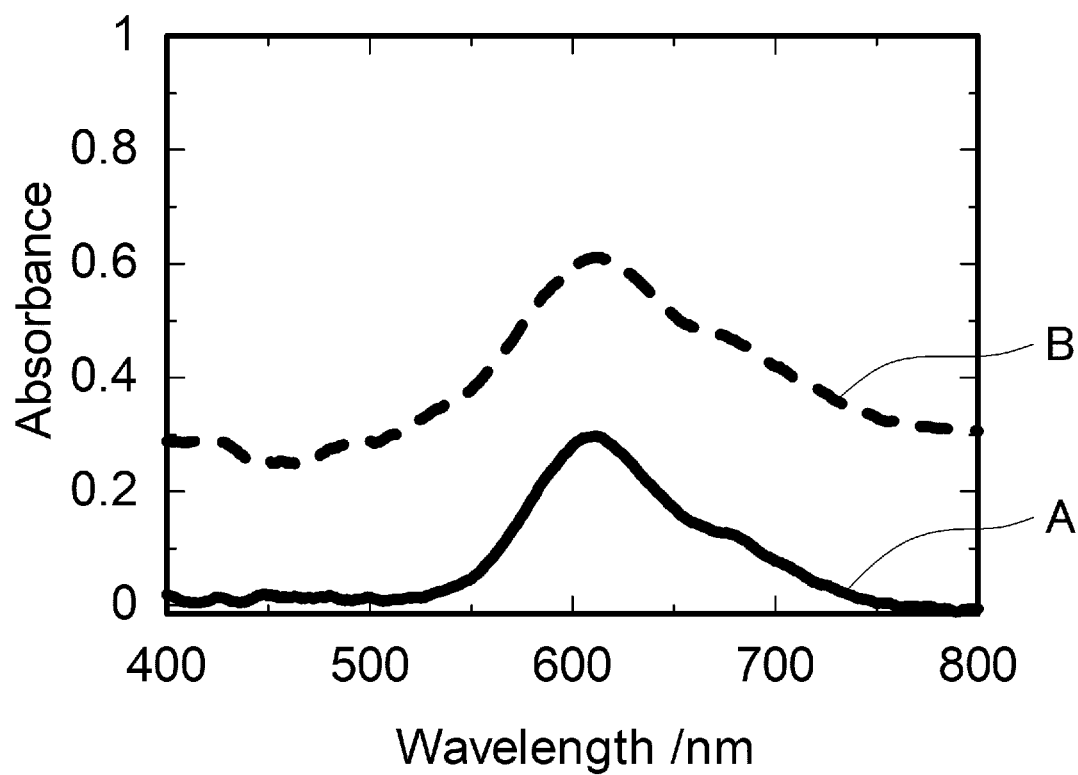
FIG. 20 is a diagram showing the results (absorption spectrum) of Experiment 6.

FIG. 20 shows the absorption spectra of the mixed sample solution (A) and the activated carbon-free sample (B). The measured absorbances (the difference in absorbance between the measured wavelengths 631 nm and 800 nm) of the mixed sample solution and the activated carbon-free sample were 0.249 and 0.266, respectively, which very similar absorbances can be obtained. It was also confirmed that the observed absorption spectra had substantially the same shape.

Based on the experiment results showing that the obtained absorption spectra had substantially the same shape, it was confirmed that the optical analysis chip having the CNF layer on the surface of the filter paper combined with the water-resistant paper is capable of appropriately removing coarse particles that interfere with the spectral measurement from the sample. It was also confirmed that the optical analysis chip provided with the CNF coating film enables to prevent spread of the added sample to a region other than the addition region (the region where the CNF coating film was removed). More specifically, it was confirmed that the added sample was successfully made to slide under the CNF coating film, and thereby permeated into the filter paper of the optical analysis chip. Moreover, it was confirmed that, since it is possible to suppress the supplied sample from spreading outside the supply region, the sample can be appropriately prevented from spreading on the surface of the filter paper of the optical analysis chip before it permeates into the filter paper, thereby preventing the spread of the sample due to wetting.

It was also confirmed that the sample can more smoothly permeate into the filter paper of the optical analysis chip by providing the addition region in the optical analysis chip.

Experiment 7
Quantitative Determination of Sodium Copper Phthalocyanine Tetrasulfonate Using Optical Analysis Chip Having Surface Cover Member
Preparation of Optical Analysis Chip A filter paper combined with a water-resistant paper was prepared in the same manner as in Experiment 4.

A filter paper for chromatography (No. 590) was used as the filter paper.

Preparation of Through-Holes

A laser processing device similar to that used in Experiment 4 was used to form fine perforations (through-holes) on the filter paper combined with a water-resistant paper under the same conditions as those in the case of sample A so that the perforations (through-holes) penetrate through the surface and the rear side of the filter paper combined with the water-resistant paper.

Surface Cover Member

Next, a surface cover member was adhered to the surface of the filter paper combined with a water-resistant paper excluding the region where the sample was added, thereby preparing an optical analysis chip made of a filter paper combined with a water-resistant paper having a cover.

This surface cover member used in this analysis was a product (cellophane tape: manufactured by Nichiban Co., Ltd., model number: CT-12S) made of a resin film base having an adhesive layer in one surface.

The shape of the through-hole and the liquid film formed in the through-hole in this optical analysis chip were observed in a manner similar to that of Experiment 4.

Preparation of Sample

A sample having a sodium copper phthalocyanine tetrasulfonate concentration of 0.1 mmolkg$^{-1}$ was prepared as in Experiment 4.

Analysis

Analysis Based on Absorption Spectrometry

A spectrometer similar to that used in Experiment 4 was used.

The light source of the light irradiation fiber and the light receiving fiber used in this analysis were similar to those of Experiment 4.

The absorbance in the range of 250 nm to 860 nm was measured.

Addition of Sample

As in Experiment 4, 60 µL of the prepared sample solution was added to the optical analysis chip.

Results

The observation of the surface of the optical analysis chip revealed that the liquid film was appropriately formed in each through-hole.

Figure 21:
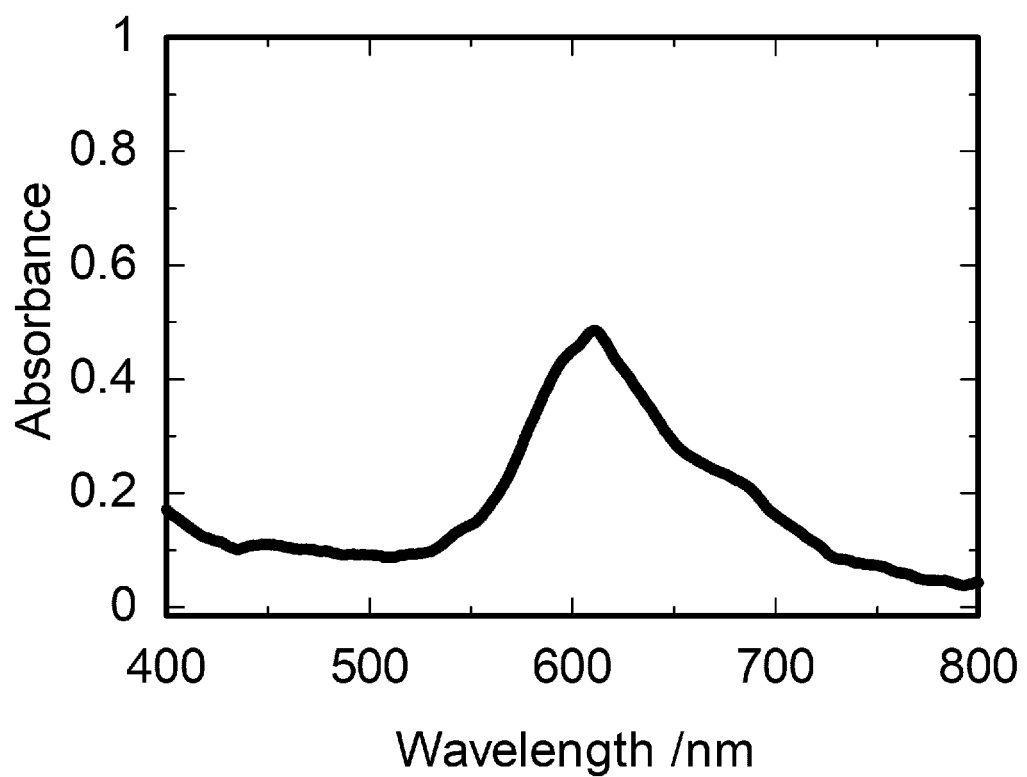
FIG. 21 is a diagram showing the results (absorption spectrum) of Experiment 7.

FIG. 21 shows the absorption spectra. The measured absorbance of the sample (the difference in absorbance between the measured wavelengths 631 nm and 800 nm) was 0.343.

The results of the experiment revealed that, also in the case where the optical analysis chip includes the surface cover member having a light transmissive property in the through-hole region, the spectral measurement was appropriately performed in the same manner as in Experiment 6. It was also confirmed that, by providing the surface cover member with the optical analysis chip, the added sample can be prevented from spreading on the surface of the filter paper of the optical analysis chip before it permeates into the filter paper, thereby preventing the spread of the sample due to wetting.

Experiment 8

Quantitative Determination of Sodium Copper Phthalocyanine Tetrasulfonate Using Optical Analysis Chip Made of CNF Layer and Water-Permeable Material Preparation of Optical Analysis Chip Polyethylene-terephthalate (PET) fibers having a fiber diameter of 12.5 µm and a fiber length of 0.2 mm were used as the water-impermeable material. The cellulose nanofibers (CNF) were obtained by treating Leaf Bleached Kraft Pulp (LBKP) using a machine (high-speed grinder: Super masscolloider MACA6-2, manufactured by Masuko Sangyo Co., Ltd.).

Then, a dispersion liquid containing CNF and PET fibers was prepared. This dispersion liquid was prepared to contain 15.3 parts by mass of PET fibers, 45.3 parts by mass of a CNF dispersion liquid, and 39.4 parts by mass of 0.5% polyoxyethylene aqueous solution, which are 100 parts by mass in total.

This dispersion liquid was applied to the surface of a commercially available water-resistant paper (water-resistant paper for color laser, extra thick, product number: LBP-WPF22MDP, manufactured by Sanwa Supply Inc.) using a coating machine (PI-1210, manufactured by Tester Sangyo Co., Ltd.), followed by drying with a drier, thereby preparing a sheet member (sheet thickness: about 200 µm) containing the CNF layer and the water-impermeable material.

A rectangle having a short side of about 6 mm and a long side of about 13 mm was cut out from this sheet member in the same manner as in FIG. 4. A 5 mm square through-hole region having a plurality of through-holes was formed in the vicinity of one of the short sides of the cut piece (see FIG. 10(A)).

Further, the sheet member was cut out so that the water-impermeable material (PET fibers) was substantially orthogonal to the longitudinal direction of the rectangle. More specifically, the orientation of the PET fibers was adjusted so as to be substantially orthogonal to the liquid travelling direction indicated by the arrow in FIG. 10(A).

Preparation of Through-Holes

A laser processing device similar to that used in Experiment 4 was used to form fine perforations (through-holes) penetrating through the surface and the rear side of the CNF-PET water-resistant paper, thereby preparing an optical analysis chip made of the CNF-PET water-resistant paper.

The irradiation condition was as follows: laser power=3%, speed=5, 40 pulses/inch.

The shape of the through-hole and the liquid film formed in the through-hole in this optical analysis chip were observed in a manner similar to that of Experiment 4.

Preparation of Sample

A sample having a sodium copper phthalocyanine tetrasulfonate concentration of 0.1 mmolkg$^{-1}$ was prepared as in Experiment 4.

Analysis

Analysis Based on Absorption Spectrometry

A spectrometer similar to that used in Experiment 4 was used.

The light source of the light irradiation fiber and the light receiving fiber used in this analysis were similar to those of Experiment 4.

The absorbance in the range of 250 nm to 860 nm was measured.

Addition of Sample

As in Experiment 4, 40 µL of the prepared sample solution was added to the optical analysis chip.

Results

The observation of the surface of the optical analysis chip revealed the presence of a large number of small holes on the surface. Further, it was confirmed that, the sample was not repelled on the surface but permeated into the chip when the sample was added. Furthermore, it was confirmed that a liquid film was appropriately formed in each through-hole.

It was also confirmed that about 70% of the PET fibers, which are a water-impermeable material, were oriented in the direction substantially orthogonal to the traveling direction (the direction shown by the arrow in FIG. 10A(A)) from the sample supply unit.

Figure 22:
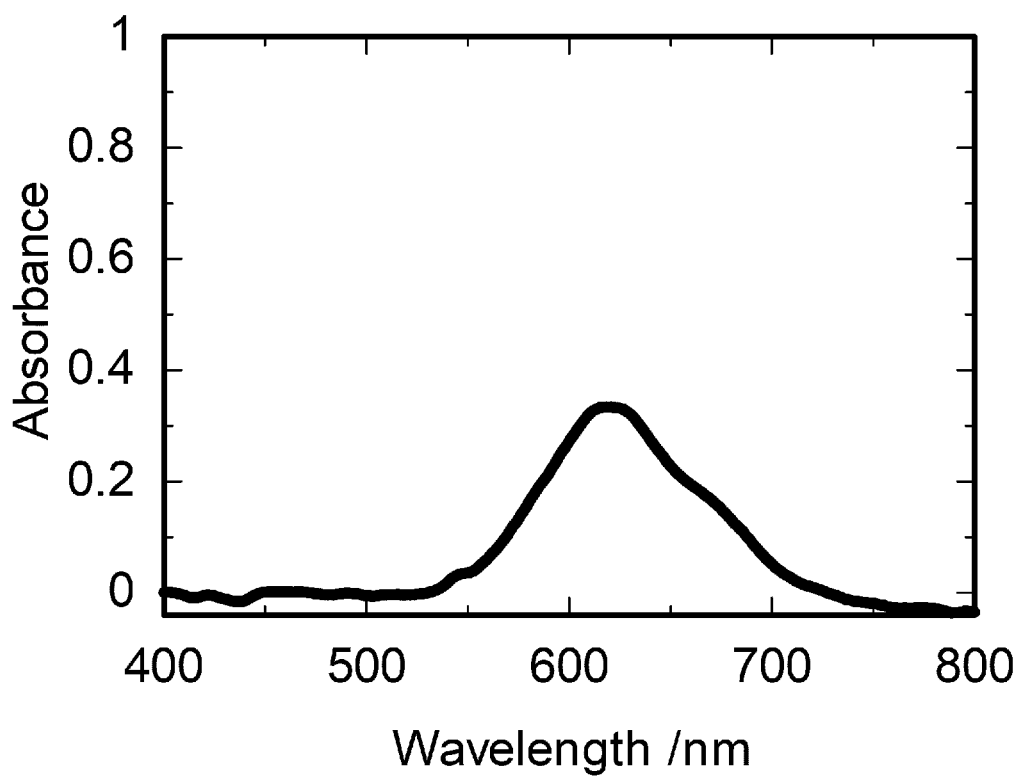
FIG. 22 is a diagram showing the results (absorption spectrum) of Experiment 8.

FIG. 22 shows the absorption spectra. The measured absorbance of the sample (the difference in absorbance between the measured wavelengths 631 nm and 800 nm) was 0.346.

It was confirmed that the target component in the sample can be appropriately measured and quantified even when the optical analysis chip made of the CNF layer and the water-permeable material was used.

INDUSTRIAL APPLICABILITY

The optical analysis chip of the present invention is suitable for an analytical tool for optical analysis in the fields of medicine, biochemistry, pharmaceutics, chemistry, environment, and the like.

REFERENCE NUMERALS

1: Optical Analysis Chip
10: Detection Unit
10h: Through-Hole
11: Base Material of Detection Unit
11h: Voids in Base Material
12: Water-Permeable Material
13: Water-Impermeable Material
14: Nanofiber Layer
20: Flow Path Unit
21: Flow Path Base Material
Lf: Liquid Film Formed in Through-Hole
SM: Spectrometer

The invention claimed is:

1. An optical analysis chip as an analysis tool for use in optical analysis, comprising:
   a detection unit having a base material wherein the detection unit has through-holes penetrating through a surface and a rear side of the base material,
   the detection unit comprising, in the base material, a plurality of voids that allow a liquid to pass through by capillary action and that communicate with the through-holes, and
   the through-holes being formed with a size that enables a liquid to be held by surface tension, wherein
   a plurality of openings of the voids are formed on inner wall surfaces of the through-holes.

2. The optical analysis chip according to claim 1, wherein:
   in the detection unit, the base material comprises a plurality of water-permeable materials that allows a liquid to pass though therein by capillary action.

3. The optical analysis chip according to claim 2, wherein:
   the base material of the detection unit is a filter paper.

4. The optical analysis chip according to claim 1, wherein:
   in the detection unit, the base material comprises a plurality of water-permeable materials that allows a liquid to pass though therein by capillary action, and a plurality of water-impermeable materials disposed between the water-permeable materials, and
   the voids are formed of the water-permeable materials and the water-impermeable materials.

5. The optical analysis chip according to claim 1, wherein:
   in the detection unit, the base material comprises a plurality of nanofiber layers made of nanofibers, and water-impermeable materials disposed between the plurality of nanofiber layers, and
   the voids are formed of the nanofiber layers and the water-impermeable materials.

6. The optical analysis chip according to claim 5, wherein:
   in the base material of the detection unit, the nanofiber layers positioned on a surface of the base material comprise holes that penetrate through the nanofiber layers.

7. The optical analysis chip according to claim 1, wherein:
   the optical analysis chip comprises a flow path unit that connects to the detection unit and that allows a liquid to pass through, and
   the flow path unit comprises a flow path base material having a plurality of voids that allow a liquid to pass through by capillary action.

8. The optical analysis chip according to claim 7, wherein:
   in the flow path unit, the flow path base material comprises a plurality of water-permeable materials that allows a liquid to pass though therein by capillary action.

9. The optical analysis chip according to claim 8, wherein:
   the flow path base material of the flow path unit is a filter paper.

10. The optical analysis chip according to claim 7, wherein:
    in the flow path unit, the flow path base material comprises a plurality of water-permeable materials that allows a liquid to pass though therein by capillary action, and a plurality of water-impermeable materials disposed between the water-permeable materials, and
    the voids are formed of the water-permeable materials and the water-impermeable materials.

11. The optical analysis chip according to claim 10, wherein:
    in the flow path unit, the water-impermeable materials are fibrous members that are arranged along a direction toward the detection unit.

12. The optical analysis chip according to claim 10, wherein:
    in the flow path unit, the water-impermeable materials are fibrous members that are arranged so as to intersect the direction toward the detection unit.

13. The optical analysis chip according to claim 7, wherein:
    in the flow path unit, the flow path base material comprises a plurality of nanofiber layers made of nanofibers, and water-impermeable materials disposed between the plurality of nanofiber layers, and
    the voids are formed of the nanofiber layers and the water-impermeable materials.

14. The optical analysis chip according to claim 13, wherein:
    in the flow path unit, the nanofiber layers disposed on the surface of the flow path base material comprise holes that penetrate through the nanofiber layers.

15. The optical analysis chip according to claim 7, wherein:
    the flow path base material of the flow path unit and the base material of the detection unit are integrally formed.

16. The optical analysis chip according to claim 1, wherein:
    in the detection unit, the base material comprises a shape retaining layer for retaining a shape in the rear side.

17. The optical analysis chip according to claim 16, wherein the shape retaining layer is formed of a water-impermeable base member, and
    the base member comprises an outer edge portion that protrudes outward relative to an outer edge of a layer that is positioned closer to a surface side of the base material than the base member.

18. The optical analysis chip according to claim 1, wherein:

the detection unit comprises a cover member having a light transmissive property in a region having the through-holes of the base material.

19. The optical analysis chip according to claim 18, wherein:

the cover member comprises a surface cover member provided on the surface of the base material.

20. The optical analysis chip according to claim 18, wherein:

the cover member comprises a back cover member on the rear side of the base material.

21. The optical analysis chip according to claim 18, wherein:

the cover member comprises a detection material on a plane facing the base material.

22. The optical analysis chip according to claim 1, wherein:

in the detection unit, the base material comprises a water-impermeable region that does not allow a liquid to pass through and that surrounds a peripheral portion of a region having the through-holes, and a part of the water-impermeable region has a water-permeable region that allows a liquid to pass through.

23. The optical analysis chip according to claim 22, wherein:

the water-impermeable region has a groove that surrounds the peripheral portion while retaining the water-permeable region, and the groove is formed by penetrating the surface and the rear side of the base material of the detection unit.

24. The optical analysis chip according to claim 1, wherein:

in the detection unit, each of the through-holes has an opening diameter of 50 μm to 1000 μm.

* * * * *